(12) United States Patent
Spiegel et al.

(10) Patent No.: US 12,042,542 B2
(45) Date of Patent: *Jul. 23, 2024

(54) SYNTHETIC ANTIBODY MIMETIC COMPOUNDS (SYAMS) TARGETING CANCER, ESPECIALLY PROSTATE CANCER

(71) Applicant: YALE UNIVERSITY, New Haven, CT (US)

(72) Inventors: David A. Spiegel, New Haven, CT (US); Patrick McEnaney, Jupiter, FL (US); Kelly Fitzgerald, Upton, MA (US)

(73) Assignee: YALE UNIVERSITY, New Haven, CT (US)

( * ) Notice: Subject to any disclaimer, the term of this patent is extended or adjusted under 35 U.S.C. 154(b) by 381 days.

This patent is subject to a terminal disclaimer.

(21) Appl. No.: 17/122,319

(22) Filed: Dec. 15, 2020

(65) Prior Publication Data

US 2022/0111060 A1    Apr. 14, 2022

Related U.S. Application Data

(62) Division of application No. 16/180,494, filed on Nov. 5, 2018, now Pat. No. 10,912,836, which is a division of application No. 14/888,779, filed as application No. PCT/US2013/039472 on May 3, 2013, now Pat. No. 10,117,943.

(51) Int. Cl.
| | |
|---|---|
| *A61K 47/55* | (2017.01) |
| *A61K 31/194* | (2006.01) |
| *A61K 38/10* | (2006.01) |
| *A61K 45/06* | (2006.01) |
| *A61K 47/54* | (2017.01) |
| *C07D 249/04* | (2006.01) |
| *C07D 249/06* | (2006.01) |

(52) U.S. Cl.
CPC ............ *A61K 47/55* (2017.08); *A61K 31/194* (2013.01); *A61K 38/10* (2013.01); *A61K 45/06* (2013.01); *A61K 47/54* (2017.08); *C07D 249/04* (2013.01); *C07D 249/06* (2013.01)

(58) Field of Classification Search
CPC ...... A61K 31/194; A61K 38/10; A61K 45/06; A61K 47/55; A61P 35/02; A61P 35/04
See application file for complete search history.

(56) References Cited

U.S. PATENT DOCUMENTS

| | | |
|---|---|---|
| 8,852,630 B2 | 10/2014 | Spiegel et al. |
| 8,859,509 B2 | 10/2014 | Spiegel et al. |
| 9,296,708 B2 | 3/2016 | Spiegel et al. |
| 2011/0201563 A1 | 8/2011 | Spiegel et al. |

FOREIGN PATENT DOCUMENTS

| | | |
|---|---|---|
| WO | 2001009192 A1 | 2/2001 |
| WO | 2009139863 A2 | 11/2009 |
| WO | 2010108125 A2 | 9/2010 |
| WO | 2011046946 A2 | 4/2011 |
| WO | 2012068366 A2 | 5/2012 |

OTHER PUBLICATIONS

Hansel TT, et al. The safety and side effects of monoclonal antibodies. Nat Rev Drug Discov 2010, 9 (4), 325-338.
Weiner LM. Building better magic bullets-improving unconjugated monoclonal antibody therapy for cancer. Nat Rev Cancer 2007, 7 (9), 701-706.
Siberil S, et al. Fc gamma R: The key to optimize therapeutic antibodies? Crit. Rev. Oncol./Hematol. 2007, 62 (1), 26-33.
McEnaney PJ, et al. Antibody-Recruiting Molecules: An Emerging Paradigm for Engaging Immune Function in Treating Human Disease. ACS Chemical Biology 2012, 7 (7), 1139-1151.
Cuesta NM, et al. Multivalentantibodies: when design surpasses evolution. Trends in biotechnology 2010, 28 (7), 355-362.
James Nd, et al. A phase II study of the bispecific antibody MDX-H210 (anti-HERZ X CD64) with GM-CSF in HERZ+ advanced prostate cancer. Br J Cancer 2001, 85 (2), 152-156.
Li Y, et al. Mechanism of Neutralization by the Broadly Neutralizing HIV-I Monoclonal Antibody VRCOL Journal of Virology 2011, 85 (17), 8954-8967.
Jakobsche CE, et al. Reprogramming Urokinase into an Antibody-Recruiting Anticancer Agent. ACS Chemical Biology 2011, 7 (2), 316-321.
Murelli RP, et al. Chemical Control over Immune Recognition: A Class of Antibody-Recruiting Small Molecules That Target Prostate Cancer. Journal of the American Chemical Society 2009, 131 ( 4 7), 17090- 17092.

(Continued)

*Primary Examiner* — Alicia L Otton
(74) *Attorney, Agent, or Firm* — Henry D. Coleman; R. Neil Sudol

(57) ABSTRACT

The present invention relates to compounds which function as antibody mimetic compounds. These compounds are bifunctional/multifunctional compounds which contain at least one cancer cell binding moiety which selectively binds to prostate specific membrane antigen (PSMA) and a FC receptor binding moiety which modulates an FC immune receptor, preferably a FcγRI receptor. Compounds according to the present invention bind selectively to cancer cells which upregulate PSMA and through that interaction, place the Fc receptor binding moiety of the compound in proximity to a Fc receptor, preferably a FcγRI receptor, which can modulate (preferably, upregulate) a humoral response in a patient to cancer cells. Through this biological action of the compounds according to the present invention, cancer cells, including metastatic cancer cells, especially prostate cancer cells can be immune regulated, resulting in the favorable therapy of cancer in a patient. Methods of using these compounds to treat cancer and/or reduce the likelihood of metastatis of cancer are additional aspects of the present invention.

20 Claims, 28 Drawing Sheets

(56) References Cited

OTHER PUBLICATIONS

Parker CG, et al. An Antibody-Recruiting Small Molecule That Targets HIV gp 120. Journal of the American Chemical Society 2009, 131 (45), 16392-16394.

Spiegel DA, et al. Grand Challenge Commentary: Synthetic immunology to engineer human immunity. Nat Chem Biol 2010, 6 (12), 871-872.

Society, A. C., Cancer Facts & Figures 2011. Society, A. C., Ed. Atlanta, 2011.

Nimmerjahn F, Ravetch JV. Fc[gamma) receptors as regulators of immune responses. Nat Rev Immunol 2008, 8 (1 ), 34-4 7.

Bonetto S, et al. Identification of cyclic peptides able to mimic the functional epitope ofigGI-Fc for human Fe gamma RI. Faseb J. 2009, 23 (2), 575-585.

Berntzen G, et al. Identification of a High Affinity Fe gamma RUA-binding Peptide That Distinguishes Fe gamma RIIA from Fe gamma RHB and Exploits Fe gamma RUA-mediated Phagocytosis and Degradation. J. Biol. Chem. 2009, 284 (2), 1126-1135.

Cendron AC, et al. An FcyRIIa-binding peptide that mimics the interaction between FcyRIIa and IgG. Molecular Immunology 2008, 45 (2), 307-319.

Wang SY, et al. Depletion of the C3 component of complement enhances the ability of rituximab-coated target cells to activate human NK cells and improves the efficacy of monoclonal antibody therapy in an in vivo model. Blood 2009, 114 (26), 5322-5330.

McEnaney PJ, et al. Antibody-Recruiting Molecules: An Emerging Paradigm for Engaging Immune Function in Treating Human Disease. ACS Chem Biol, 2012;3:1139-1151.

Ross JS, et al. Anticancer Antibodies. Am J Clin Pathol, 2003;119:472-485.

FIGURE 5

| Target | Bead Labeling (pmol/bead) | Measured PSMA/um² | Calculated PSMA/um² | Observed % Phagocytosis (50nM SyAM-P2) |
|---|---|---|---|---|
| Beads | 8.2 | 5577 | | 46.2 |
| | 5.7 | | 3876 | 24.0 |
| | 2.9 | | 1972 | 10.1 |
| RM1.PGLS | | 918 | | 0 |

FIGURE 13

| | Macrophages + Targets only | + 50nM ARM-P8 + anti-DNP ab | + 10nM 3 |
|---|---|---|---|
| % of attached double positives | 8.2 | 36.4 | 19.0 |
| % of in-focus completed phagocytosis | 4.0 | 8.4 | 5.1 |
| % of in-focus initiated phagocytosis | 1.2 | 4.6 | 3.2 |
| % combined in-focus completed + initiated | 5.2 | 13.0 | 8.3 |

CP33

SyAM-P1 (With Biotin)

Synthesis of SyAm-P3 (Without Biotin)

Urea Formation

Linker Synthesis

SyAM-P3

SYNTHETIC ANTIBODY MIMETIC COMPOUNDS (SYAMS) TARGETING CANCER, ESPECIALLY PROSTATE CANCER

RELATED APPLICATIONS

The present application is a divisional application of U.S. application Ser. No. 16/180,494 filed on Nov. 5, 2018, which is itself a divisional application of U.S. application Ser. No. 14/888,779 filed on Nov. 3, 2015, which issued on Nov. 6, 2018 as U.S. Pat. No. 10,117,943, which is a 371 national phase filing of international patent application number PCT/US2013/039472 filed on May 3, 2013, the entire contents of which said three applications are incorporated into the present application herein.

GRANT SUPPORT

This invention was made with government support under GM100283 and OD002913 awarded by National Institutes of Health. The government has certain rights in the invention.

FIELD OF THE INVENTION

The present invention relates to compounds which function as synthetic antibody mimetic compounds. Compounds according to the present invention are bifunctional/multifunctional compounds which contain at least one cancer cell binding moiety which selectively binds to prostate specific membrane antigen (PSMA) and a FC receptor binding moiety which modulates an FC immune receptor, preferably a FcγRI receptor. Compounds according to the present invention bind selectively to cancer cells which upregulate PSMA and through that interaction, place the Fc receptor binding moiety of the compound in proximity to a Fc receptor, preferably a FcγRI receptor, which can modulate (preferably, upregulate) a humoral response in a patient to cancer cells. Through this biological action of the compounds according to the present invention, cancer cells, including metastatic cancer cells, especially prostate cancer cells can be immune regulated, resulting in the favorable therapy of cancer in a patient. Methods of using these compounds to treat cancer and/or reduce the likelihood of metastatis of cancer are additional aspects of the present invention.

BACKGROUND OF THE INVENTION

A growing wealth of data indicates that targeted therapies can mobilize a patient's own immune system to destroy malignancies with fewer side effects than traditional chemotherapy. Since it is estimated that 41% of Americans—almost 1 in 2 people—born in 2011 will develop cancer in their lifetime, the generation of more effective cancer immunotherapies is a high priority. These therapies include monoclonal antibodies (mAbs) that direct innate immune cells to tumor-associated antigens (TAA) as well as cancer "vaccines" that take many forms (including injections of tumor proteins with adjuvants or ex vivo primed dendritic cells) and are designed with the intention of inducing long-lasting anti-tumor T-cells.

The objective of the present inventors' research is to develop novel compounds capable of stimulating immune responses against tumors. The introduction of monoclonal antibodies (mAbs) has revolutionized the field of immunotherapy, particularly cancer therapy. Although mAbs have become a mainstay of cancer therapeutics, they possess serious drawbacks.[1] mAbs are limited by their dangerous immunological side-reactions, lack of oral bioavailability, and high cost of production and administration. Development of synthetic molecules that mimic antibody function may provide an effective solution for the aforementioned problems.

Current research is exploring the development of new therapeutics that take advantage of the immune system's natural responses. Optimization of the Fc region of unconjugated monoclonal antibodies to increase their efficacy and response, has been of great interest.[2,3] One recently developed derivative of monoclonal antibodies, bispecific antibodies, ligates two Fabs with different target specificity. One Fab region binds to the target protein of interest and the other binds to an immune receptor of choice[4,5], including FcγRI[6], e.g., bispecific antibodies targeting HER2 and FcγRI.[6] In an alternative approach, the present inventors, and others, have utilized rational design to construct synthetic systems capable of performing, or templating, complex immunological functions.[7]

As a result, several antibody-recruiting molecules (ARMs) that can modulate the immune system[8] have occurred. ARMs are bifunctional synthetic molecules that contain a target-binding terminus (TBT), which binds to pathogenic surface proteins with high affinity and specificity, and an antibody-binding terminus (ABT) that recruits endogenous antibodies. We have shown that these molecules are capable of eliciting a targeted immune response selectively against both cancer and virus infected cells. This topic has been reviewed recently.[4]

Notwithstanding the development of ARMs, the manipulation of the immune system with fully synthetic molecules is currently in its infancy.[9] In the present invention, a relatively small molecular weight antibody mimic can perform both targeting and immune effector functions, an approach which holds greater promise for the treatment of cancer, especially prostate cancer. For the development of this fully synthetic antibody mimetic, we chose prostate cancer as our pathogenic target, although the approach can be used anywhere PSMA is expressed, including virtually all cancers, but especially prostate cancer and metastatic prostate cancer.

The choice of prostate cancer as a target for the development of the present invention reflects its severity in causing disease and death. Prostate cancer is the second leading cause of cancer related deaths among American males, and current strategies for treatment often leads to relapse and undesirable side effects.[10] It has been predicted that one out of every six American men will develop prostate cancer during their lifetime. Currently, there are no clinically approved monoclonal antibody-based drugs targeting prostate cancer. Obviously, an immunological approach to the treatment of prostate cancer represents an approach with great potential, however, the negative attributes of the present immunological approaches must be ameliorated for this general approach to be successful. The present invention represents an alternative approach to address these problems.

The Present Invention

The current work which is presented in this application has led to the inventive development of a fully synthetic functional mimetic of an antibody that can overcome some of the drawbacks that are limiting the therapeutic potential of monoclonal antibodies. This new approach leverages the advantages of traditional small molecules with those of next-generation biologics to address the current limitations. Here, we report that a rationally designed synthetic molecule, called "synthetic antibody mimetic targeting prostate cancer" (SyAM-P), which is capable of redirecting the immunological functions of FcγRI towards targets displaying prostate specific membrane antigen (PSMA), thus targeting and eradicating cancer cells which upregulate PSMA, including prostate cancer cells, including metastatic prostate cancer cells. The inventors here present the first examples of synthetic molecules that display the properties and functions of an antibody, which entails the selective targeting of an immune response against a pathogenic target, in this case cancer cells, including metastatic cancer cells, especially prostate cancer cells and metastatic prostate cancer cells.

The present invention relates to compounds which are designated SyAM-Ps. SyAM-Ps are multifunctional small molecules designed to stimulate both innate and adaptive anti-tumor immune responses, especially immune responses which are modulated through FcγRI. The inventors have previously developed bifunctional antibody recruiting molecules (ARMs) able to redirect endogenous antibodies to prostate cancer cells expressing prostate specific membrane antigen (PSMA). The present invention enhances the immunostimulatory properties of ARMs by attaching modulators of FcγRI (potent modulators of humoral response) to the ARM scaffold. The binding moieties from the parent compound target the cancer cells which exhibit an upregulation of PSMA, in particular, prostate cancer cells, while the additional FcγRI motif activates a local humor response for induction of immunologic memory against the tumor. The result is an effect which provides synergistic anticancer activity which is substantially greater than the anticancer activity of individual functional molecules which are not linked together as in the present invention.

BRIEF DESCRIPTION OF THE FIGURES

FIG. 5, Table 1, shows phagocytosis of PSMA coated 6 μm beads by IFN-γ primed U937 cells in the presence of 50 nM of compound 2. The table lists the measured PSMA per square μm using phycoerythrin labeled anti-PSMA antibody for 8.2 pmol/bead. Calculated PSMA per square μm for 5.7 pmol/bead and 2.9 pmol/bead on loading capacity compared to 8.2 pmol/bead. PSMA measurement of RM1.PGLS cells using phycoerythrin anti-PSMA antibody. Phagocytosis of targets performed with primed U937 cells and 50 nM compound 2.

FIG. 13, Table 2 shows Amnis phagocytosis: attached double poisitives refer to all events scored as ADCP in traditional FACS where targets and effectors are stained two different colors. All in-focus events collected by Amnis imagestreamflow cytometry were then classified as "completed" (where a target is entirely engulfed by a macrophage) or as "initiated" (where a clear phagocytic cup had formed between macrophage and target).

OBJECTS OF THE INVENTION

Figure 1:
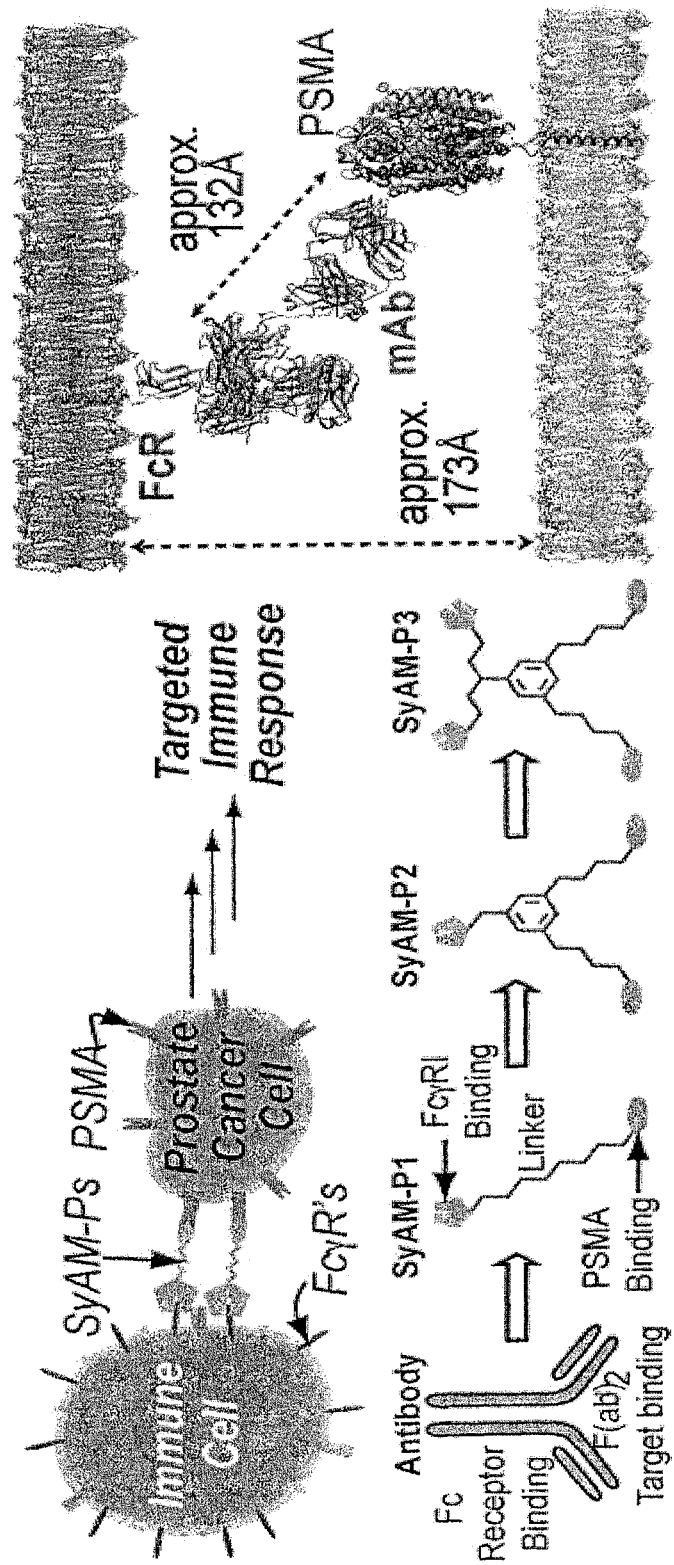
FIG. 1 shows A) depiction of proposed mechanism of action of the synthetic antibody mimetics; B) shows a modeling of membrane distances and length requirements during the interaction between a monoclonal antibody against PSMA binding to an Fc receptor; and C) shows a schematic of evolution of design of SyAM-P from monoclonal antibody template.

It is an object of the invention to provide chimeric bifunctional and multifunctional compounds which can be used to treat virtually any cancer (including metastatic cancer), especially including prostate cancer and metastatic prostate cancer.

It is another object of the invention to provide compounds which contain a cell binding moiety which binds to prostate specific membrane antigen (PSMA) of cancer cells, especially prostate cancer cells and metastatic prostate cancer cells and an Fc receptor binding moiety which binds to Fc receptors, in particular FcγRI receptors, and modulates a humoral/antibody response to cancer cells to which the compounds bind in order to cause cancer cell death and to treat cancer.

It is an additional object of the invention to provide chimeric bifunctional and multifunctional compounds which can be used to provide pharmaceutical compositions, including pharmaceutical compositions which include additional bioactive agents or agents which assist in the treatment of cancer, especially prostate cancer, including metastatic prostate cancer.

It is still another object of the invention to provide methods for treating cancer, especially prostate cancer, including metastatic prostate cancer using chimeric bifunctional and multifunctional compounds according to the present invention which exhibit unexpected and synergistic anticancer activity.

Yet a further object of the invention is to provide methods for inhibiting and/or reducing the likelihood of metastatis of cancer, especially including metastatic prostate cancer.

These and/or other objects of the invention may be readily gleaned from a review of the invention as described herein.

BRIEF DESCRIPTION OF THE INVENTION

In one embodiment, the invention provides bifunctional or multifunctional compounds which bind to prostate specific membrane antigen (PMSA) on cancer cells and separately, to a Fc receptor, often a FcγRI receptor through the [IBT] group. Through modulation of the Fc receptor (often a Fcγ receptor, most often a FcγRI receptor) the compound, situated on the surface of a cancer cell (often a prostate cancer cell and/or a metastatic cancer cell) stimulates immune effector cells, thus increasing immune signaling and phagocytic and/or cytotoxic responses acting in a synergistic manner to assist in eliminating cancer cells from tissue, thus treating the disease.

In one embodiment, the present invention relates to compounds according to the general formula:

where [IBT] is an Fc (often a Fcγ receptor, most often a FcγRI receptor) receptor binding moiety;

[CBT] is a cell binding moiety which binds to prostate specific membrane antigen (PSMA);

$L_1$ and $L_2$ are linker groups (which groups may include one or more bifunctional connector groups [CON} or more than one linker to provide an extended linker group);

[MULTICON} is a bifunctional or multifunctional connector group (preferably, multifunctional) which, when present, connects at least one [IBT] group to at least one [CBT] group through a linker;

MCON is an integer from 0 to 10, often 1 to 10, more often 1 to 5, often 0, 1 or 2;

n and n' are each independently n integer from 1 to 15, often 2 to 10, often 2 to 5, more often 2 or 3, or 2, 3, 4 5 or 6;

NL1 and NL2 are each an integer from 0 to 10, often 1 to 10, often 2 to 5, more often 2 or 3, with the proviso that n≥NL1 and n'≥NL2.

In another embodiment, [IBT] is CP33 (see FIG. 2 and FIG. 14), which exhibits excellent activity as a modulator of FCγRI receptors and is particularly effective at enhancing immune effector cells (e.g., macrophages and eosinophils) to provide a selective phagocytic and/or cytotoxic response, including opsonization, of the cancer cells, especially prostate cancer, resulting in the eradication of cancer cells and consequently, cancer tissue. In addition, compounds according to the present invention are believed to induce long term immunity against cancer tissue in the patient, thus reducing the likelihood of a relapse of cancer in a patient who has seen a cancer remission. Thus, compounds according to the present invention may be used in the treatment and prevention of cancer and metastatic cancer, especially including prostate cancer and metastatic prostate cancer. Compounds according to the present invention will often contain at least one [IBT] group and at least two [CBT] groups, often at least two [IBT] groups and two [CBT] groups and often two or three [IBT] groups and two or three [CBT] groups.

Additional compounds according to the present invention include compounds according to the chemical structure:

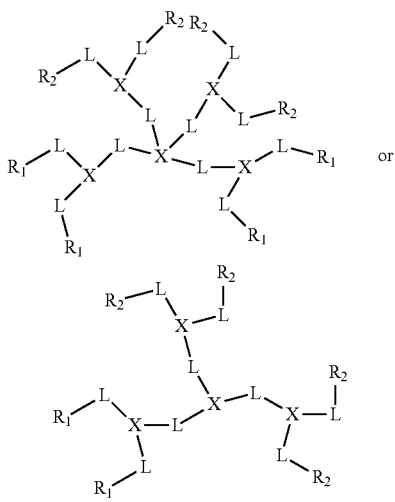

Where $R_1$ is a [IBT] group, often CB33;

$R_2$ is a [CBT] group; often

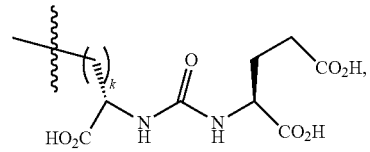

where k is 4, which is optionally directly linked to a connector group [CON], often a triazole connector group at the ring nitrogen

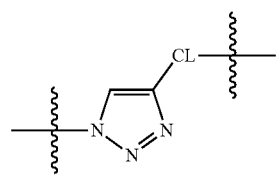

Where CL is

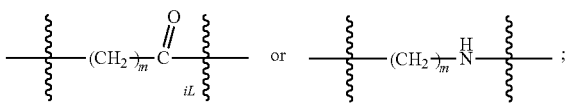

m is an integer from 0 to 12, often 0, 1, 2, 3, 4, 5, 6 and iL is 0 or 1, often 1;

X is a [MULTICON] group as otherwise described herein, often a group

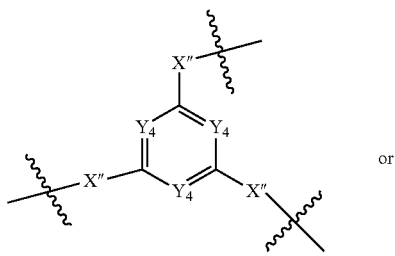

or

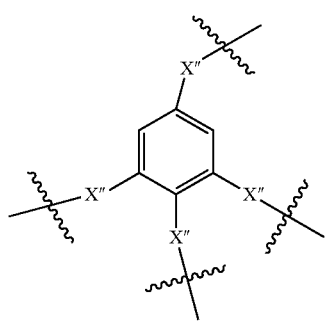

where $Y_4$ is C—H or N; and

Each X" is independently derived from an electrophilic or nucleophilic group, preferably $(CH_2)_{n''}O$, $(CH_2)_{n''}N^{RCON}$, $(CH_2)_{n''}S$, $(CH_2)_{n''}$ or $(CH_2)_{n''}C=O$ or one or more of X" is a [CON] group, often a

Figure 2:
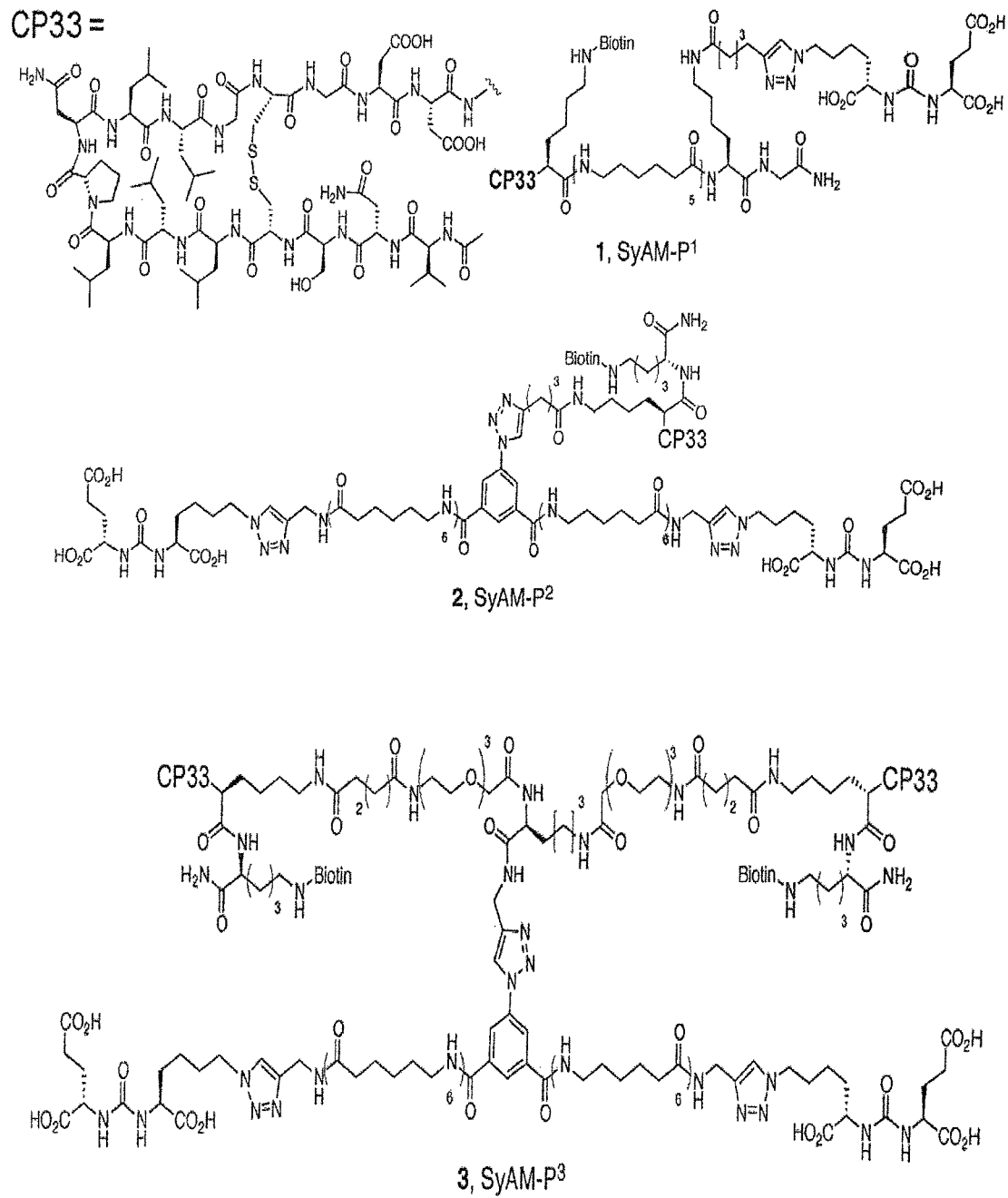
FIG. 2 exemplifies compounds and related moieties according to the present invention. CP33 is a FcγRI targeting motif 1, SyAM-P1, first generation displaying a single FcγRI and PSMA binding motifs linked with aminocaproic units. 2, SyAm-P2, second generation displaying a pair of PSMA targeting motifs linked to a single CP33 motif. 3, SyAM-P3, third generation displaying a pair of PSMA targeting motifs linked to a single CP33 motif. The biotin moiety is present as a handle so that the compounds may be readily isolated or identified in experiments which are otherwise disclosed herein. In practice, therapeutic compounds according to the present invention avoid the inclusion of a biotin molecule and the compounds contain a hydrogen, alkyl group or an acyl group at the amine group bonded to the biotin moiety depicted in the figure. 3, SyAm-P3, third generation displaying a pair of PSMA targeting motifs linked to a pair of CP33 targeting moieties/molecules.

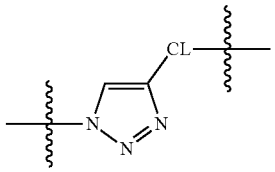

group linked through the amine to the ring structure of [MULTICON] where CL is the same as above;

the substitutent RCON is H or a $C_1$-$C_3$ alkyl, preferably H or $CH_3$ and n" is 0, 1, 2 or 3, and L is a linker group as otherwise described herein, often a group (see FIG. 2, compound 1, 2, or 3 which links a [CBT] moiety to a [MULTICON] molecule) according to the chemical structure:

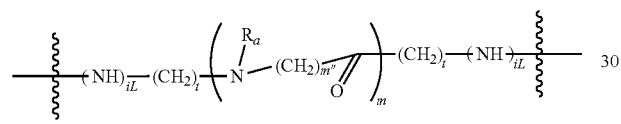

where $R_a$ is H or $CH_3$, most often H;

m is an integer from 1 to 12, often 1, 2, 3, 4, 5, or 6;

m" is an integer 1, 2, 3, 4, 5, or 6, often 6;

t is 0, 1, 2, 3, 4, 5, or 6; and iL is 0 or 1, often 1, wherein L may be linked to a [CON] group and a [CBT] group at one end and a [MULTICON] group on the other end; or Alternatively, L above, links an [IBT] group to a [MULTICON] molecule (as in compound 1 of FIG. 2) either directly or through at least one amino acid (often, an oligopeptide containing from 1 to 10 amino acid groups, often lysine or a glycine lysine dipeptide as depicted in compound 1 of FIG. 2), or Alternatively, in the case of a Linker L linking [IBT] to a [MULTICON] group (as in compound 2 of FIG. 2), the linker L is a peptide linker comprising from 1 to 10 peptides, often a lysine amino acid or a dilysine oligopeptide (the free carboxylic acid and amine of lysine may be end-capped with an amine in the case of the carboxylic acid or an acyl group in the case of a free amine) or other group to prevent further reactivity); or Alternatively, in the case of a Linker L linking more than one [IBT] group to a [MULTICON] Group, often L is a complex linker group (as depicted in compound 3 of FIG. 2) which is made up of an ethylene oxide containing amine group

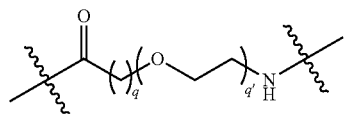

where q is 1, 2, 3 or 4 and q' is 1 to 12, often 1, 2, 3, 4, 5 or 6, the keto group is linked to an amino acid group which is linked to [IBT], often CP33, through a diketo group

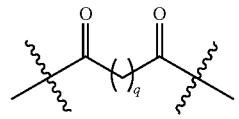

and an amino acid often lysine, or an amino acid dipeptide, often dilysine, one of which lysines is directly bonded to CP33, and another amino acid (often lysine) which links the above ethylene oxide amine group to a [MULTICON] group through a [CON] group, most often a triazole.

In other embodiments, compounds according to the present invention may be represented by the structures:

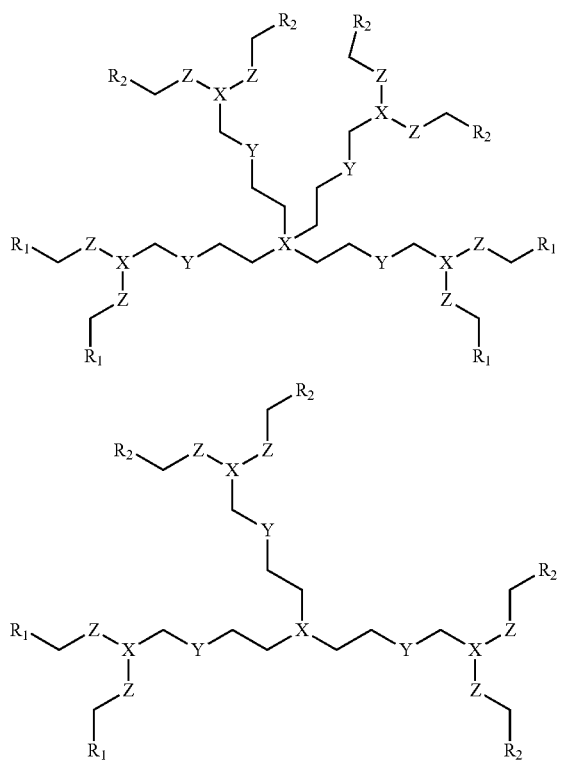

Where $R_1$ is a [IBT] group, often CB33;

$R_2$ is a [CBT] group; often

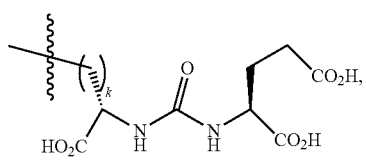

where k is 4, which is optionally directly linked to a connector group [CON], often a triazole connector group at the ring nitrogen X is a [MULTICON] group as otherwise described herein, often a group

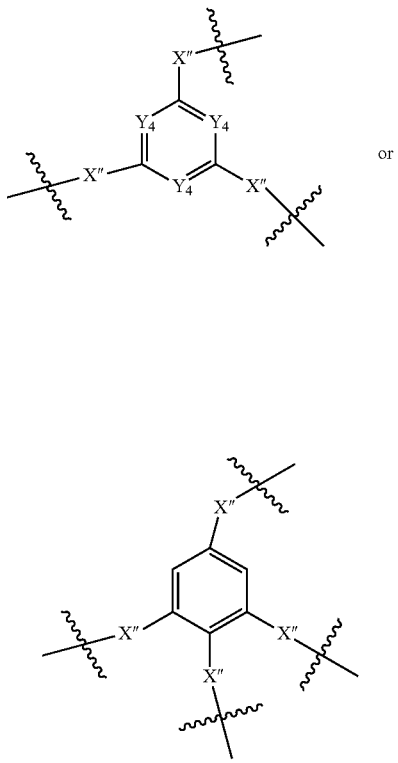

where $Y_4$ is C—H or N; and

Each X" is independently derived from an electrophilic or nucleophilic group, preferably $(CH_2)_{n''}O$, $(CH_2)_{n''}N^{RCON}$, $(CH_2)_{n''}S$, $(CH_2)_{n''}$ or $(CH_2)_{n''}C=O$ or one or more of X" is a [CON] group

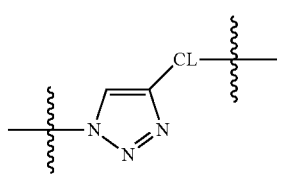

linked through the amine to the ring structure of [MULTICON]

Where CL is

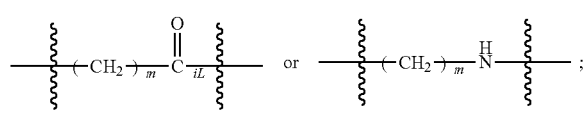

m in CL is an integer from 0 to 12, often 0, 1, 2, 3, 4, 5 or 6;

and iL is 0 or 1, often 1;

the substitutent RCON is H or a $C_1$-$C_3$ alkyl, preferably H or $CH_3$ and n" is 0, 1, 2 or 3;

and Z and Y are each independently

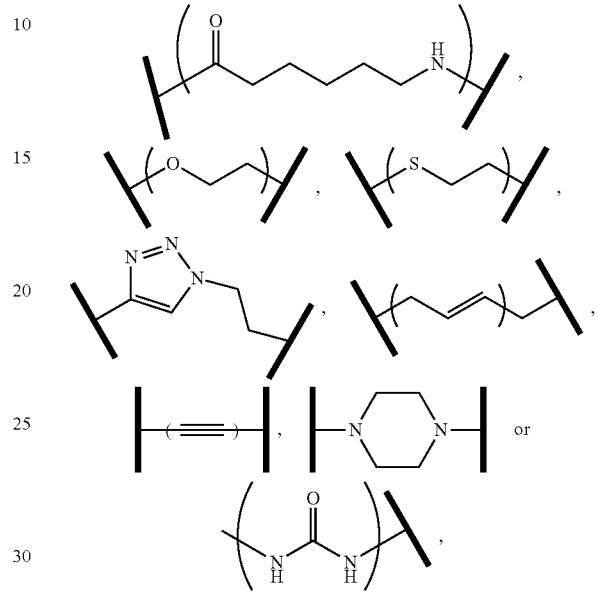

or a pharmaceutically acceptable salt, stereoisomer, solvate or polymorph thereof.

In an additional aspect of the invention, a pharmaceutical composition comprises an effective amount of a bifunctional/multifunctional compound as described above, optionally and preferably in combination with a pharmaceutically acceptable carrier, additive or excipient. In alternative aspects, pharmaceutical combination compositions comprise an effective amount of at least one bifunctional/multifunctional compound as described herein, in combination with at least one additional agent which is used to treat cancer, including prostate cancer, especially including metastatic prostate cancer or a secondary condition or effect of cancer, especially prostate cancer (e.g., bone pain, hyperplasia, osteoporosis, etc. as otherwise described herein).

In a further aspect of the invention, compounds according to the present invention are used to treat or reduce the likelihood of cancer, including metastatic cancer in a patient, especially prostate cancer in male patients in need thereof and to reduce the likelihood that a cancer, especially prostate cancer, will metastasize or that a cancer in remission will recur. The method of treating cancer comprises administering to a patient in need an effective amount of a trifunctional chimeric compound as otherwise described herein in combination with a pharmaceutically acceptable carrier, additive or excipient, optionally in further combination with at least one additional agent which is effective in treating cancer, especially including prostate cancer, metastatic cancer or one or more of its secondary conditions or effects.

The present invention also relates to a method for inhibiting prostate cancer to reduce or inhibit the spread or metastasis of the cancer into other tissues of the patients' body, especially including bones, the lymph (lymph nodes) system, bladder, vas deferens, kidneys, liver, lungs and brain, among others.

The present invention also relates to instances in which destruction of non-cancerous cells which possess PSMA can be of therapeutic use, especially in cancer therapy. For example, given that PSMA is found on the neovasculare of many non-prostatic cancer cells, but not on normal vasculature, the invention could be used for antiangiogenic therapy for other forms of cancer by targeting the neovasculature of those cancers and inhibiting the growth and spread of the cancer.

DETAILED DESCRIPTION OF THE INVENTION

The following terms are used to describe the present invention. In instances where a term is not specifically defined herein, that term is given an art-recognized meaning by those of ordinary skill applying that term in context to its use in describing the present invention.

The term "compound", as used herein, unless otherwise indicated, refers to any specific chemical compound, preferably SyAMs disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for the treatment of cancer, especially including prostate cancer and in particular, metastatic prostate cancer.

The term "effective" is used herein, unless otherwise indicated, to describe an amount of a compound or composition (one or more SyAMs alone or in combination) which, in context, is used to produce or effect an intended result, whether that result relates to the inhibition of the cancer or the treatment of a subject for secondary conditions, disease states or manifestations of cancer as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer, especially prostate cancer or metastasis of prostate cancer, including improvement in the condition through lessening or suppression of at least one symptom, inhibition of cancer growth, reduction in cancer cells or tissue, prevention or delay in progression of metastasis of the cancer, prevention or delay in the onset of disease states or conditions which occur secondary to cancer or remission or cure of the cancer, among others. Treatment, as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, which may be treated by one or more compounds according to the present invention. See, (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

Because of the activity of the present compounds as anti-angiogenic compounds, the present invention has general applicability treating virtually any cancer in any tissue, thus the compounds, compositions and methods of the present invention are generally applicable to the treatment of cancer. Given that the protein target is found on the neovasculature of most non-prostatic cancer cells, the compounds in the present invention may also serve as an antiangiogenic therapy for other cancer types. Most often, the compounds are used to treat prostate cancer, and metastatic prostate cancer, as well as reducing the likelihood that prostate cancer will not metastasize.

In certain particular aspects of the present invention, the cancer which is treated is prostate cancer or metastatic prostate cancer. Separately, metastatic prostate cancer may be found in virtually all tissues of a cancer patient in late stages of the disease, typically metastatic prostate cancer is found in seminal vesicles, lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology.

The term "tumor" is used to describe a malignant or benign growth or tumefacent.

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to the prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery and radiation therapy. Other treatments such as hormonal therapy, chemotherapy, proton therapy, cryosurgery, high intensity focused ultrasound (HIFU) also exist depending on the clinical scenario and desired outcome. The present invention may be used to enhance any one or more of these therapies or to supplant them.

The age and underlying health of the man, the extent of metastasis, appearance under the microscope, and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate or is metastatic. In the TNM system, clinical T1 and T2 cancers are found only in the prostate, while T3 and T4 cancers have spread elsewhere and metastasized into other tissue. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans often reveal osteoblastic appearance due to increased bone density in the areas of bone metastasis—opposite to what is found in many other cancers that metastasize. Computed tomography (CT) and magnetic resonance imaging (MRI) currently do not add any significant information in the assessment of possible lymph node metastases in patients with prostate cancer according to a meta-analysis.

Prostate cancer is relatively easy to treat if found early. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary dysfunction as the prostate gland surrounds the prostatic urethra. Changes within the gland therefore directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body and this may cause additional symptoms. The most common symptom is bone pain, often in the vertebrae (bones of the spine), pelvis or ribs. Spread of cancer into other bones such as the femur is usually to the proximal part of the bone. Prostate cancer in the spine can also compress the spinal cord, causing leg weakness and urinary and fecal incontinence.

The specific causes of prostate cancer remain unknown. A man's risk of developing prostate cancer is related to his age, genetics, race, diet, lifestyle, medications, and other factors. The primary risk factor is age. Prostate cancer is uncommon in men less than 45, but becomes more common with advancing age. The average age at the time of diagnosis is 70. However, many men never know they have prostate cancer.

A man's genetic background contributes to his risk of developing prostate cancer. This is suggested by an increased incidence of prostate cancer found in certain racial groups, in identical twins of men with prostate cancer, and in men with certain genes. Men who have a brother or father with prostate cancer have twice the usual risk of developing prostate cancer. Studies of twins in Scandinavia suggest that forty percent of prostate cancer risk can be explained by inherited factors. However, no single gene is responsible for prostate cancer; many different genes have been implicated. Two genes (BRCA1 and BRCA2) that are important risk factors for ovarian cancer and breast cancer in women have also been implicated in prostate cancer.

Dietary amounts of certain foods, vitamins, and minerals can contribute to prostate cancer risk. Dietary factors that may increase prostate cancer risk include low intake of vitamin E, the mineral selenium, green tea and vitamin D. A large study has implicated dairy, specifically low-fat milk and other dairy products to which vitamin A palmitate has been added. This form of synthetic vitamin A has been linked to prostate cancer because it reacts with zinc and protein to form an unabsorbable complex. Prostate cancer has also been linked to the inclusion of bovine somatotropin hormone in certain dairy products.

There are also some links between prostate cancer and medications, medical procedures, and medical conditions. Daily use of anti-inflammatory medicines such as aspirin, ibuprofen, or naproxen may decrease prostate cancer risk. Use of the cholesterol-lowering drugs known as the statins may also decrease prostate cancer risk. Infection or inflammation of the prostate (prostatitis) may increase the chance for prostate cancer, and infection with the sexually transmitted infections chlamydia, gonorrhea, or syphilis seems to increase risk. Obesity and elevated blood levels of testosterone may increase the risk for prostate cancer.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. This invasion of other organs is called metastasis. Prostate cancer most commonly metastasizes to the bones, lymph nodes, rectum, and bladder.

In prostate cancer, the regular glands of the normal prostate are replaced by irregular glands and clumps of cells. When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

After biopsy, the tissue samples are then examined under a microscope to determine whether cancer cells are present, and to evaluate the microscopic features (or Gleason score) of any cancer found. In addition, tissue samples may be stained for the presence of PSA and other tumor markers in order to determine the origin of malignant cells that have metastasized. A number of other potential approaches for diagnosis of prostate cancer are ongoing such as early prostate cancer antigen-2 (EPCA-2), and prostasome analysis.

In addition to therapy using the compounds according to the present invention, therapy (including prophylactic therapy) for prostate cancer supports roles in reducing prostate cancer for dietary selenium, vitamin E, lycopene, soy foods, vitamin D, green tea, omega-3 fatty acids and phytoestrogens. The selective estrogen receptor modulator drug toremifene has shown promise in early trials. Two medications which block the conversion of testosterone to dihydrotestosterone (and reduce the tendency toward cell growth), finasteride and dutasteride, are shown to be useful. The phytochemicals indole-3-carbinol and diindolylmethane, found in cruciferous vegetables (califlower and broccholi), have favorable antiandrogenic and immune modulating properties. Prostate cancer risk is decreased in a vegetarian diet.

Treatment for prostate cancer may involve active surveillance, surgery (prostatecomy or orchiectomy), radiation therapy including brachytherapy (prostate brachytherapy) and external beam radiation as well as hormonal therapy. There are several forms of hormonal therapy which include the following, each of which may be combined with compounds according to the present invention.

Antiandrogens such as flutamide, bicalutamide, nilutamide, and cyproterone acetate which directly block the actions of testosterone and DHT within prostate cancer cells.

Medications such as ketoconazole and aminoglutethimide which block the production of adrenal androgens such as DHEA. These medications are generally used only in combination with other methods that can block the 95% of androgens made by the testicles. These combined methods are called total androgen blockade (TAB), which can also be achieved using antiandrogens.

GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin.

The use of abiraterone acetate can be used to reduce PSA levels and tumor sizes in aggressive end-stage prostate cancer for as high as 70% of patients. Sorafenib may also be used to treat metastatic prostate cancer.

Each treatment described above has disadvantages which limit its use in certain circumstances. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. As noted above, abiraterone acetate shows some promise in treating advance stage prostate cancer as does sorafenib. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone-refractory metastatic prostate cancer. Alpharadin may be used to target bone metastasis. The phase 11 testing shows prolonged patient survival times, reduced pain and improved quality of life.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

As an alternative to active surveillance or definitive treatments, alternative therapies may also be used for the management of prostate cancer. PSA has been shown to be lowered in men with apparent localized prostate cancer using a vegan diet (fish allowed), regular exercise, and stress reduction. Many other single agents have been shown to reduce PSA, slow PSA doubling times, or have similar effects on secondary markers in men with localized cancer in short term trials, such as pomegranate juice or genistein, an isoflavone found in various legumes.

Manifestations or secondary conditions or effects of metastatic and advanced prostate cancer may include anemia, bone marrow suppression, weight loss, pathologic fractures, spinal cord compression, pain, hematuria, ureteral and/or bladder outlet obstruction, urinary retention, chronic renal failure, urinary incontinence, and symptoms related to bony or soft-tissue metastases, among others.

Additional prostate drugs which can be used in combination with the chimeric antibody recruiting compounds according to the present invention include, for example, the enlarged prostate drugs/agents, as well as eulexin, flutamide, goserelin, leuprolide, lupron, nilandron, nilutamide, zoladex and mixtures thereof. Enlarged prostate drugs/agents as above, include for example, ambenyl, ambophen, amgenal, atrosept, bromanyl, bromodiphenhydramine-codeine, bromotuss-codeine, cardura, chlorpheniramine-hydrocodone, ciclopirox, clotrimazole-betamethasone, dolsed, dutasteride, finasteride, flomax, gecil, hexalol, lamisil, lanased, loprox, lotrisone, methenamine, methen-bella-meth Bl-phen sal, meth-hyos-atrp-M blue-BA-phsal, MHP-A, mybanil, prosed/DS, Ro-Sed, S-T Forte, tamsulosin, terbinafine, trac, tussionex, ty-methate, uramine, uratin, uretron, uridon, uroves, urstat, usept and mixtures thereof.

The term "Immune binding terminal moiety", "Immune binding terminus", or [IBT] is use to described that portion of a chimeric compound according to the present invention which comprises a molecule which binds to FcγRI.receptor on an immune effector cell (macrophage, neutrophil, eosinophil, dendritic cell, etc.) and facilitates opsonization, phagocytosis, cytotoxicity and the death of cancer cells. A preferred FcRI binding moiety for use in the present invention is CP33, presented in attached FIG. 2.

Figure 14:
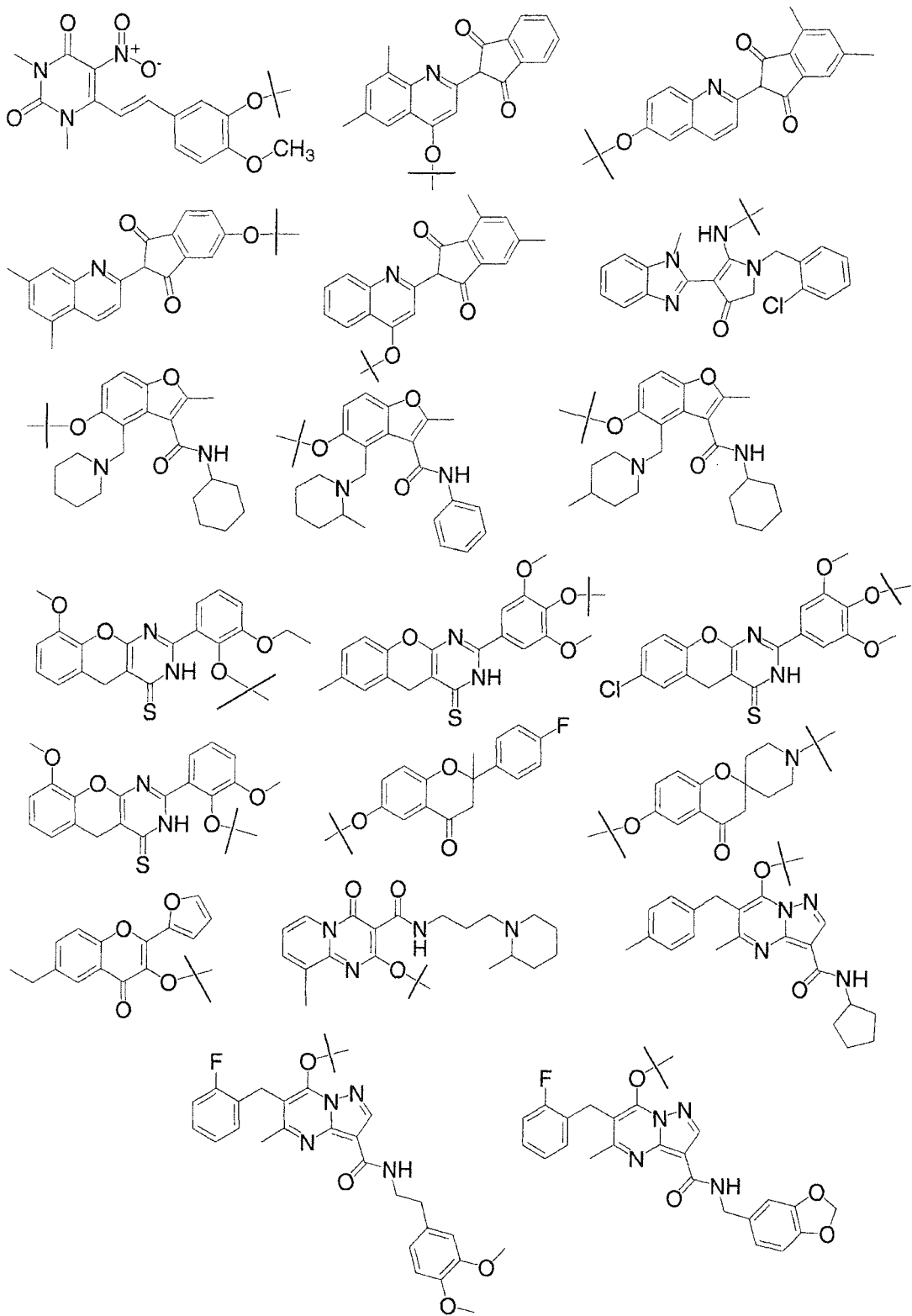
FIG. 14 shows a number of Fc receptor binding moieties which exhibit activity as modulators of FcγRI and can be used as an [IBT] group pursuant to the present invention. In the figure, each of the compounds is shown with an attachment bond at a free hydroxyl (OH group) or amine (NH2).
Figure 14:
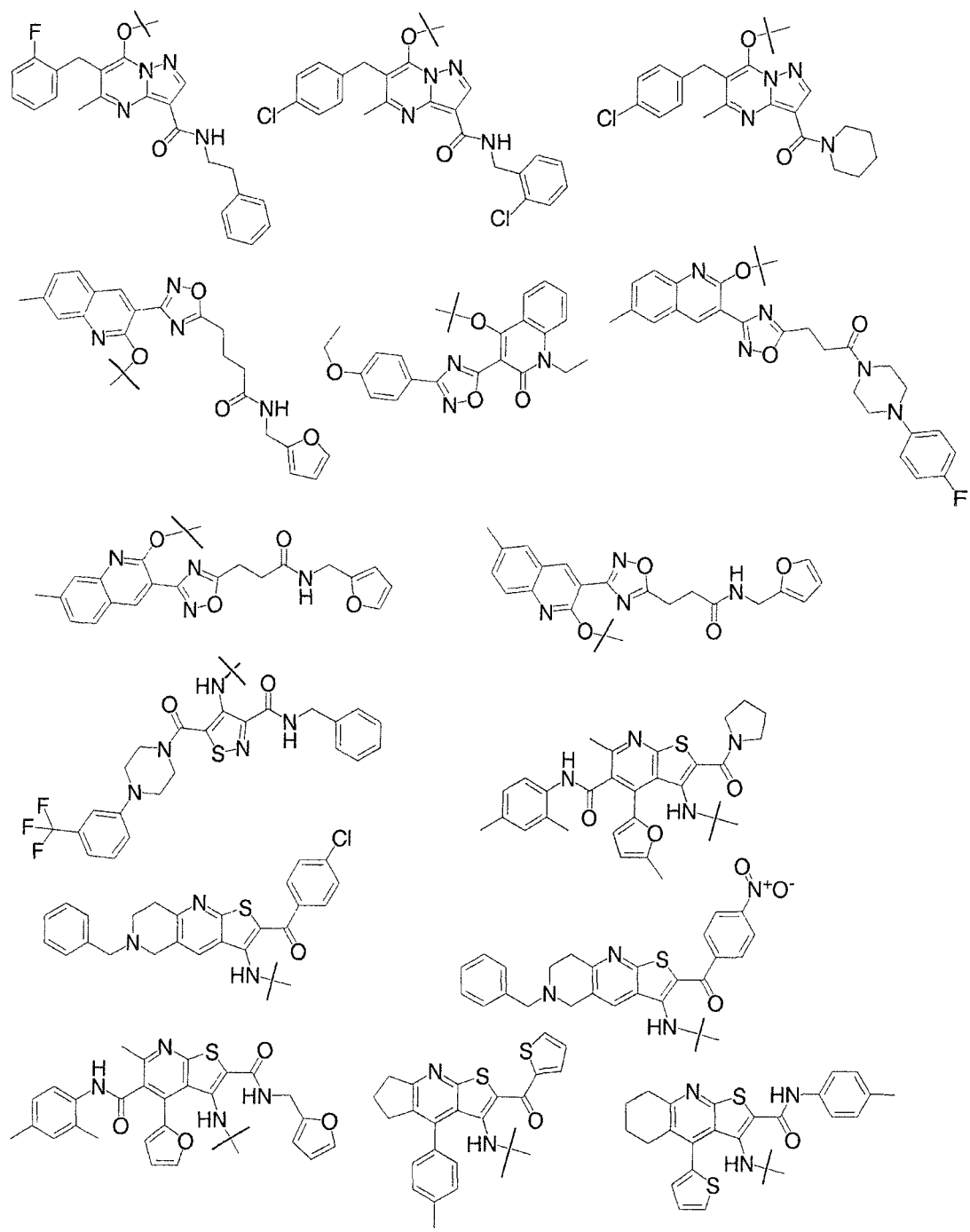
Figure 14:
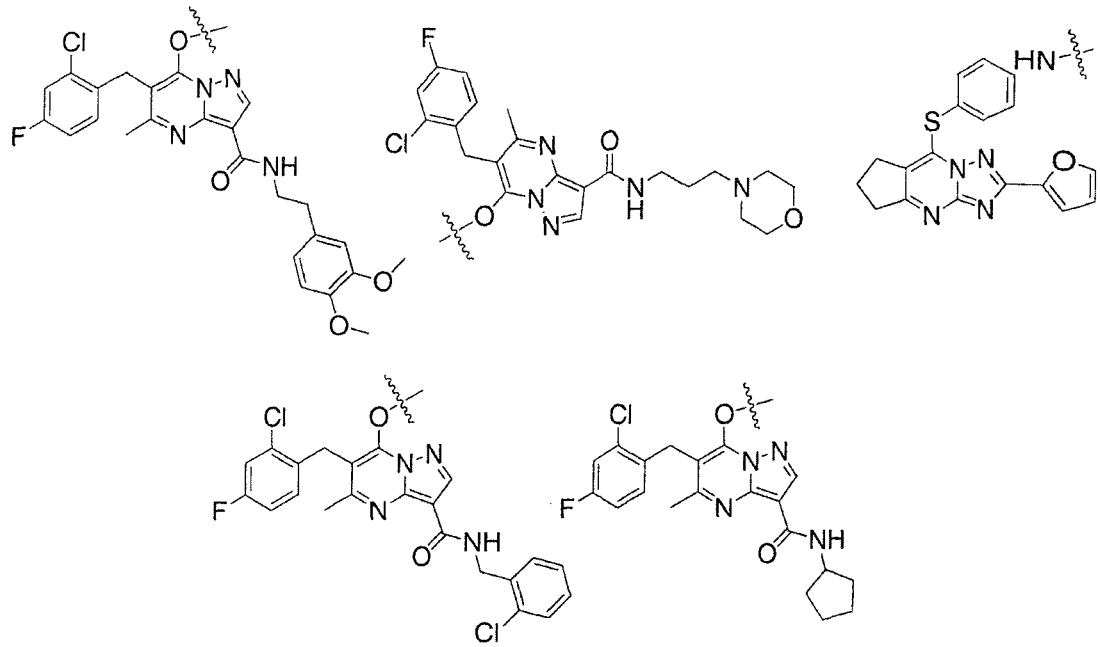
Figure 14:
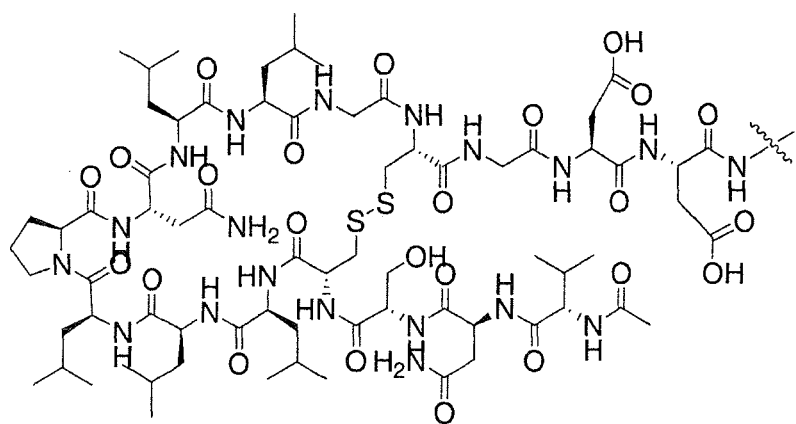

Representative [IBT] groups for use in the present invention include those which appear in attached FIG. 14. Each of these compounds can be used to modulate FcγRI receptors which interact with immune effector cells (macrophages, eosinophils, neutrophils) to induce phagocytic and other activity by these effector cells against cancer cells as otherwise described herein. In addition, these compounds may also provide an ability to induce a long-term immune response to cancer cells in a patient, thus reducing the likelihood of a recurrence after cancer remission.

Representative [IBT] groups include for example, CP33 (a preferred IBT), YU158145 (4861-0063), YU160469 (7165-0402), YU160642 (7527-0236), YU160645 (7527-0311), YU160647 (7527-0320), YU164313 (D086-0504), YU164340 (D089-0267), YU164343 (D089-0287), YU164367 (D089-0353), YU163512 (C766-0140), YU163538 (C766-0571), YU163540 (C766-0578), YU163511 (C766-0135), YU163552 (C798-0145), YU163554 (C798-0169), YU160794 (7889-2431), YU163387 (C720-0562), YU163388 (C720-0563), YU162384 (C218-0192), YU162389 (C218-0271), YU162392 (C218-0284), YU162393 (C218-0288), YU162402 (C218-0460), YU162408 (C218-0524), YU165568 (D420-6099), P680-0123 (YU170286:01), YU165561 (D420-5349), YU165531 (D420-4922), YU165550 (D420-5220), YU169577 (M050-0297), YU162636 (C291-0121), YU163100 (C611-0416), YU163102 (C611-0421), YU162257 (C200-0357), YU169182 (K891-0143), YU169197 (K891-0201), YU162415 (C218-0870), YU162417 (C218-0879), YU162413 (C218-0864), YU162414 (C218-0868) and YU162730 (C301-9341), which are modified at a free hydroxyl or free amine to link to other components of the compounds according to the present invention. Each of these immune modulating compounds is presented as a chemical structure in FIG. 14 with attachment indicated at a free hydroxyl or free amine of the compound. Attachment on each of these molecules to a linker and the rest of the molecules according to the present invention is on a free hydroxyl or a free amine, as represented in FIG. 14 (bond intersecting another bond at O or N in each compound, accordingly). The [IBT] most often used in the present invention is CP33, because it has shown the greater activity as a modulator of FcγRI. CP33 is also represented in FIG. 14.

The term "cell binding terminal moiety", "cell binding terminus" or "cell binding moiety" is use to described that portion of a chimeric compound according to the present invention which comprises at least one small molecule or moiety which can bind specifically to prostate specific membrane antigen (PSMA).

Preferred CBT groups for use in the present invention are set forth below:

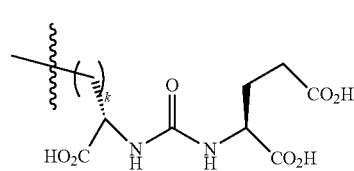

-continued

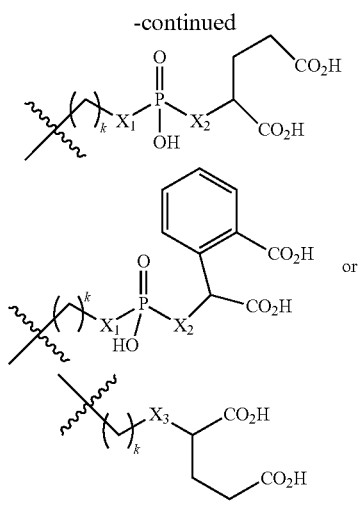

Where $X_1$ and $X_2$ are each independently $CH_2$, O, NH or S;

$X_3$ is O, $CH_2$, $NR^1$, S(O), S(O)$_2$, —S(O)$_2$O, —OS(O)$_2$, or OS(O)$_2$O;

$R^1$ is H, a $C_1$-$C_3$ alkyl group, or a —C(O)($C_1$-$C_3$) group;

k is an integer from 0 to 20, 8 to 12, 1 to 15, 1 to 10, 1 to 8, 1 to 6, 1, 2, 3, 4, 5 or 6;

or a salt or enantiomer thereof.

A preferred CBT group for use in the present invention is the group

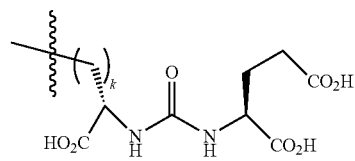

Where k is 2, 3 or 4, preferably 3. This CBT group, as well as the others, optionally has an amine group or other functional group at the distill end of the alkylene group (k) such that k is formed from, for example, a lysine amino acid, such that the amine group or other functional group may participate in further reactions to form a linker, a triazole or other difunctional connector group [CON] or a multifunctional group [MULTICON] as otherwise described herein.

The term "linker" refers to a chemical entity which connects the cell binding terminus moiety [CBT] or immune (Fc receptor) binding terminus [IBT] to the difunctional connector moiety moiety/molecule [CON] and/or the multifunctional conector moiety/molecule [MULTICON]. It is noted that each linker may be connected to [MULTICON} through an optional difunctional connector molecule [CON} as otherwise disclosed here. The linker is non-labile and also may be comprised of one or more linker groups to provide extended linkers as otherwise disclosed herein. Each linker may be directly linked to a [CBT] or an [IBT] group especially between the [ABT] moiety and the multifunctional connector molecule [MULTICON} and the [CBT] moiety and the multifunctional connector molecule [MULTICON]. In certain instances, the CBT group may be linked directly to a difunctional connector group [CON] which is further linked to a linker group and optionally, a [MULTICON] group. The linker between the two active functional portions of the molecule, i.e., the immune binding terminus [IBT] and the cell binding terminus [CBT] ranges from about 5 Å to about 50 Å or more in length, about 6 Å to about 45 Å in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon unnatural amino acids (i.e., having an alkylene group with between 3 and 6, preferably 4 or 5 methylene groups between the amine and acid of the amino acid monomeric unit) as otherwise described herein often used. By having a linker with a length as otherwise disclosed herein, the one or more [IBT] moieties and the one or more [CBT] moieties may be situated to take advantage of the biological activity of compounds according to the present invention which bind to prostate specific membrane antigen (PSMA) through the [CBT] group and modulate Fc receptors, in particular, FcγRI receptors on immune effector molecules through the [IBT] group functioning synergistically with the [CBT] group unit to improve the compound's ability to modulate tumor lysis (e.g. phagocytosis) by immune effector cells and better stimulate and promote immunologic memory to which the compounds are bound. This results in the selective and targeted (synergistic) cell death of cancer cells, including metastatic cancer cells, in particular, prostate cancer cells and metastatic prostrate cancer cells, in whatever tissues they may reside. The selection of a linker component is based on its documented properties of biocompatibility, solubility in aqueous and organic media, and low immunogenicity/antigenicity.

Linkers which are based upon or include oligo amino acid units are preferred for use in the present invention. These preferred linkers are between 2 and 100 amino acid units in length, but those which are between 2 and 14 amino acid units or 4 to 8 amino acid units in length may be preferred. In preferred aspects, each amino acid unit is an unnatural amino acid unit as otherwise described herein, preferably having between 3 and 6 methylene group in each amino acid monomeric unit. Each linker may be linked with the multifunctional connector molecule [MULTICON] through one or more difunctional conector molecules [CON] as otherwise disclosed herein.

Although numerous linkers may be used as otherwise described herein, a linker (non-labile) based upon polyethyleneglycol (PEG) linkages, polypropylene glycol linkages, or polyethyleneglycol-co-polypropylene glycol polymers (e.g., block copolymers where the polyethylene glycol portion of the block is from 1 to 12 polyethylene glycol units in length and said polypropylene glycol portion of the block is from 1 to 12 polypropylene glycol units in length, the total number of polyethylene glycol units, polypropylene glycol units or polyethyleneglycol-co-polypropyleneglycol block copolymer units being from 1 to 100, 1 to 75, 1 to, 1 to 15, 1 to 12, 1, 2, 3, 4, 5, 6, 7, 8, 9, 10, 11 or 12 or often up to about 100 units, about 1 to 100, about 1 to 75, about 1 to 60, about 1 to 50, about 1 to 35, about 1 to 25, about 1 to 20, about 1 to 15, 1 to 10, about 8 to 12, about 1 to 8. Of these, polyethylene (PEG) linkages are more often used.

Alternative preferred linkers may include, for example, polyproline linkers and/or collagen linkers as depicted below (n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

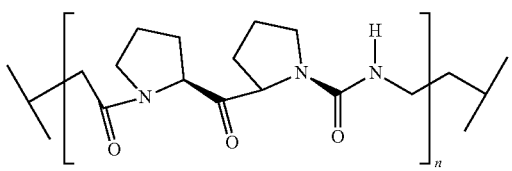

polyproline linker
or

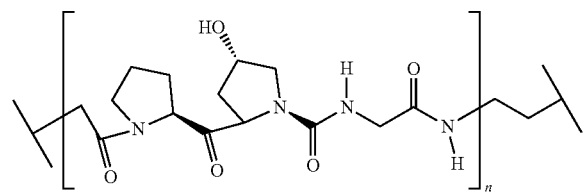

collagen linker.

Additional linkers include those according to the chemical structures:

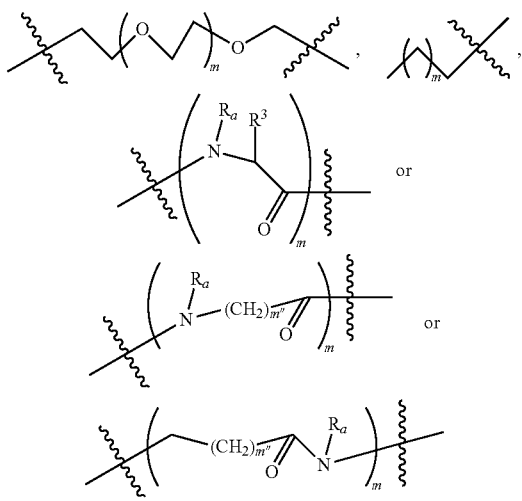

Where $R_a$ is H, $C_1$-$C_3$ alkyl or alkanol or forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m" is an integer between 0 to 25, preferably 1 to 10, 1 to 8, 1, 2, 3, 4, 5, or 6;

m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units which may be further linked through amide groups (which include alkylene groups on either or both sides of the amide group containing one to five methylene units), keto groups (which include alkylene keto groups containing one to five methylene units), amine groups (which include alkylene amine groups containing one to five methylene units), alkylene groups (containing from 1 to 5 methylene units), amino acids or other moieties compatible with polyethylene glycol groups, including difunctional connecting groups [CON]), [CBT] groups, [IBT] groups, [MULTICON] groups and other linker groups including other polyethylene glycol groups (often with anywhere between 1 and 12 ethylene glycol units (e.g. 1, 2, 3, 4, 5, 6, 7, 8, 9, 10, 11, 12). Still other linkers comprise polypeptides of amino acid residues (D or L). In another embodiment, as otherwise described herein, polypeptides may comprise non-naturally occurring amino acids (non-naturally occurring except for glycine) of the non-labile linker each of which has anywhere from 1-15 or more methylene groups separating the amino group from the acid group, often from three to six methylene groups (3, 4, 5 or 6), and from 1 to 100 peptide groups in providing a linker to the moiety, preferably 1 to 12 (1, 2, 3, 4, 5, 6, 7, 8, 9, 10, 11 or 12). It is noted that each of the polypeptide linkers and other linkers (including labile linkers) identified in the present application may be further linked together or with connector molecules/moieties [CON], [MULTICON] molecules/moieties, [IBT] groups, and/or [CBT] groups through amide groups (which include alkylene groups on either or both sides of the amide group containing one to five methylene units), keto groups (which include alkylene keto groups containing one to five methylene units on either or both sides of the keto group), amine groups (which include alkylene amine groups containing one to five methylene units on either or both sides of the amine group), urethane groups (which include alkylene groups containing one to five methylene units on either or both sides of the urethane moiety) alkylene groups (containing from 1 to 5 methylene units), amino acids or other moieties compatible with the linker chemistry in order to link components of the molecules. It is noted that in the case of polyethylene glycol and polypeptide linkers, the use of an additional group (eg, alkylene amine or other group as described above) or a second linker group may be useful for joining the linker to another component of the molecule. Additionally, more than one linker group identified herein may be linked together to form a linker group as otherwise used in the present compounds, consistent with the stability of the linker chemistries. These extended linkers are often linked through [CON} connecting groups or as otherwise described herein.

Additional preferred linkers include those according to the structure:

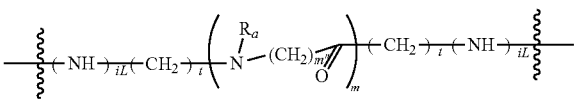

where $R_a$ is H or a $C_1$-$C_3$ alkyl, preferably $CH_3$, most often H;

m is an integer from 1 to 12, often 1, 2, 3, 4, 5, or 6;

m" is an integer 1, 2, 3, 4, 5, or 6, often 6;

t is 0, 1, 2, 3, 4, 5, or 6; and iL is 0 or 1, often 1, wherein said linker in certain instances, may be preferably linked to a [CON] group and a [CBT] group at one end and a [MULTICON] group on the other end; or a linker according to the structure:

Where a is an integer from 0-12, preferably 1, 2, 3, 4, 5 or 6; and q' is 1 to 12, often 1, 2, 3, 4, 5 or 6.

The two above linkers may be linked together to provide further linkers which are often used in compounds according to the present invention:

Where q is an integer from 0-12, preferably 0, 1, 2, 3, 4, 5 or 6;

q' is 1 to 12, often 1, 2, 3, 4, 5 or 6;

iL is 0 or 1; and $R_L$ is an amino acid or an oligopeptide (which term includes a dipeptide) as otherwise described herein, especially including lysine, dilysine, or glycinelysine.

Another linker according to the present invention includes a linker based upon succinimide according to the chemical formula:

where each $X^S$ is independently S, O or N—$R^S$, preferably S;

$R^S$ is H or $C_{1-3}$ alkyl, preferably H;

$S_c$ is $CH_2$; $CH_2O$; or $CH_2CH_2O$;

i is 0 or 1; and $m^S$ is 0, 1, 2, 3, 4, 5, or 6.

Other linkers which may be used in the present invention include linkers according to the chemical formula:

Where Z and Z' are each independently a bond, —$(CH_2)_i$—O, —$(CH_2)_i$—S, —$(CH_2)_i$—N—R, wherein said Z or Z' group is optionally bonded to another linker group, a connector [CON], a [MULTICON] group, IBT or CBT;

Each R is H, or a $C_1$-$C_3$ alkyl or alkanol group;

Each $R^2$ is independently H or a $C_1$-$C_3$ alkyl group;

Each Y is independently a bond, O, S or N—R;

Each i is independently 0 to 100, preferably 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 0, 1, 2, 3, 4 or 5;

D is or a bond, or D may be

-continued

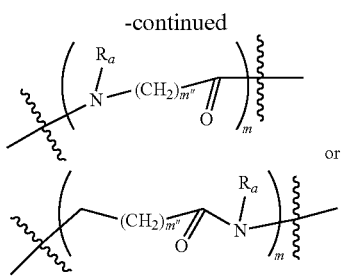

or or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);

with the proviso that Z, Z' and D are not each simultaneously bonds;

each i is the same as above;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m" is an integer between 0 to 25, preferably 1 to 10, 1 to 8, 1, 2, 3, 4, 5, or 6;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R;

R is as described above;

$R_a$ is H, $C_1$-$C_3$ alkyl or alkanol or forms a cyclic ring with $R^3$ (proline); and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl), wherein said sidechain of said amino acid (often lysine) is optionally linked or a pharmaceutically acceptable salt thereof. In certain embodiments, the amino acid may be linked through the sidechain of the amino acid. In certain embodiments, the amino acid is often lysine because of its trifunctionality wherein the amine of the sidechain is used to link other linkers and/or other components of the molecule. It is noted that an amino acid which has trifunctionality and the sidechain is used to create the linker, the amino acid (often lysine) may be end-capped at the carboxylic acid with an amine group which is optionally substituted with a $C_1$-$C_{12}$ alkyl group, preferably a $C_1$-$C_3$ alkyl group) or at the amine terminus with an acyl group.

It is noted that for each linker, one or more of the linking groups as depicted herein may be extended through binding with one or more difunctional connector group [CON], which is described in greater detail hereinbelow. For example, a polyethylene glycol linker (e.g. from 1 to 12 ethylene glycol units, 1, 2, 3, 4, 5, 6, 7, 8, 9, 10, 11 or 12) extended to one or more polyethylene glycol linker(s) (e.g. each linker being from 1 to 12 ethylene glycol units, 1, 2, 3, 4, 5, 6, 7, 8, 9, 10, 11 or 12) through one or more [CON[ groups as otherwise described herein, including an amide [CON] group(s) represents additional embodiments of the present invention.

As discussed, certain preferred linkers for use in the present invention include a linker group as shown in compounds 1, 2 or 3 of FIG. 2 which often links a [CBT] moiety to a [MULTICON] molecule according to the chemical structure.

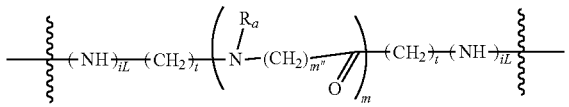

where $R_a$ is H or $CH_3$, most often H;

m is an integer from 1 to 12, often 1, 2, 3, 4, 5, or 6;

m" is an integer 1, 2, 3, 4, 5, or 6, often 6;

t is 0, 1, 2, 3, 4, 5, or 6; and iL is 0 or 1, often 1, wherein L may be optionally linked to a [CON] group and a [CBT] group at one end and a [MULTICON] group on the other end; or As described above, alternatively, often L is a complex linker group (as depicted in compound 3 of FIG. 2) which is made up of an ethylene oxide containing amine group

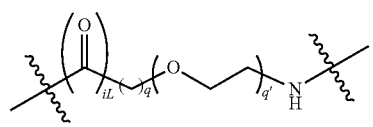

where q is 0 to 12, 1, 2, 3, 4, 5 or 6;

q' is 1 to 12, often 1, 2, 3, 4, 5 or 6, iL is 0 or 1 wherein the keto group is linked to an amino acid group or to an oligopeptide (including a dipeptide) and the amine group is optionally linked through a diketo group (often to [IBT], more often CP33),

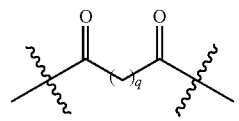

where q is the same as above, and an amino acid, often lysine, or an amino acid dipeptide, often dilysine. In preferred aspects, one of the lysines of the dipeptide is directly bonded to CP33, and another amino acid (often lysine) links the above ethylene oxide amine group to a [MULTICON] group through a [CON] group, most often a triazole. The chemical structure of the complex linker described above may be represented by the chemical structure:

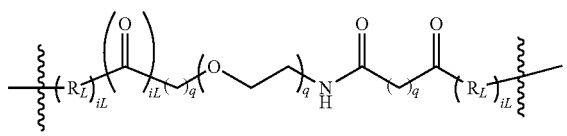

Where q is an integer from 0-12, preferably 0, 1, 2, 3, 4, 5 or 6;
q' is 1 to 12, often 1, 2, 3, 4, 5 or 6;
iL is 0 or 1; and
$R_L$ is an amino acid or an oligopeptide (which term includes a dipeptide) as otherwise described herein, especially including lysine, dilysine, or glycinelysine.

In certain additional embodiments, the linker group L is an amino acid, a dipeptide or an oligopeptide containing from 1 to 12, preferably 1 to 6 amino acid monomers or more. In certain embodiments, the oligopeptide is a dipeptide and the dipeptide is a dilysine or a glycinelysine dipeptide. When lysine is used as an amino acid in an oligopeptide linker, the sidechain alkylene amine is often used to link other linker groups or other components in the molecule.

The term "multifunctional connector", symbolized by [MULTICON], is used to describe a chemical group or molecule which is optionally included in chimeric compounds according to the present invention which forms from the reaction product of an activated IBT-linker with a CBT moiety (which also is preferably activated) or an IBT moiety with an activated linker-CBT as otherwise described herein. Numerous other synthetic approaches are possible. The synthetic chemistry used to synthesize compounds according to the present invention is presented in detail herein. The connector group is the resulting moiety which forms from the facile condensation of at least three separate chemical fragments which contain reactive groups which can provide connector groups as otherwise described to produce chimeric compounds according to the present invention. It is noted that a multifunctional connector moiety or molecule [MULTICON] is readily distinguishable from a linker in that the multifunctional connector is the result of a specific chemistry which is used provide chimeric compounds according to the present invention.

Connecting moieties in the present invention include at least one multifunctional moiety or molecule [MULTICON] which contains three or more functional groups which may be used to covalently bind (preferably, through a linker) to at least one [IBT] group and at least one [CBT] group, thus linking each of these functional groups into a single compound. Multifunctional connector groups for use in the present invention include moities which have at least three or more functional groups which can bind to linkers to which are bound [IBT] and [CBT] groups in order to provide compounds which contain at least one and preferably more than one [IBT] and [CBT] pursuant to the present invention. These multifunctional connector moieties may also bind to other multifunctional connector molecules in order to create compounds containing a number of [IBT] and [CBT] groups as defined herein.

Multifunctional connector molecules [MULTICON] comprise any molecule or moiety which contains at least three groups which may be linked to [IBT] and [CBT] groups, linkers and/or other connector groups (including difunctional and multifunctional connector groups) and preferably comprise five or six-membered aryl or heteroaryl groups (especially six-membered ring groups) exemplified by multifunctional, especially trifunctional or tetrafunctional aryl or heteroaryl groups, including phenyl, pyridyl, pyrimidinyl, 1,3,5-triazinyl, 1,2,3-triazinyl, 1,2,4-triazinyl groups, each of which is substituted with at least 3 and up to 6 functional groups or other groups as defined herein. These functional groups may be derived from nucleophilic or electrophilic groups on the multifunctional connector molecule precursor (the multifunctional connector molecule which forms the [MULTICON] moiety in final compounds according to the present invention) which are condensed onto linker groups (containing, for example an [IBT] group and a [CBT] group which contain a group which can be linked to the [MULTICON] moiety. [MULTICON] groups which are used in the present invention preferably include substituted phenyl, pyridyl, pyrimidinyl and 1,3,5-triazinyl, 1,2,3-triazinyl, 1,2, 4-triazinyl groups, especially groups according to the chemical structure:

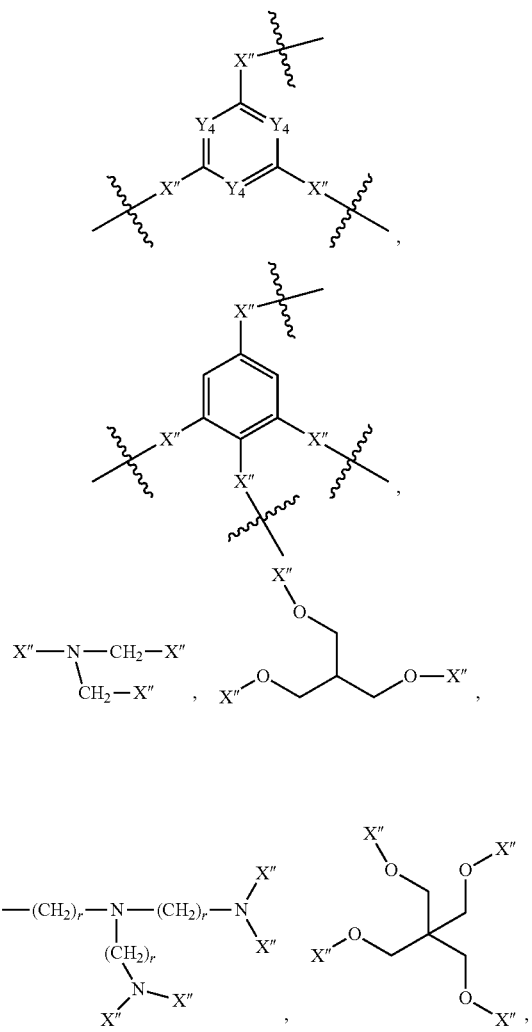

-continued

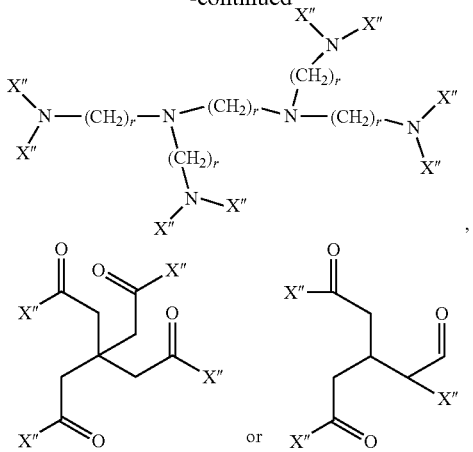

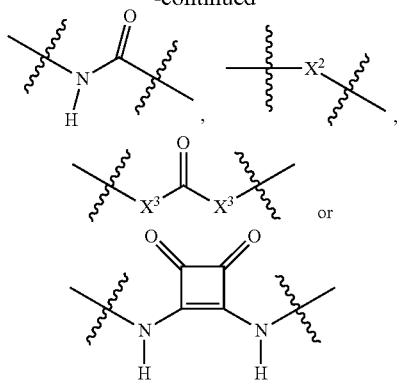

where $Y_4$ is C—H or N; and
Each X" is independently derived from an electrophilic or nucleophilic group, preferably $(CH_2)_{n''}O$, $(CH_2)_{n''}N^{RCON}$, $(CH_2)_{n''}S$, $(CH_2)_{n''}$ or $(CH_2)_{n''}C=O$ or when said [MULTICON] group is a ring structure, X" is optionally a [CON] group, often a triazole group, linked to the ring structure, often directly to the ring structure;
the substitutent RCON is H or a $C_1$-$C_3$ alkyl, preferably H or $CH_3$ and
n" is 0, 1, 2 or 3, and
r is an integer from 1-12, often, 1, 2, 3, 4, 5, or 6.

The term "difunctional connector group" or [CON] is used to describe a difunctional group which connects two (or more) portions of a linker group to extend the length of the linker group. In certain embodiments, a linker group is reacted with or forms a [CON] group with another linker group to form an extended linker group. The reaction product of these groups results in an identifiable connector group [CON] which is distinguishable from the linker group as otherwise described herein. It is further noted that there may be some overlap between the description of the difunctional connector group and the linker group, especially with respect to more common connector groups such as amide groups, oxygen (ether), sulfur (thioether) or amine linkages, urea or carbonate —OC(O)O— groups as otherwise described herein. It is noted that a difunctional connector molecule [CON] used hereunder is often connected to two parts of a linker group which binds [IBT] and [CBT] to the multifunctional connector molecule [MULTICON]. Alternatively, a [CON] group may be directly linked to a [IBT] group or more often, a [CBT] group, as well as a [MULTICON] group as described herein.

Common difunctional connector groups [CON] which are used in the present invention, principally to link one end of a linker to another end of a linker to provide a longer linker include the following chemical groups:

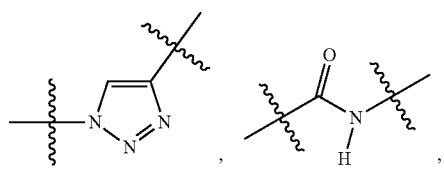

Where $X^2$ is O, S, $NR^4$, S(O), $S(O)_2$, —$S(O)_2O$, —$OS(O)_2$, or $OS(O)_2O$,
$X^1$ is O, S, $NR^4$; and
$R^4$ is H, a $C_1$-$C_3$ alkyl or alkanol group, or a —$C(O)(C_1$-$C_3)$ group.
In embodiments, [CON] is often a

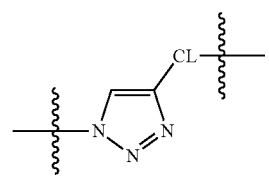

group;
where CL is

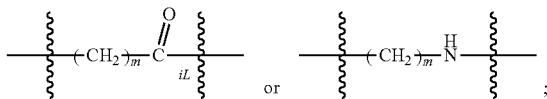

m in CL is an integer from 0 to 12, often 0, 1, 2, 3, 4, 5 or 6;
and iL is 0 or 1, often 1;
In certain embodiments, this [CON] group is often linked through the amine of the triazole to the ring structure of [MULTICON].

As discussed hereinabove, it is noted that each of the [ABT] and [CBT] functional groups may be further linked to a chemical moiety which bonds two or more of the above connector/multiconnector groups into a larger multifunctional connector, thus providing complex multifunctional compounds comprising more than one [IBT] and [CBT] groups within the multifunctional compound.

The term "end-cap" or "end-capping" is used to describe a non-reactive chemical moiety which is bonded to a free carboxylic acid group or a free amine group in an amino acid which is often used as a linker in compounds according to the present invention. Preferred end-capping groups for carboxylic acids in the present invention are amine groups which are optionally substituted with a $C_1$-$C_{12}$ alkyl group, preferably a $C_1$-$C_3$ alkyl group. By forming an amide with the active carboxylic acid, the carboxylic acid becomes a stable non-reactive moiety in the present compounds. In the case of amine groups, these are end-capped preferably with acyl groups or urethane groups, preferably acyl groups to form stable, unreactive amides.

The term "acyl" is used to describe a group according to the chemical structure which often contains a $C_1$ to $C_{20}$, often a $C_2$ to $C_{20}$, linear, branched or cyclic alkyl chain linked to a keto group, thus forming an unreactive amide with a free amine in compounds according to the present invention. The acyl group on the free amine (often of an amino acid used in linkers in compounds according to the present invention results in an stable, unreactive amide (although the amide may be cleave after administration of compounds according to the present invention, thus providing, in certain instances, prodrug embodiments of compounds according to the present invention. Acyl groups according to the present invention may be represented by the structure:

where $R_4$ is a $C_1$ to $C_{20}$ linear, branched or cyclic alkyl group, alkoxyalkyl, aryloxyalkyl, such as phenoxymethyl, aryl, alkoxy, among others. Preferred acyl groups are those where $R_4$ is a $C_1$ to $C_{10}$ alkyl group. Acyl groups according to the present invention also include, for example, those acyl groups derived from benzoic acid and related acids, such as substituted benzoic acid, succinic, capric and caproic, lauric, myristic, palmitic, stearic and oleic groups, among numerous others. One of ordinary skill in the art will recognize the acyl groups which will have utility in the present invention, either to end-cap reactive amine groups to produce unreactive, stable amides or, in certain embodiments, as prodrug forms of the compounds according to the present invention.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol). Specific anticancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

In addition to anticancer agents, a number of other agents may be coadministered with chimeric compounds according to the present invention in the treatment of cancer, especially prostate cancer, including metastatic prostate cancer. These include active agents, minerals, vitamins and nutritional supplements which have shown some efficacy in inhibiting prostate cancer tissue or its growth or are otherwise useful in the treatment of prostate cancer. For example, one or more of dietary selenium, vitamin E, lycopene, soy foods, vitamin D, green tea, omega-3 fatty acids and phytoestrogens, including beta-sitosterol, may be utilized in combination with the present compounds to treat prostate cancer.

In addition, active agents, other than traditional anticancer agents have shown some utility in treating prostate cancer. The selective estrogen receptor modulator drug toremifene may be used in combination with the present compounds to treat cancer, especially prostate cancer, including metastatic prostate cancer. In addition, two medications which block the conversion of testosterone to dihydrotestosterone, finasteride and dutasteride, are also useful in the treatment of prostate cancer when coadministered with compounds according to the present invention. The phytochemicals indole-3-carbinol and diindolylmethane, may also be coadministered with the present compounds for their effects in treating prostate cancer. Additional agents which may be combined with compounds according to the present invention include antiandrogens, for example, flutamide, bicalutamide, nilutamide, and cyproterone acetate as well as agents which reduce the production of adrenal androgens (e.g. DHEA), such as ketoconazole and aminoglutethimide. Other active agents which may be combined with compounds according to the present invention include, for example, GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin, among others. These agents may be combined with compounds according to the present invention in effective amounts. In addition, abiraterone acetate may also be combined with one or more compounds according to the present invention in the treatment of prostate cancer, especially including metastatic prostate cancer.

Other agents which may be combined with one or more compounds according to the present invention, include the bisphosphonates such as zoledronic acid, which have been shown to delay skeletal complications such as fractures which occur with patients having metastatic prostate cancer. Alpharadin, another agent, may be combined with compounds according to the present invention to target bone metastasis. In addition, bone pain due to metastatic prostate cancer may be treated with opioid pain relievers such as morphine and oxycodone, among others, which may be combined with compounds according to the present invention.

The present invention preferably relates to compounds according to the general chemical structure:

Wherein n and n' are each independently an integer from 1 to 15, often 2 to 10, often 2 to 5, more often 2 or 3;
NL1 and NL2 are each an integer from 0 to 10, often 1 to 10, often 2 to 5, more often 2 or 3, with the proviso that n≥NL1 and n'≥NL2;
MCON is an integer from 0 to 10, often 1 to 10, more often 1 to 5, often 0, 1 or 2;
[IBT] is an immune binding moiety according to the chemical formula set forth in FIG. 14 hereof, preferably, [IBT] is a CP33 group according to the chemical structure:

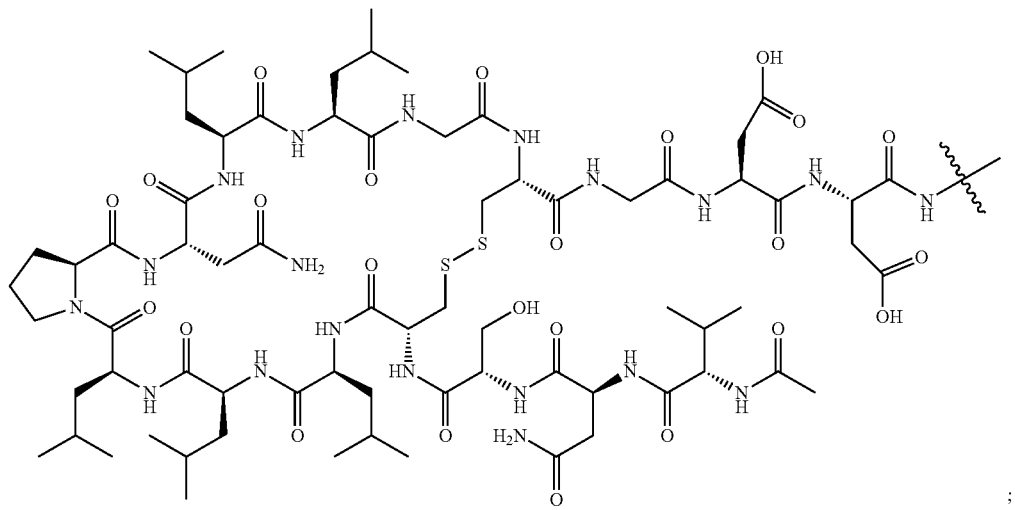 [SMILES: *NC(=O)[C@H](CC(=O)O)NC(=O)[C@H](CC(=O)O)NC(=O)CNC(=O)[C@@H]1CSSC[C@H](NC(=O)[C@H](CO)NC(=O)[C@H](CC(N)=O)NC(=O)[C@@H](NC(C)=O)C(C)C)C(=O)N[C@@H](CC(C)C)C(=O)N[C@@H](CC(C)C)C(=O)N[C@@H](CC(C)C)C(=O)N2CCC[C@H]2C(=O)N[C@@H](CC(N)=O)C(=O)N[C@@H](CC(C)C)C(=O)N[C@@H](CC(C)C)C(=O)NCC(=O)N1]

;

[CBT] is a cell binding moiety according to the chemical formula:

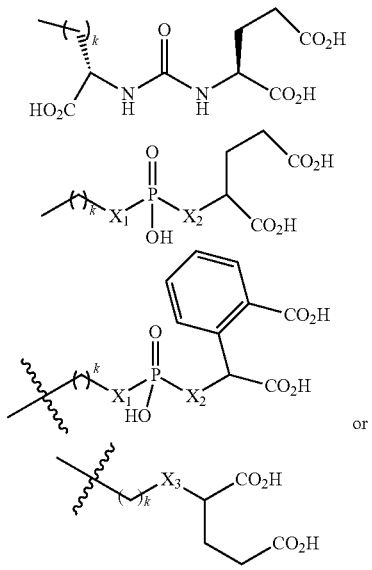

or

Where $X_1$ and $X_2$ are each independently $CH_2$, O, NH or S;
$X_3$ is O, $CH_2$, $NR^4$, S(O), $S(O)_2$, $-S(O)_2O$, $-OS(O)_2$, or $OS(O)_2O$;
$R^1$ is H, a $C_1$-$C_3$ alkyl group, or a $-C(O)(C_1$-$C_3)$ group;
k is an integer from 0 to 20, 8 to 12, 1 to 15, 1 to 10, 1 to 8, 1 to 6, 1, 2, 3, 4, 5 or 6;

$L_1$ and $L_2$ are each independently a linker according to the chemical formula:

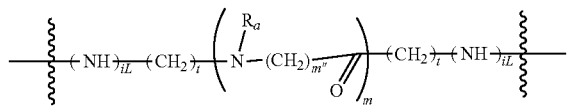

where $R_a$ is H or a $C_1$-$C_3$ alkyl, preferably $CH_3$, most often H;

m is an integer from 1 to 12, often 1, 2, 3, 4, 5, or 6;

m" is an integer 1, 2, 3, 4, 5, or 6, often 6;

t is 0, 1, 2, 3, 4, 5, or 6; and iL is 0 or 1, often 1, wherein said linker in certain instances, may be preferably linked to a [CON] group and a [CBT] group at one end and a [MULTICON] group on the other end; or a linker according to the structure:

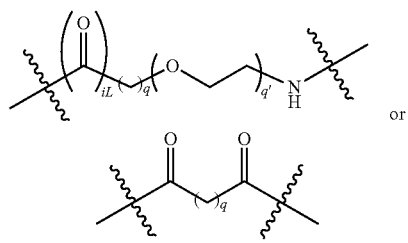

Where q is an integer from 0-12, preferably 1, 2, 3, 4, 5 or 6;

q' is 1 to 12, often 1, 2, 3, 4, 5 or 6 and iL is 0 or 1, preferably 1.

The two above linkers may be linked together to provide further linkers which are often used in compounds according to the present invention:

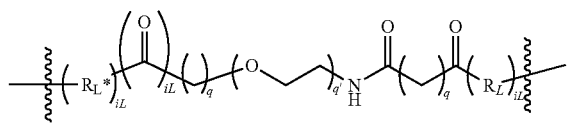

Where q is an integer from 0-12, preferably 0, 1, 2, 3, 4, 5 or 6;

q' is 1 to 12, often 1, 2, 3, 4, 5 or 6;

iL is 0 or 1; and $R_L$ is an amino acid or an oligopeptide (which term includes a dipeptide) as otherwise described herein, especially including lysine, dilysine, or glycinelysine.

In certain additional embodiments, the linker group L is an amino acid, a dipeptide or an oligopeptide containing from 1 to 12, preferably 1 to 6 amino acid monomers or more. In certain embodiments, the oligopeptide is a dipeptide and the dipeptide is a dilysine or a glycinelysine dipeptide. When lysine is used as an amino acid in an oligopeptide linker, the sidechain alkylene amine is often used to link other linker groups or other components in the molecule.

In certain additional embodiments, the linker group L is a group

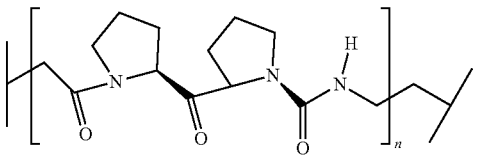

polyproline linker or

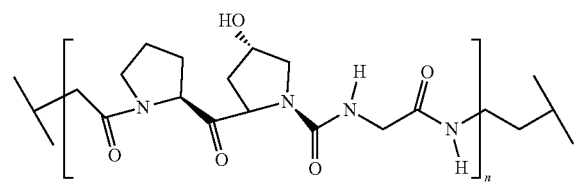

collagen linker, a group

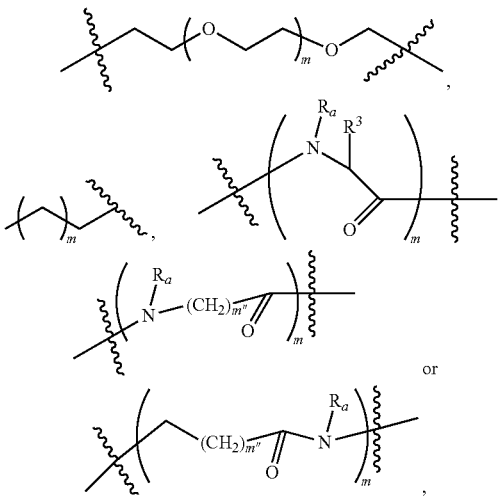

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);

Where $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl);

m" is an integer from 0 to 25, preferably 1 to 10, 1 to 8, 1, 2, 3, 4, 5, or 6;

m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or L is a linker according to the chemical formula:

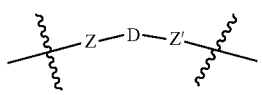

Where Z and Z' are each independently a bond, $-(CH_2)_i-O$, $-(CH_2)_i-S$, $-(CH_2)_i-N-R$,

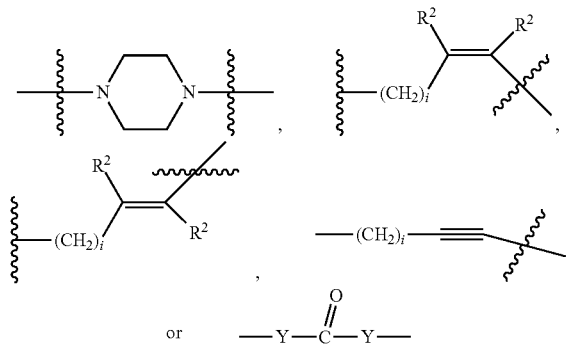

wherein said $-(CH_2)_i$ group, if present in Z or Z', is bonded to [MULTICON], [ABT], [CBT], or [TLR] or an optional difunctional connector group [CON], if present;

Each R is independently H, or a $C_1$-$C_3$ alkyl or alkanol group;

Each $R^2$ is independently H or a $C_1$-$C_3$ alkyl group;

Each Y is independently a bond, O, S or N—R;

Each i is independently 0 to 100, 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

D is

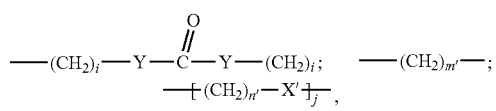

or a bond, or D may be

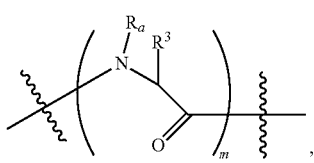

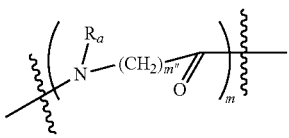

or

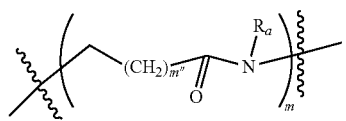

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45);

with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m" is an integer between 0 to 25, preferably 1 to 10, 1 to 8, 1, 2, 3, 4, 5, or 6;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R;

R is as described above, $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl).

[MULTICON] is preferably a multifunctional connector group or molecule according to the chemical structure:

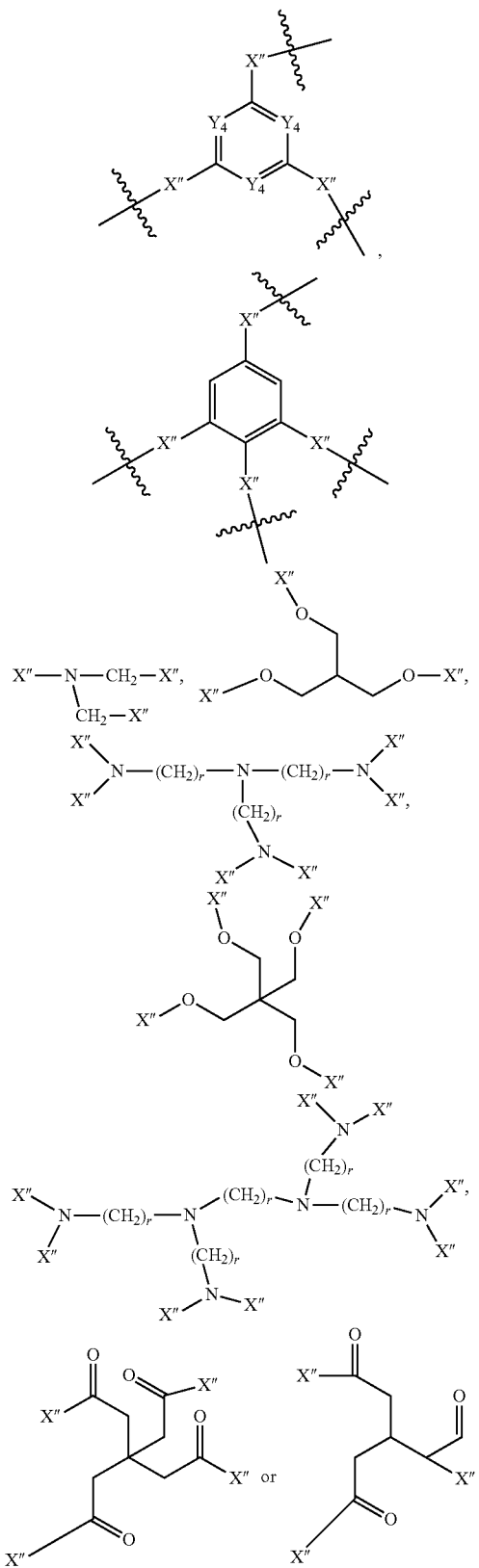

where $Y_4$ is C—H or N; and

Each X" is independently derived from an electrophilic or nucleophilic group, preferably $(CH_2)_{n''}O$, $(CH_2)_{n''}N^{RCON}$, $(CH_2)_{n''}S$, $(CH_2)_{n''}$, $(CH_2)_{n''}C=O$ or a [CON] group;

the substitutent RCON is H or a $C_1$-$C_3$ alkyl, preferably H or $CH_3$ and n" is 0, 1, 2 or 3.

The optional difunctional connector group or molecule [CON], if present, is a moiety according to the chemical structure:

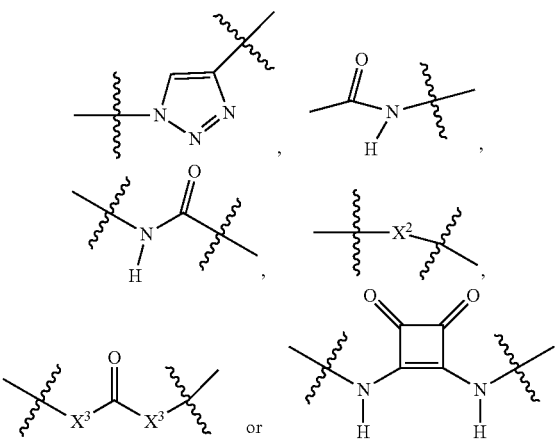

Where $X^2$ is O, S, $NR^4$, S(O), $S(O)_2$, —$S(O)_2O$, —$OS(O)_2$, or $OS(O)_2O$;

$X^3$ is $NR^4$, O or S; and $R^4$ is H, a $C_1$-$C_3$ alkyl or alkanol group, or a —$C(O)(C_1$-$C_3)$ group; or a pharmaceutically acceptable salt, solvate or polymorph thereof.

In preferred aspects of the invention, the immune binding terminus [IBT] is CP33, indicated above.

In preferred aspects of the invention, [CBT] is

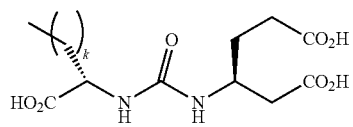

Where k is an integer from 0 to 20, 1 to 20, 1 to 8, 2 to 6, 3 to 5, 3 to 4, 1, 2, 3, 4, 5 or 6.

In certain preferred aspects, the multifunctional connector moiety [MULTICON] is a 1,3,5-triazinyl group according to the structure:

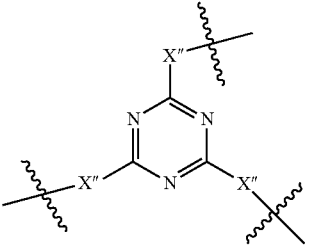

wherein each X" is independently O, S, C=O, or NR$^{CON}$, and R$^{CON}$ is H or CH$_3$, preferably H.

In certain preferred aspects, the compound contains a difunctional connector moiety [CON} according to the structure:

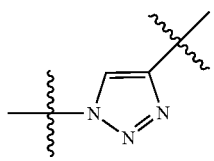 [SMILES: *c1cn(*)nn1]

group which can be covalently bonded at

with a IBT group or a CBT group or alternatively, is preferably bonded to two linker groups to form an extended linker group or directly to a [IBT] or [CBT] group. In certain additional preferred aspects, the [CON] group is In certain embodiments, [CON] is often a

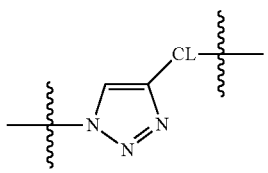

group;
where CL is

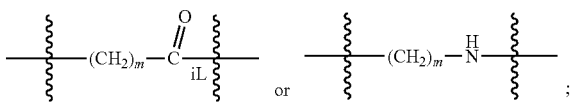

m in CL is an integer from 0 to 12, often 0, 1, 2, 3, 4, 5 or 6;
and iL is 0 or 1, often 1;
In certain embodiments, this [CON] group is often linked through the amine of the triazole to the ring structure of [MULTICON].

In still other aspects the linker group is a oligo or polyethyleneglycol moiety of the structure:

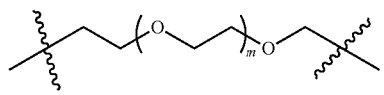

Where m is from 1 to 100 or as otherwise described herein, preferably from 1 to 12, 2 to 10, 4 to 8, 2 to 6, 8 to 12, 2, 3, 4, 5, 6, 7, 8, 9, 10 11 or 12. Noted here is that polypropylene glycol or polyethylene glycol-co-polypropylene glycol linkers (block copolymers where the polyethylene glycol portion of the block is from 1 to 12 polyethylene glycol units in length and said polypropylene glycol portion of the block is from 1 to 12 polypropylene glycol units in length, the total number of block copolymer units being from 1 to 100, 1 to 50, 1 to 25, 1 to 15, 1 to 12, 1, 2, 3, 4, 5, 6, 7, 8, 9, 10, 11 or 12) may be substituted for PEG groups in the present compounds. This group may also be bonded to two additional linker groups to provided extended linker groups or directly to one or two functional groups [IBT] and/or [CBT].

Preferred compounds according to the present invention are set forth in attached FIG. 2. Further preferred compounds based upon these compounds preferably eliminate the biotin moiety of the compounds in FIG. 2 (which are present for use as reporter in these exemplified compounds) by, for example, binding the [IBT] group of compound 1 to an amino acid or dipeptide such as glycine or alanine or glycine alanine to provide final compounds, or as in compound 2 and 3, by end-capping the lysine group (preferably the carboxylic group with an amine to form the amide as otherwise described herein or the amine with an acyl group, also as described herein).

Pharmaceutical compositions comprising combinations of an effective amount of at least one trifunctional chimeric compound SyAM compound according to the present invention, and one or more of the compounds as otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional non-antibody attracting compound which may be used to treat cancer, prostate cancer or metastatic prostate cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of a chimeric antibody recruiting compound according to the present invention including pharmaceutically acceptable salts, solvates or polymorphs, thereof optionally in a pharmaceutically acceptable carrier or diluent, either alone, or in combination with other known anticancer or pharmaceutical agents, preferably agents which can assist in treating prostate cancer, including metastatic prostate cancer or ameliorate the secondary effects and conditions associated with prostate cancer. This treatment can also be administered in conjunction with other conventional cancer therapies, such as radiation treatment or surgery.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Rationale for Design of Compounds

The first goal in constructing such SyAM-Ps was to design an appropriate bifunctional molecule capable of binding to both the FcγRI receptor and PSMA. We reasoned that linking [CBT] (i.e., PSMA binding motif) to the IBT (i.e., FcγRI binding motif) might allow the bifunctional molecule (SyAM-P1) to mimic an antibody-recruiting molecule, and therefore be able to template ternary complexes between cell-surface PSMA and FcγRI.

PSMA

PSMA is a cell surface protein that is highly overexpressed on prostate cancer cells, in comparison to normal cells of the prostate. Several small-molecule ligands have been developed that bind PSMA selectively and with high affinity, including 2-PMPA and the glutamate ureas. The [CBT] (PSMA binding moiety) was chosen accordingly and is used in the present invention.

For the immune activation, we chose to target an immune activating member of the Fc receptor family, FcγRI, which is expressed on numerous cells of the immune system. In particular, FcγRI is a cell surface immune receptor responsible for initiating pro-inflammatory responses against antibody-opsonized targets. This receptor binds to the Fc portion of IgG, and it is expressed on the surface of numerous immune cells, including monocytes and macrophages. Ligation of this receptor leads to varied pro-inflammatory responses, which include phagocytosis and reactive oxygen species generation. Targets displaying multiple copies of an FcγRI binding motifs, induce receptor crosslinking and subsequent signaling, which results in a pro-inflammatory response.[11] Recently, peptides capable of binding to receptors in the Fc-gamma family have been reported.[12,13,14] Specifically, CP33, a peptide that can bind to FcγRI, was discovered using phage display.[12] Therefore, the inventors developed the IBT portion of the SyAM preferably using the CP33 peptide to allow selective recruitment and subsequent activation of effector cells expressing FcγRI.

Accordingly, the inventors first synthesized the SyAM-P1 molecule, using Fmoc solid phase peptide synthesis to connect the two moieties (FIG. 2). As a consequence of that chemical synthesis the inventors tried to determine whether linking the two moieties would influence their ability to bind their respective protein targets, in a selective manner (FIG. 3A,B). The inventors thereafter evaluated the ability of the first-generation of SyAM-P molecules, identified as SyAM-P1, to bind PSMA on RM1.PGLS cells (FIG. 3A) or FcγRI on IIA1.6 cells (FIG. 3B). These experiments were conducted using SyAM-P1 molecules that were functionalized with biotin, and the bound SyAM-P1 was detected using a fluorescently labeled streptavidin, via flow-cytometry. SyAM-P1 evidenced a capability to bind to its respective targets. The inventors next evaluated SyAM-P1's ability to induce ternary complex formation, using soluble PSMA and FcγRI expressing cells (IIA1.6 cells) (FIG. 3c). The binding of PSMA to the cells was probed with a phycoerythrin anti-PSMA antibody, and was analyzed using flow cytometry. The inventors found that the ternary complex formation between FcγRI expressed on the surface of IIA1.6 cells and soluble recombinant PSMA is mediated through SyAM-P1.

Taken together, this data clearly indicates that SyAM-P1 can interact with both FcγRI and PSMA simultaneously, thus forming ternary complexes in a cellular milieu. This formation of a ternary complex mimics an antibody's ability to bind its target protein and the Fc receptor. These results serve as critical validation for the general structural design and the computational model, on which it was based. Additionally, connecting the two binding moieties with a hydrophobic linker did not negate the ability of the individual components from binding to their respective partners selectively.

Figure 3:
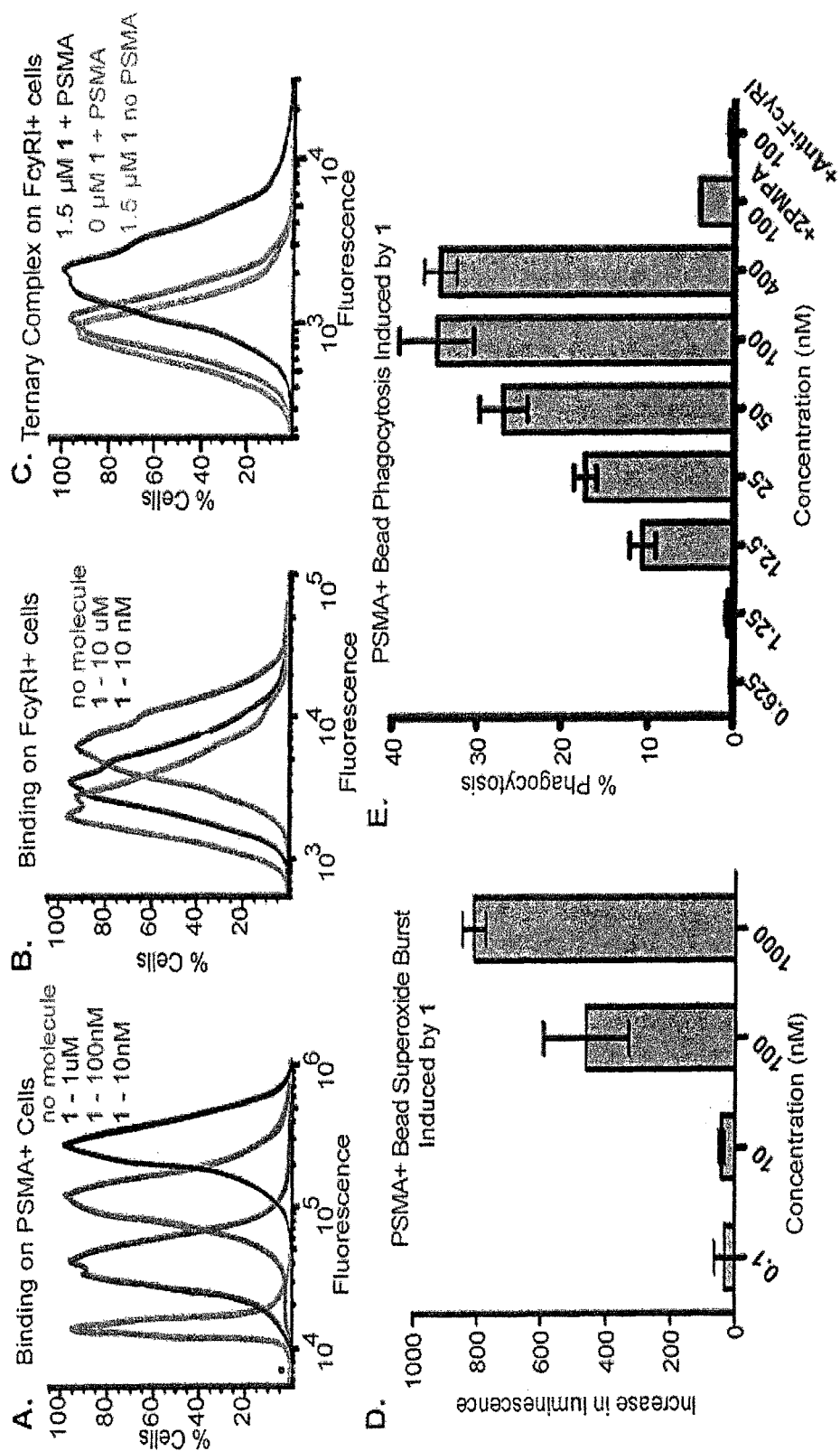
FIG. 3 shows A) binding of compound 1 to PSMA expressing RM1.PGLS cells in a dose dependent manner; B) binding of 1 (SyAm-P1) to IIA1.6 cells expressing FcγRI in a dose dependent manner; C) ability of 1 to template a ternary complex between IIA1.6 cells expressing FcγRI and soluble recombinant human PSMA; D) superoxide burst generation against PSMA labeled beads by IFN-γ primed U937 cells induced by 1. Phagocytosis and superoxide burst data is representative experiments performed in triplicate on three separate occasions; E) phagocytosis using IFN-γ primed U937 cells as effectors and fluorescent polystyrene PSMA labeled beads induced by 1 in a dose dependent and PSMA dependent manner.

SyAM-P1 was capable of binding to both PSMA and FcγRI selectively, and thus formation of a ternary complex between targets displaying PSMA and primed effector cells should induce a pro-inflammatory response. The inventors next tried to determine whether the SyAM-P1 molecule can crosslink FcγRI and induce an immune response by immune effector cells. To that end, to evaluate the pro-inflammatory responses mediated by SyAM molecules, the inventors analyzed the superoxide burst and phagocytic responses of immune effector cells. (FIG. 3 D,E). The inventors used an immortalized monocytic effector cell line (U937 cells) to evaluate the SyAM-P1-mediated immune effector responses. 937 cells were primed with IFN-γ, which induces an upregulation of FcγRI and primes the cells for the pro-inflammatory responses (superoxide burst and phagocytosis). Superoxide burst is characterized by the release of reactive oxygen species (ROS) that can occur during pro-inflammatory responses. The magnitude of this response can be measured using the lucigenin assay. Phagocytosis is the active engulfment of an opsonized target.

The phagocytosis assay used involved incubating PSMA labeled Fl1 fluorescent beads with Fl4 stained IFN-γ primed U937 cells, in the presence of SyAM-P1. Phagocytosis was observed by flow cytometry and microscopy. The results indicated that SyAM-P1 was able to induce superoxide burst (FIG. 3D) and phagocytosis of PSMA coated beads (FIG. 3E) in a dose-dependent manner. In particular, SyAM-P1 was able to induce superoxide burst at concentrations of 100 nM and 1 µM, in a target dependent manner. In the phagocytosis assay, the compound had an $EC_{50}$ of 26 nM. These immune effector responses identified above were abrogated, when the assays were conducted in the presence of either a PSMA inhibitor (2-PMPA) or FcγRI inhibitor (IgG). (data not shown)

The results evidenced that the ternary complex binding results translated into active immunological responses. These proof of principle experiments for SyAM-P1 supported the hypothesis that a fully synthetic molecule might induce an FcγRI-dependent immune response against targets displaying PSMA. Both the targeting and effector functions of an antibody could be effectively mimicked by a fully synthetic bifunctional molecule.

Since SyAM-P1 was able to induce effector-cell mediated responses against target protein coated beads, the inventors then evaluated if the molecule can elicit the effects against PSMA expressing cells. To that end, the inventors evaluated the SyAM-P1 induced immune responses by primed U937 effector cells against PSMA expressing RM1.PGLS cells. They tested the U937-mediated immune effects by evaluating both superoxide burst and phagocytosis of effector cells, analogous to the protein coated bead experiments. In this experiment, IFN-γ primed U937 cells were incubated with PSMA expressing RM1.PGLS cells, and treated with various concentrations of SyAM-P1. The resulting superoxide burst response was measured using the lucigenin assay (data not shown). Additionally, primed U937 cells (stained with DiD, an FL4 membrane dye) were incubated with target RM1.PGLS cells (stained with DiI, an FL1 membrane dye), in the presence of various concentrations of SyAM-P1. The resulting phagocytosis—indicated by FL1 and FL4 double positive cells—was measured using two-color flow-cytometry. As a positive control, ARM-P8 combined with anti-DNP antibodies was utilized. While ARM-P8 was capable of inducing significant responses, SyAM-P1 was unable to induce any immune responses against the target cells (data not shown). The positive response seen with the Arm-P8 control, could potentially be attributed to the ability of antibodies to ligate both FcγRI and FcγRIIA on the immune effector cells, increasing immune signaling and phagocytic responses.

Given that SyAM-P1 molecule was capable of inducing effector cell-mediated phagocytosis against beads labeled with PSMA, yet unable to elicit similar responses against PSMA expressing cells, we hypothesized that this may be a result of differential levels of PSMA molecules per µm² of surface area of the two different targets. (FIG. 5). These results prompted the inventors to compare the PSMA labeling on the surface of beads, with that of RM1.PGLS cells.

The level of opsonization of the target cell is directly proportional to the effector cell-mediated immune response observed, and importantly, a threshold opsonization must be reached prior to observing any response. The ability of SyAM-P1 to mediate phagocytosis was assessed utilizing beads loaded with various amounts of PSMA. The level of phagocytosis of beads by primed U937 cells directly correlated to the level of PSMA displayed on the surface. (FIG. 5). The level of expression of PSMA on the surface of RM1.PGLS cells was measured with a phycoerythrin anti-PSMA antibody and calculated with phycoerythrin fluorescent calibration beads. RM1.PGLS cells display a fewer PSMA proteins per µm than the lowest level of bead tested. (FIG. 5). RM1.PGLS cells displayed approximately 918 PSMA proteins/um², while the beads used in the assay displayed approximately 5577 PSMA proteins/um². Given the direct correlation between effector responses and the level of opsonization, the level of PSMA expression on the surface of the target cells was insufficient to induce a SyAM-P1-mediated response. Given that the level of PSMA on the surface directly correlates to the efficacy of the SyAM-P1 molecule, the inventors then hypothesized that increasing the affinity of the TBT region of the molecule, through bivalent display, might increase the amount of SyAM-P1 molecules binding to the surface with PSMA, at equilibrium. The inventors reasoned that: by increasing the local concentration of the PSMA binding moiety, the apparent Kd will be increased, which would enhance the range of effective concentrations and increase the level of molecule displayed at equilibrium.

Pursuant to that hypothesis, the SyAM-P molecule was redesigned to incorporate a bivalent display of PSMA targeting motifs in order to enhance its efficacy (SyAM-P2)

Figure 4:
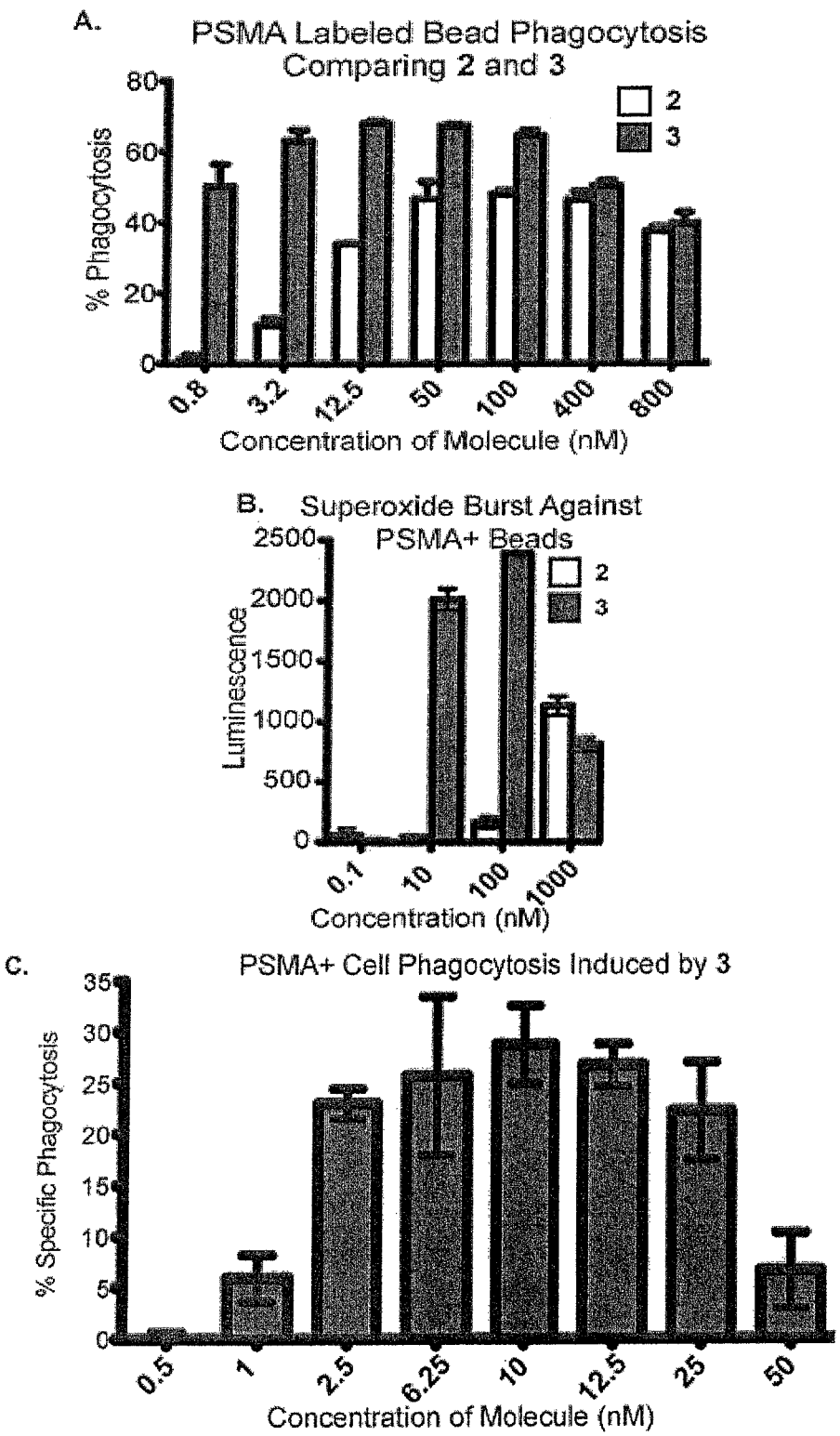
FIG. 4 shows A) comparison of phagocytosis induced by compound 2 (SyAMP-2) and 3 (SyAMP-3) against PSMA labeled beads by IFN-γ primed U937 cells. A dose and PSMA dependent response is seen with an increase in efficacious range and level by compound 3 as compared to compound 2; B) comparison of superoxide burst by primed U937 cells against PSMA labeled beads in a dose dependent manner by compounds 2 and 3 with an increase in range and amount of compound 3; C) phagocytosis of PSMA expressing RM1.PGLS cells as induced by compound 3 using IFN-γ; D) amnis flow cytometry imaging of phagocytosis with representative images of completed phagocytosis with representative images of completed phagocytosis as compared to phagocytic cup formation. Channels shown are brightfield, target (stained with F11 dye DiO), nuclide (stained DAP1), macrophage (stage F12 DID) and merged image.
Figure 4:
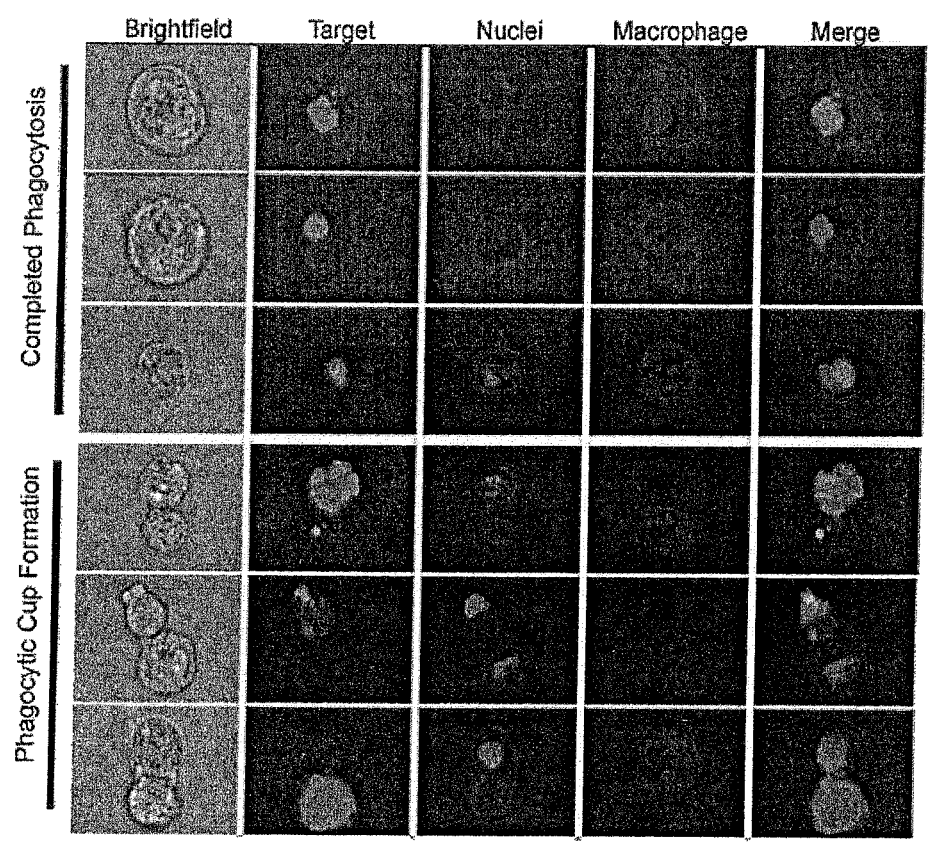

(FIG. 2, compound 2). First, they verified the binding and compared the affinity of SyAM-P2 to PSMA coated beads. Thereafter, SyAM-P2-mediated immune responses of primed U937 cells against PSMA coated beads was evaluated. (FIG. 4A). Finally, the inventors tested the effects of SyAM-P2 on its ability to induce a superoxide burst response or phagocytic response in primed U937 cells, against RM1.PGLS cells. (Data not shown). The binding of SyAM-P1 to PSMA coated beads ($EC_{50}$=40 nM) were less effective than that of SyAM-P2 ($EC_{50}$=26 nM).

SyAM-P2 was able to induce a much higher level of phagocytosis (SI FIG. 2A) of PSMA coated beads, with a wider efficacy range, in comparison to SyAM-P1. Encouraged by these results, the inventors proceeded to evaluate the ability of SyAM-P2 to mediate immunological effects against RM1.PGLS cells. Unfortunately, no response was seen with either superoxide burst or phagocytosis (data not shown). However, increasing the display of binding motifs, directly increased the level of superoxide burst response and phagocytosis against PSMA coated beads. This verified the hypothesis that increasing the valency on the PSMA binding side will increase the apparent Kd (SI FIG. 4). The level of ligation of the FcγRI by SyAM-P2, in the presence of cells, is still inadequate to induce a favorable, clinically relevant immune response against PSMA expressing cells.

The inventors also explored linker length and composition in this second generation molecule, which showed the most robust results when utilizing the aminocaproic acid linker displayed in SyAM-P2 (SI FIG. 3). The second generation of SyAM molecules increased the efficacy of the PSMA-bead experiments, but still proved unable to induce a favorable response against RM1.PGLS cells. The inventors hypothesized that this is due to insufficient cross-linking of the Fc receptor. Considering this, the inventors optimized SyAM-P2 to enhance its efficacy through both a bivalent display of PSMA targeting motif and the FcγRI targeting motif; this molecule was named SyAM-P3 (FIGS. 1, 3).

Figure 6:
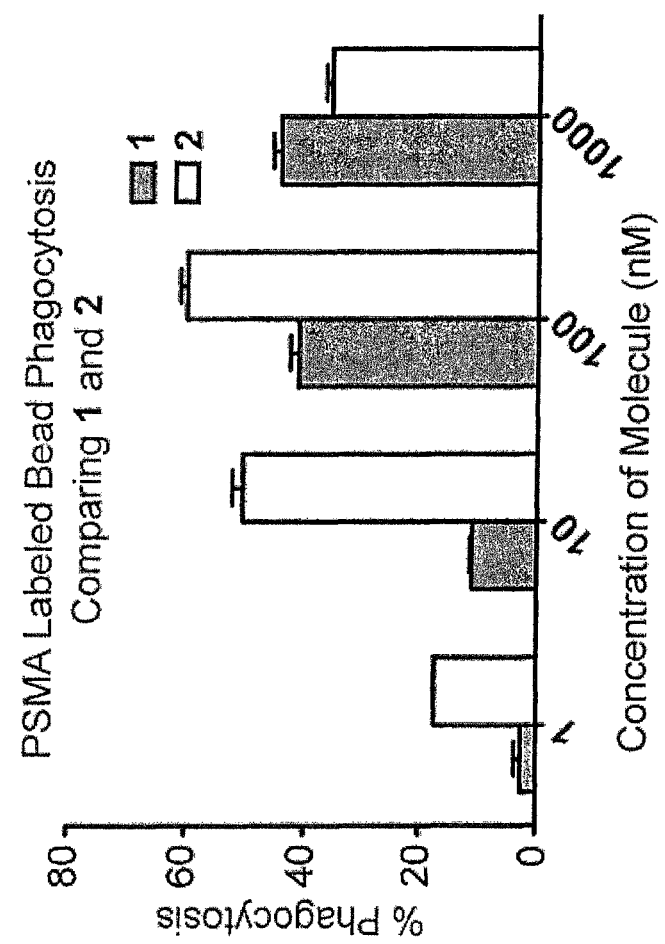
FIG. 6 shows phagocytosis of PSMA labeled 6 μm beads by IFN-γ primed U937 cells. Comparison of phagocytic response induced by various concentrations of either compound 1 or compound 2.
Figure 7:
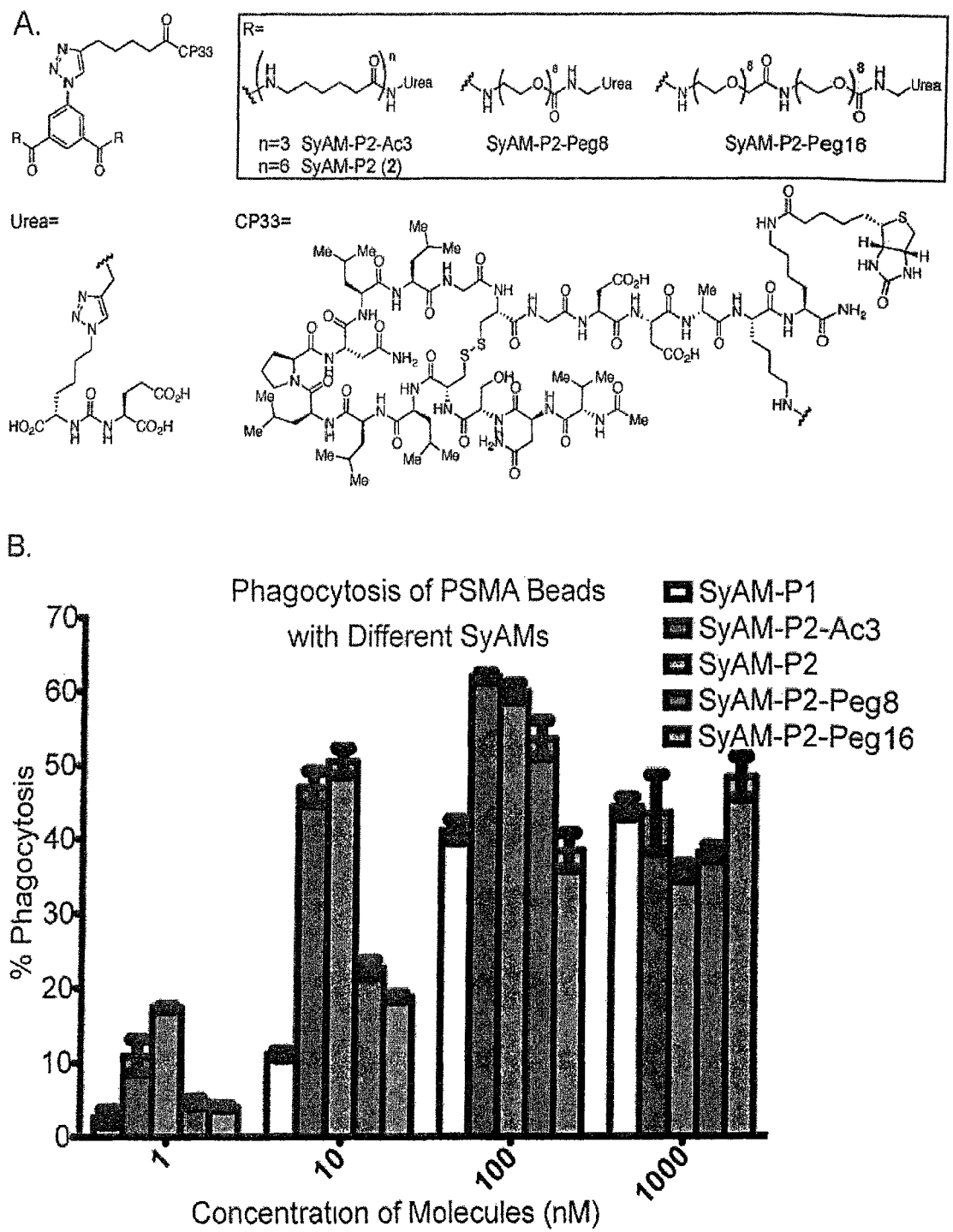
FIG. 7 shows A) structures of different ligands connecting the urea PSMA binding moieties differing in length and hydrophobicity; B) shows phagocytosis of PSMA labeled 6 μm beads by IFN-γ primed U937 cells. Comparison of phagoctic response induced by various concentrations of SyAMs possessing a pair of PSMA binding motifs linked to CP33 with various linker lengths and compositions.

The inventors then tested SyAM-P3-induced immune effects (i.e., U937-mediated superoxide burst and phagocytosis) against PSMA coated beads (FIGS. 4A and B). SyAM-P3 was able to induce a much greater immune response against PSMA-beads, in both the generation of superoxide burst (FIG. 4A) and phagocytosis (FIG. 4b) as compared to SyAM-P2; the response was greater in both potency of phagocytosis and the efficacious range. In control experiments superoxide burst was shown to be dependent on the presence of both molecule and PSMA labeling of the bead (SI FIG. 6). Phagocytosis of beads could compete with both 2-PMPA and human IgG (St FIG. 5). Finally, the inventors also evaluated the efficacy of SyAM-P3 on facilitating U937-mediated phagocytosis of PSMA expressing RM1.PGLS cells (FIG. 4C). In this case, SyAM-P3 was able to effectively induce U937-mediated phagocytosis, in a dose dependent manner, against RM1.PGLS cells (FIG. 4C). The inventors were able to visually verify the phagocytosis of RM1.PGLS cells, using a flow cytometer (Amnis) with image acquisition capabilities (FIG. 4D). Using this method, the inventors visualized both early stages of phagocytosis, where the phagocytic cup is being formed, and late stages of complete phagocytosed RM1.PGLS. This phagocytosis could compete with both 2-PMPA and human IgG (SI FIG. 7). No response was seen with SyAM-P3 and RM1.PGLS cells in the superoxide burst assay.

Figure 8:
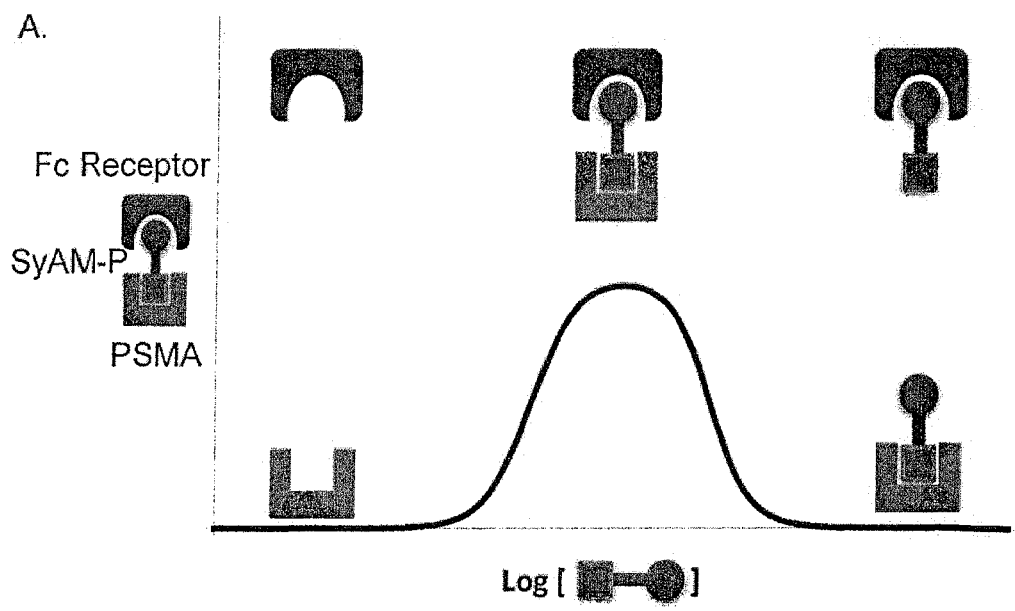
FIG. 8 shows A) prozone phenomenon where excess concentration causes a reduction in Fc receptor SyAM-P binding (even as SyAM-P with PSMA remains intact); B) shows an overlay of data fit to analytical ternary complex model. Increase in efficacy and potency consistent with a factor of 5 increase to target affiant from SyAM-P1 to SyAM-P2. Observed increase of efficacy and potency consistent with two order of magnitude increase from SyAM-2 to SyAM-P3. Increase for SyAM-P3 due to improvement of weaker binding affinity having a larger net effect in the analytical model.
Figure 8:
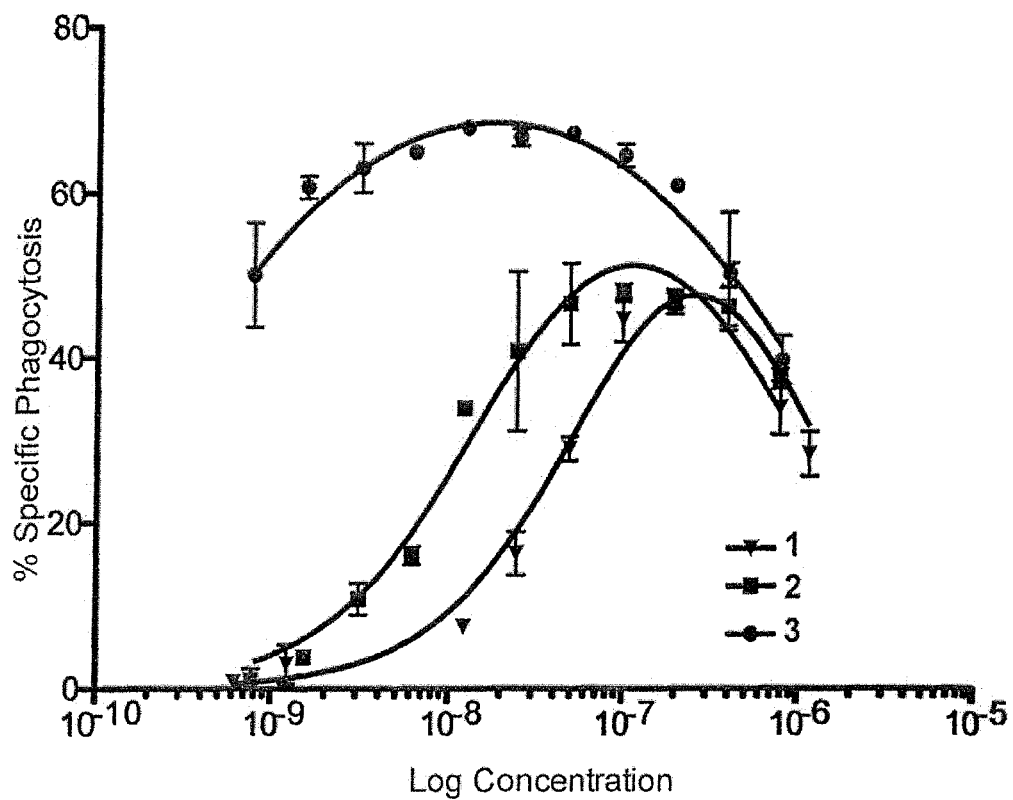
Figure 9:
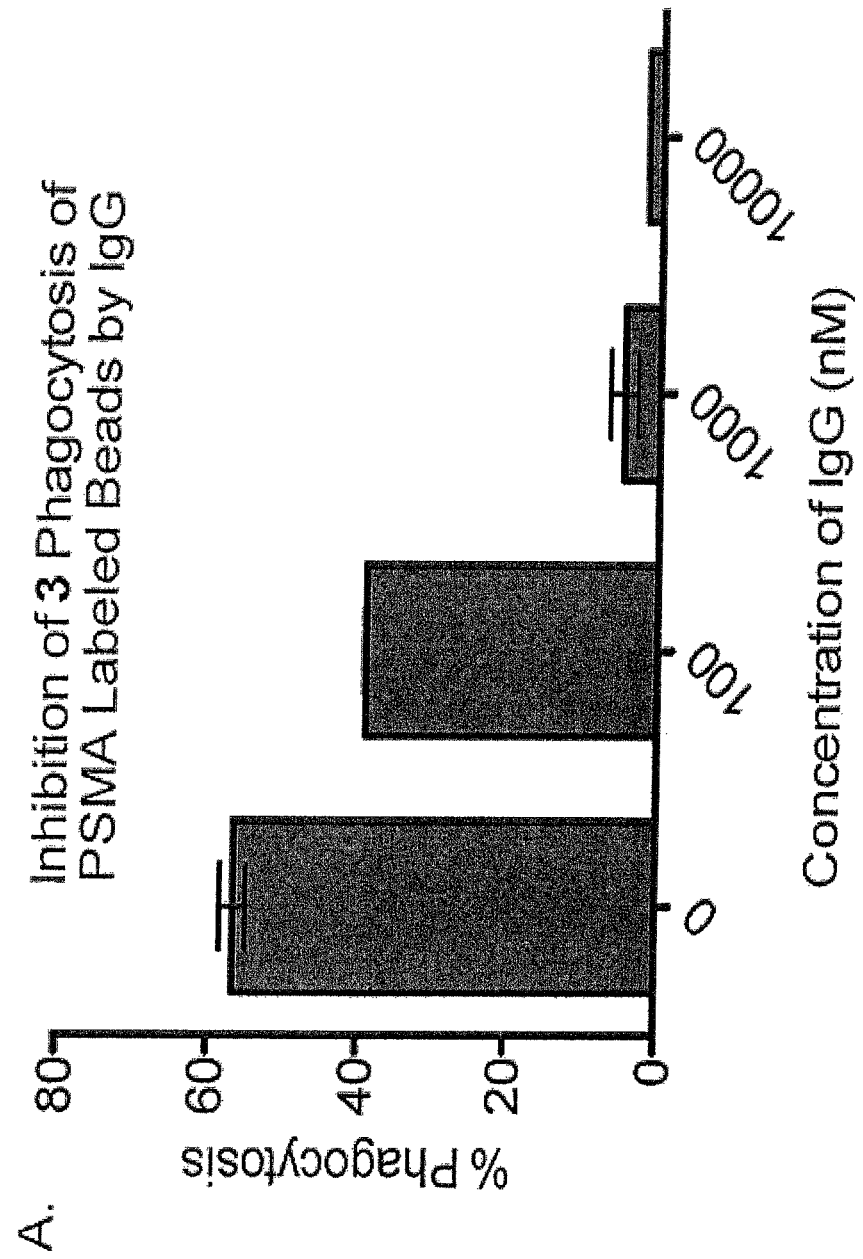
FIG. 9 shows phagocytosis of PSMA coated with 6 μm beads by IFN-γ primed by U937 cells in the presence of 50 nM of SyAM-P3. A) shows inhibition of phagocytosis by increasing concentrations (in NM) by human IgG, inhibiting the interaction of the molecule with the Fc receptor. B) shows inhibition of phagocytosis by increasing concentrations of 2-PMPA, inhibiting the interaction between the molecule and PSMA.
Figure 9:
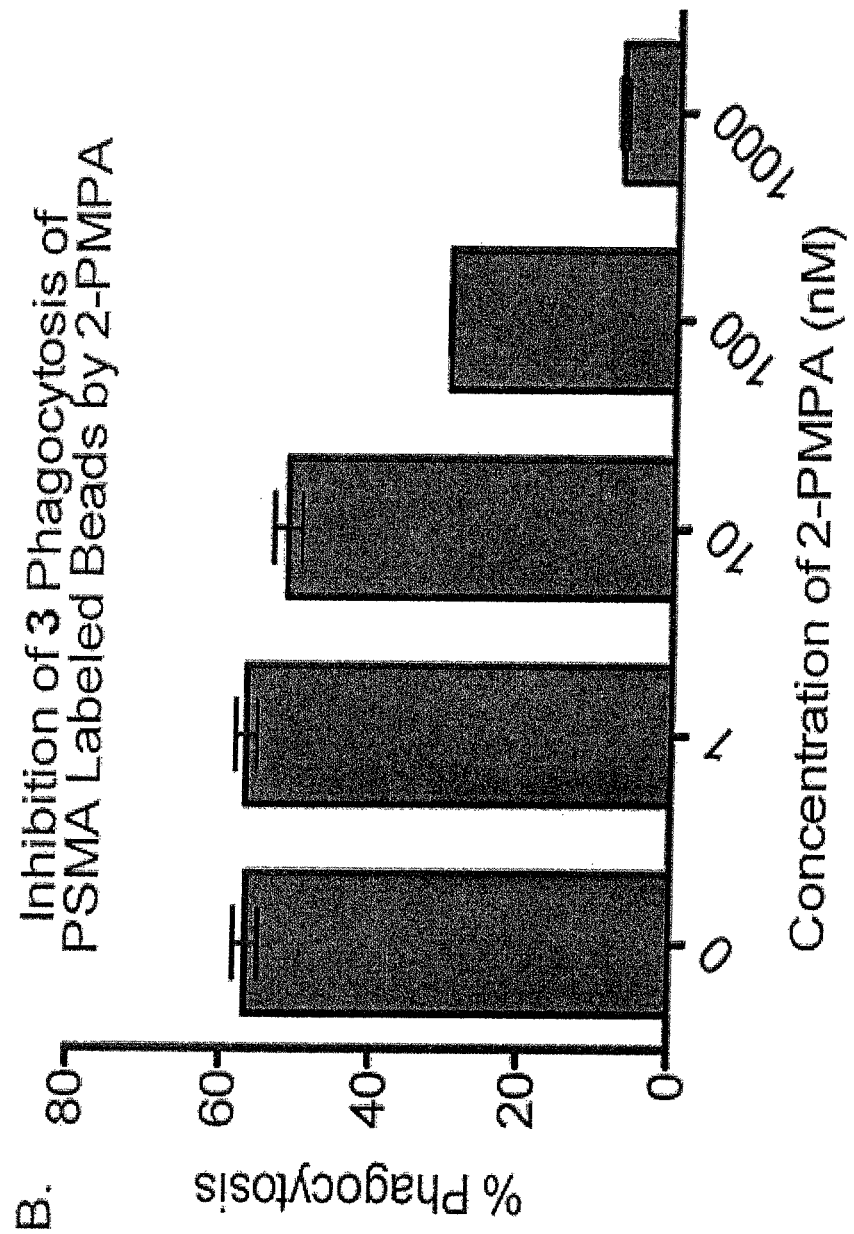
Figure 10:
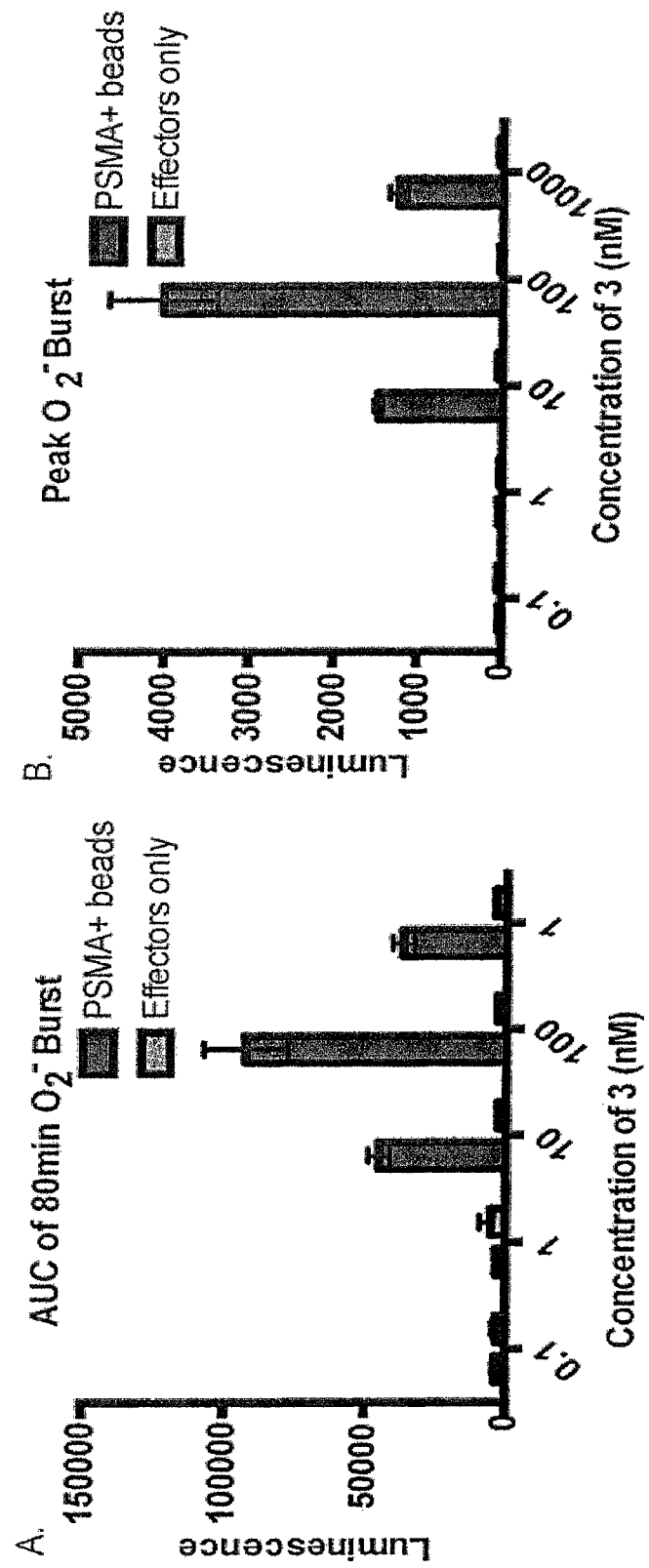
FIG. 10 shows A) the area under the curve (AUC) of superoxide burst assay comparing +/− target PSMA+ beads in the presence of various concentrations of SyAM-P3. Little to no accumulation of superoxide seen over assay time. B) shows peak superoxide production time taken (xmin) again little to no background superoxide detection in the presence of SyAM-P3 alone.
Figure 11:
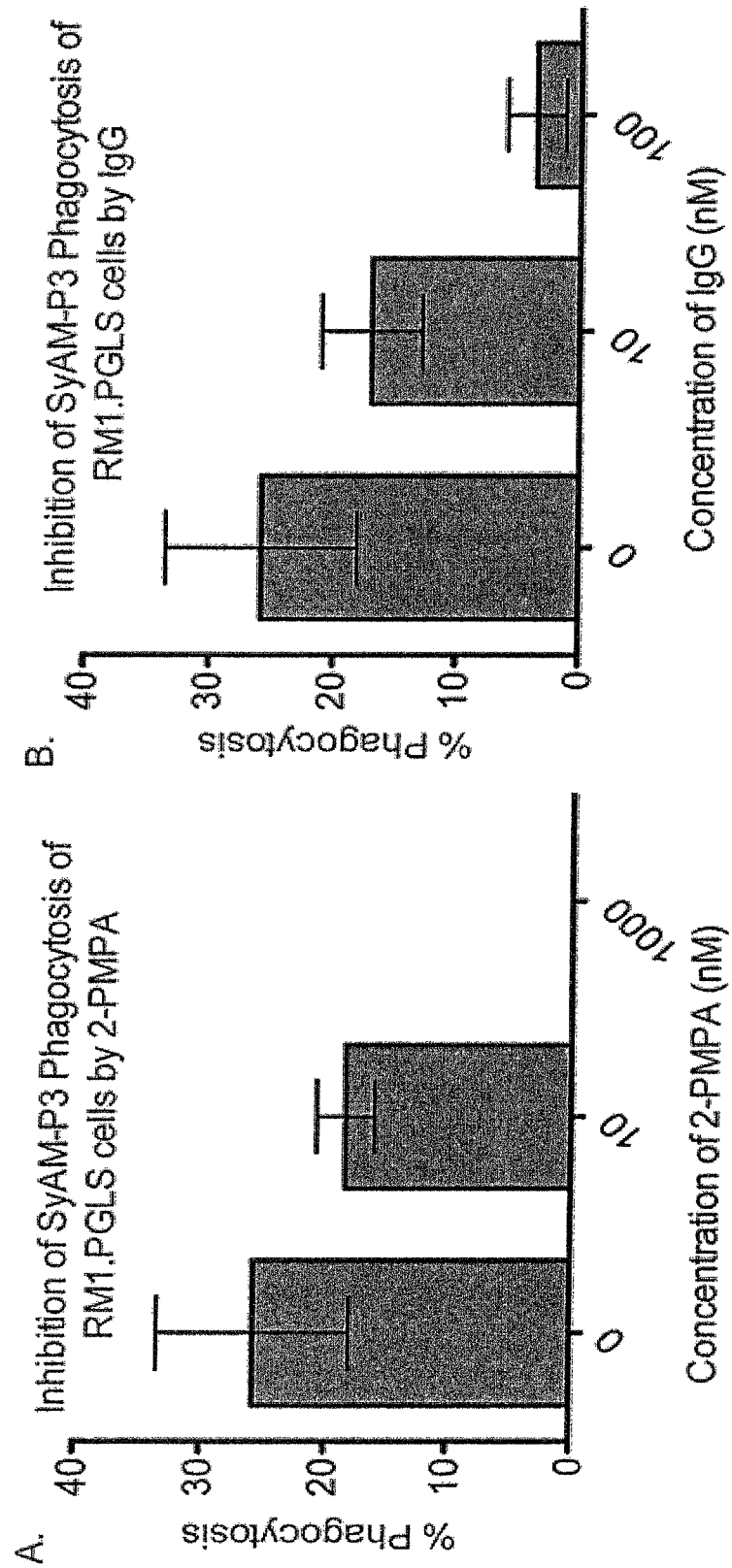
FIG. 11 shows phagocytosis of PSMA expressing RM1.PGLS cells by IFN-γ primed U937 cells in the presence of 6.25 nM of SyAM-P3. A) shows the inhibition of phagocytosis by increasing concentrations (in nM) by human IgG, inhibiting the interaction of the molecule with Fc receptor. B) shows the inhibition of phagocytosis by increasing concentrations of 2-PMPA, inhibiting the interaction between the molecule and PSMA.
Figure 12:
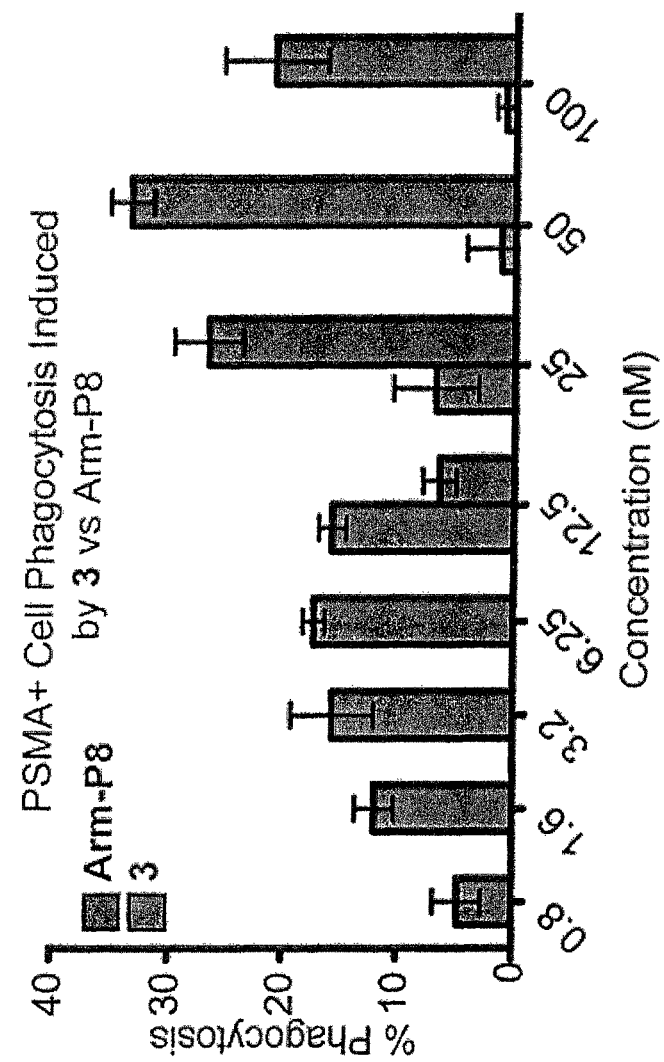
FIG. 12 shows phagocytosis of RM1.PGLS cells by Fn-γ primed U937 cells in the presence of various concentrations of either compound 3 or ArmP8 with anti-DNP antibody (133 nM). Phagocytosis substracted from background of no molecule. Bars for compound 3 evidence phagocytosis at significantly less concentration than for ArmP8.

Based on the ternary complex model, [ref] (SI FIG. 4B) increasing the number of FcγRI ligating motifs, enhanced both the potency and efficacy of SyAM-P molecules to elicit targeted immune responses against PSMA coated beads. SyAM-P3 is effective at stimulating immune effector cell-mediated phagocytosis of PSMA expressing cells. The response with SyAM-P3 peaked at 10 nM concentration of the molecule, which is a shift from the maximal response peak observed with the use of ARM-P8 and anti-DNP antibodies (SI FIG. 8). This shift in the ternary complex equilibrium maximum shows our molecule can induce an immunological response at a concentration an order of magnitude better than the ARM-P8 molecule.

Discussion

The compounds disclosed in the present application report are unique, in that they are the first reported fully synthetic molecules capable of directly mimicking a monoclonal antibody's ability to induce an immune response through FcγRI in a highly specific manner. Given that the SyAMs of the present invention are synthetic molecules capable of eliciting an immune response by directly binding to immune cells, they can mediate their functions independent of endogenous antibodies, unlike the ARM molecules.[8b,c] The SyAM molecules of the present invention function through a single activating receptor, FcγRI, limiting the cross reactivity with other arms of the immune system. The specificity of the molecule for FcγRI prevents cross ligation of the inhibitory FcγRIIb, which has been implicated in lowering the efficacy of mAbs in-vivo. By selectively targeting the Fc family of receptors, there exists the potential for cross presentation of antigenic sequences and to elicit further adaptive immune responses. The SyAMs specifically address the unfavorable aspects with mAbs such as, the lack of chemical homogeneity, the limited scope of pathogen target, activation of complement deposition impairing Fc responses,[15] and the difficulty in predicting the mechanism of action in vitro.

In addition to being easier to synthesize and purify, the scaffold and convergent synthesis of the present invention lends itself to rapid modification. This allows us to append other TBTs rapidly, thus broadening the scope of the utility of the approach. More broadly, the general strategy for using small molecules to redirect the cytotoxic functions of immune cells has the potential for application in wide range of pathophysiologically unrelated human diseases, such as viral and bacterial infection.

Chemical Synthesis

The chemical synthesis of compounds according to the present invention proceeds stepwise by preparing building blocks of various components and then condensing these building blocks onto each other to fashion compounds according to the present invention. While the specific syntheses of compounds identified in the present patent application proceeds in a stepwise fashion with individual components, various substitutions which are used may be readily substituted for other components using analogous chemistries to synthesize all of the compounds of the present invention. The following synthetic schemes are exemplary of the chemistry which is used to prepare compounds according to the present invention. This chemistry may be used directly or in an analogous fashion to prepare all of the compounds of the present invention.

SyAM-P1 (with Biotin)

Figure 15:
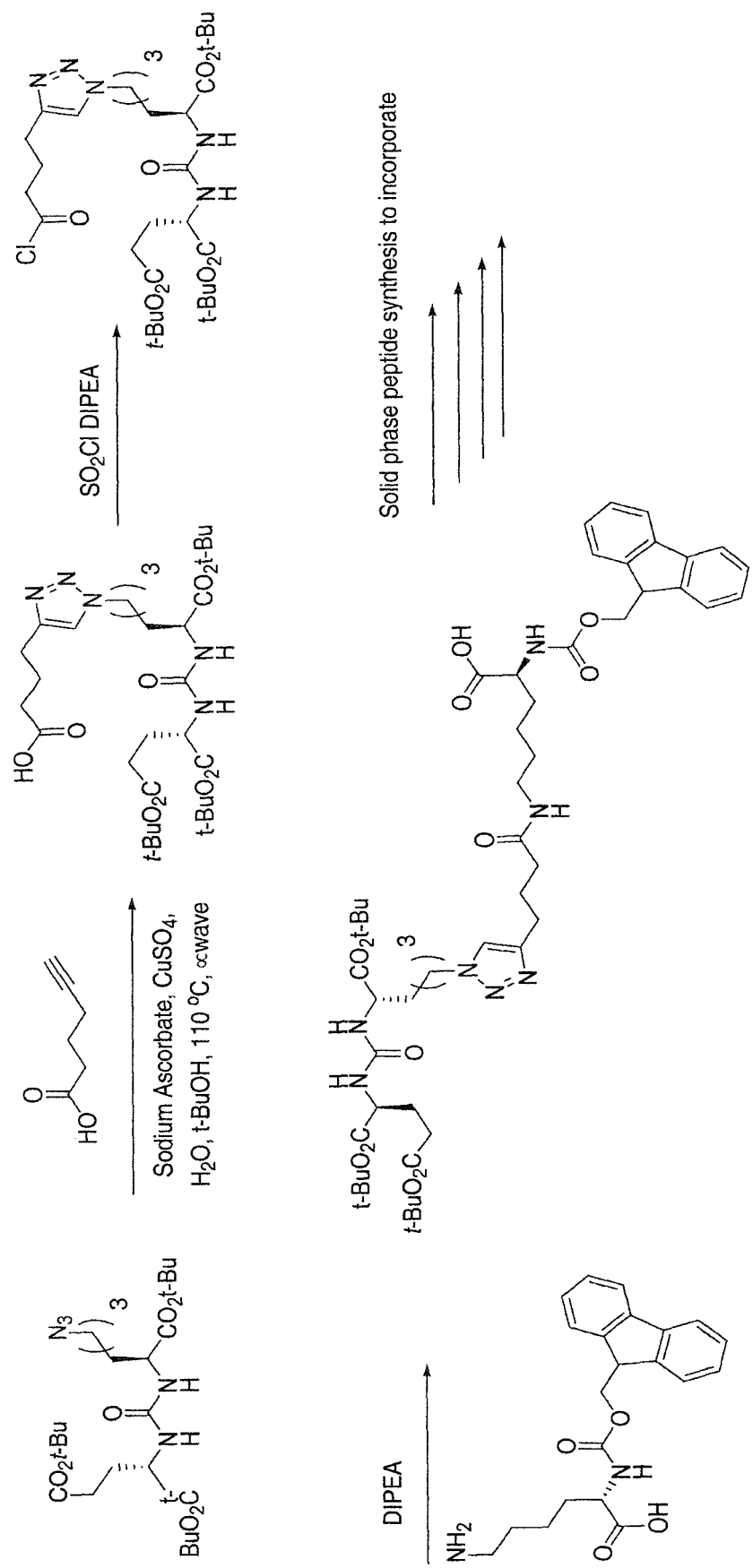
FIG. 15 provides a scheme for the chemical synthesis of SyAm-P1. This synthesis is discussed in the text of the specification in the chemical synthesis section.
Figure 16:
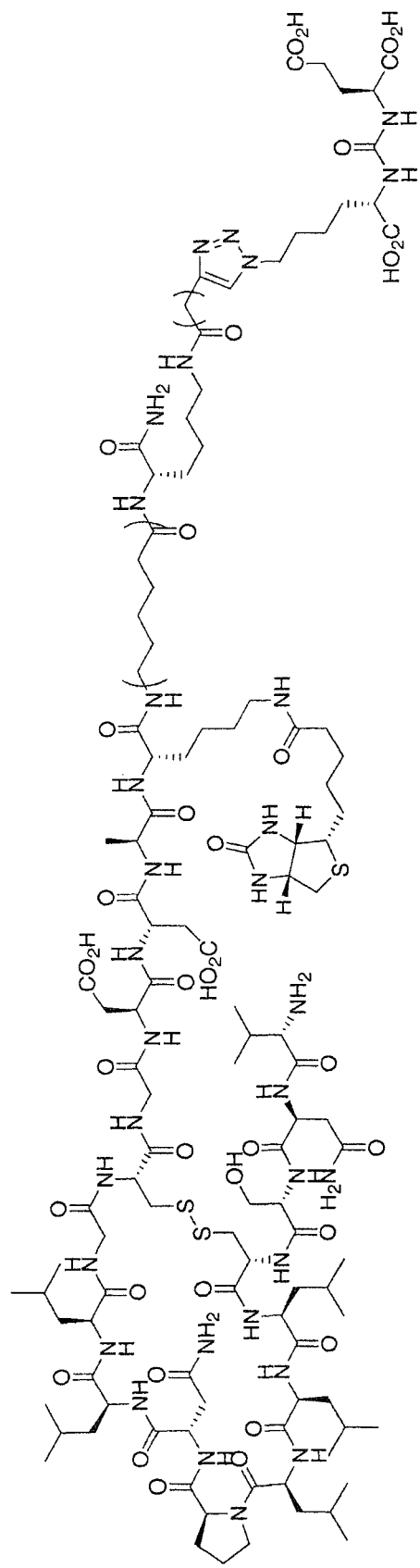
FIG. 16 shows the final product SyAM-P1, synthesized by the method presented in FIG. 15. It is noted that in diagnostic applications, the lysine amino acid and biotin covalently bonded to the CP33 moiety may be readily replaced by any number of amino acids which have unreactive amino acid side chains.

This compound is synthesized pursuant to the chemical synthesis scheme which is presented in FIG. 15 to provide SyAM-P1 of FIG. 16. Pursuant to the scheme presented in FIG. 15, the triester urea CBT group containing an azide group (presented in the reaction scheme for SyAM-P3 hereinbelow) is reacted with the acetylenic hexynoic acid in sodium ascorbate, copper sulfate, water, tert-butanol at elevate temperature in a microwave to form the triazole

[CON] group which is covalently attached to [CBT]. The free carboxylic acid group of that intermediate is then converted to an acyl chloride derivative, which is reacted with the lysine urethane derivative in DIPEA to form the CBT-lysine intermediate containing the urethane moiety. Solid phase peptide synthesis places a glycine group on the carboxyl acid of the lysine and the amine group is deprotected and substituted with a peptide linker comprising amino hexanoic acid units (FIG. 2 shows 5 amino hexanoic acid units). This intermediate is further reacted with a CP33-linked lysine group (if biotin attachment is desired) or a CP33-amino acid (alanine or glycine) to link the CP33 group to the CBT moiety molecule (without biotin attachment). Alternatively, the CP33 group can be linked to another amino acid, an oligopeptide, including a dipeptide (such as glycine alanine, glycine glycine or alanine alanine, among numerous other combinations) to provide a SyAM-P1 molecule.

SyAM-P2

Figure 17:
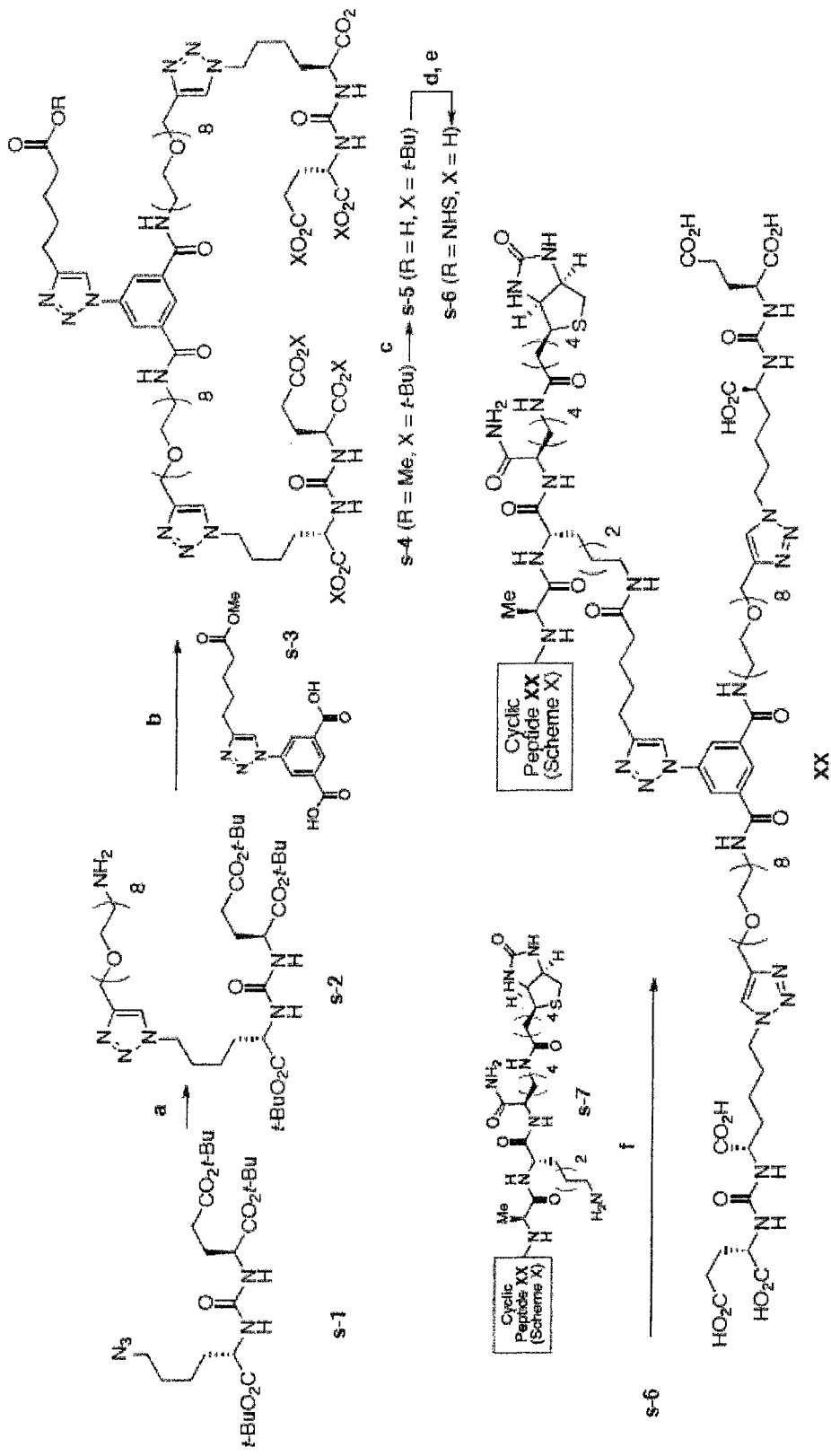
FIG. 17 shows the chemical synthesis of SyAM-P2 which contains a biotin group for diagnostic applications.
Figure 18:
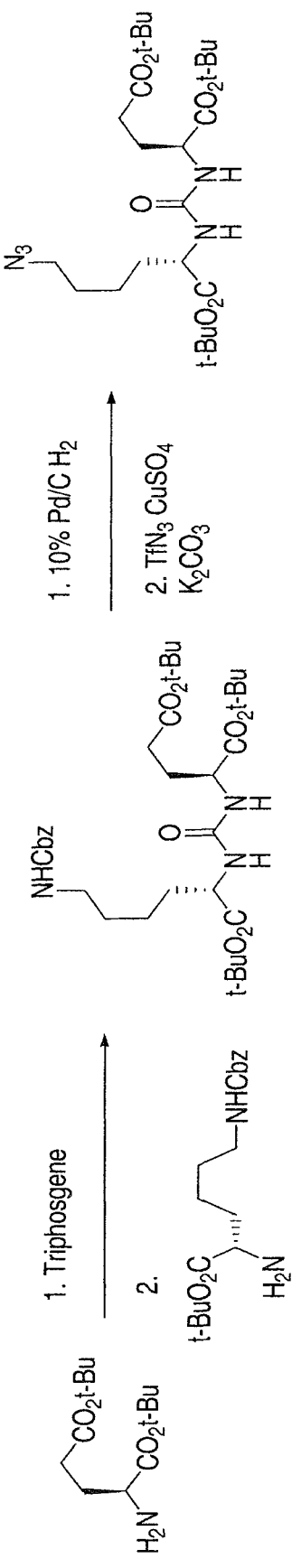
FIG. 18 shows the chemical synthesis (urea formation) and linker synthesis for certain parts of SyAM-P3.
Figure 18:
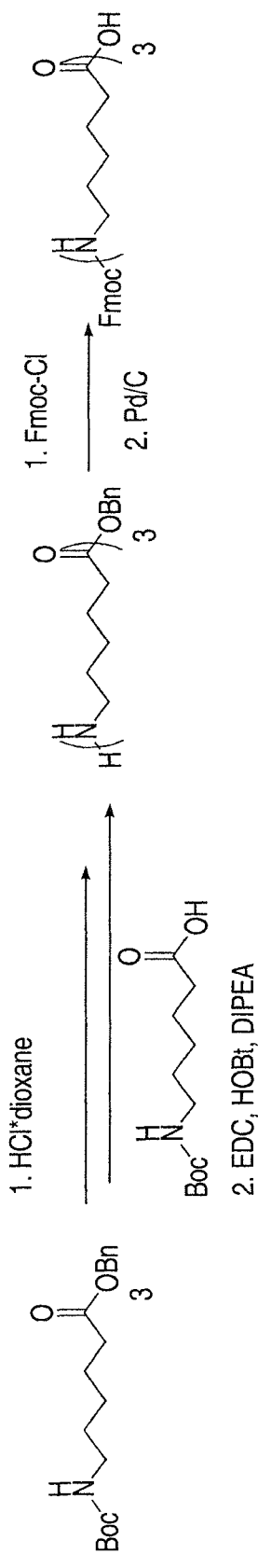
Figure 19:
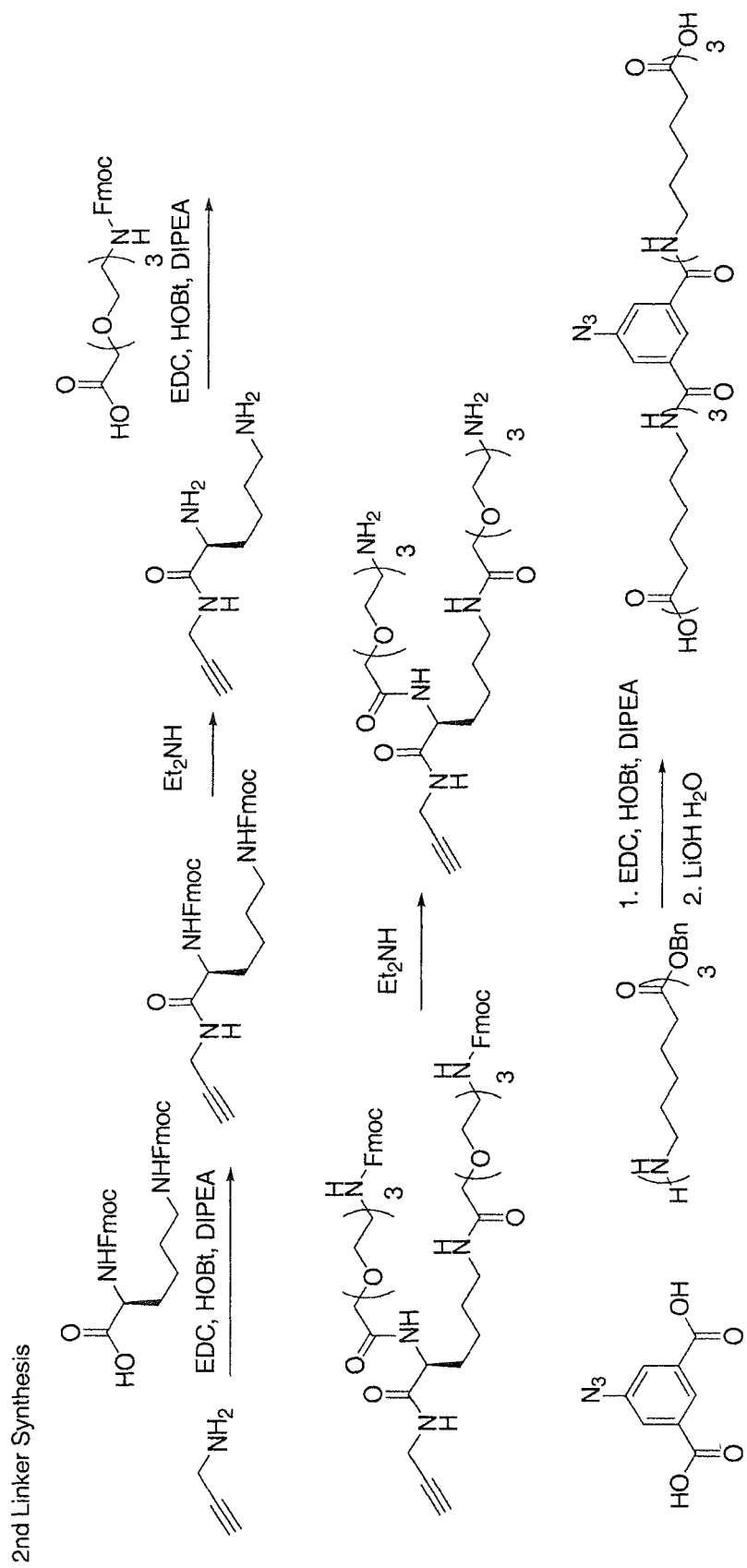
FIG. 19 shows the chemical synthesis of the second linker synthesis for SyAM-P3 which contains a [MULTICON] group.
Figure 20:
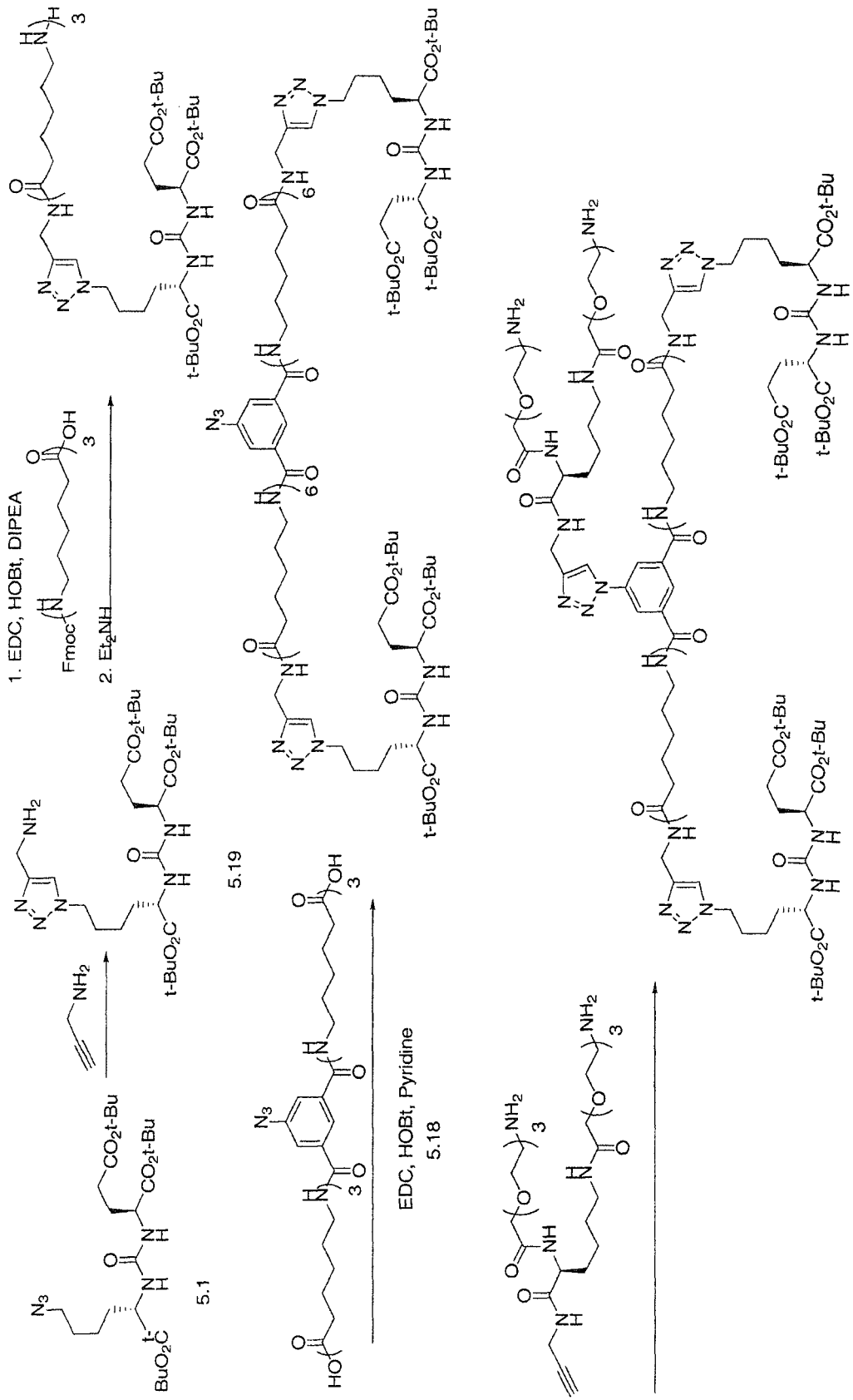
FIG. 20 shows the chemical synthesis to link the CBT groups to the [MULTICON] group containing an azide for further modification to provide SyAM-P3. The azide is subsequently shown being reacted with the complex acetylenic compound containing two free amine groups which are linked through to the triazole group formed when the acetylenic moiety reacts with the azide moiety to form the complex intermediate which can be condensed with two CP33 groups to form SyAM-P3.
Figure 21:
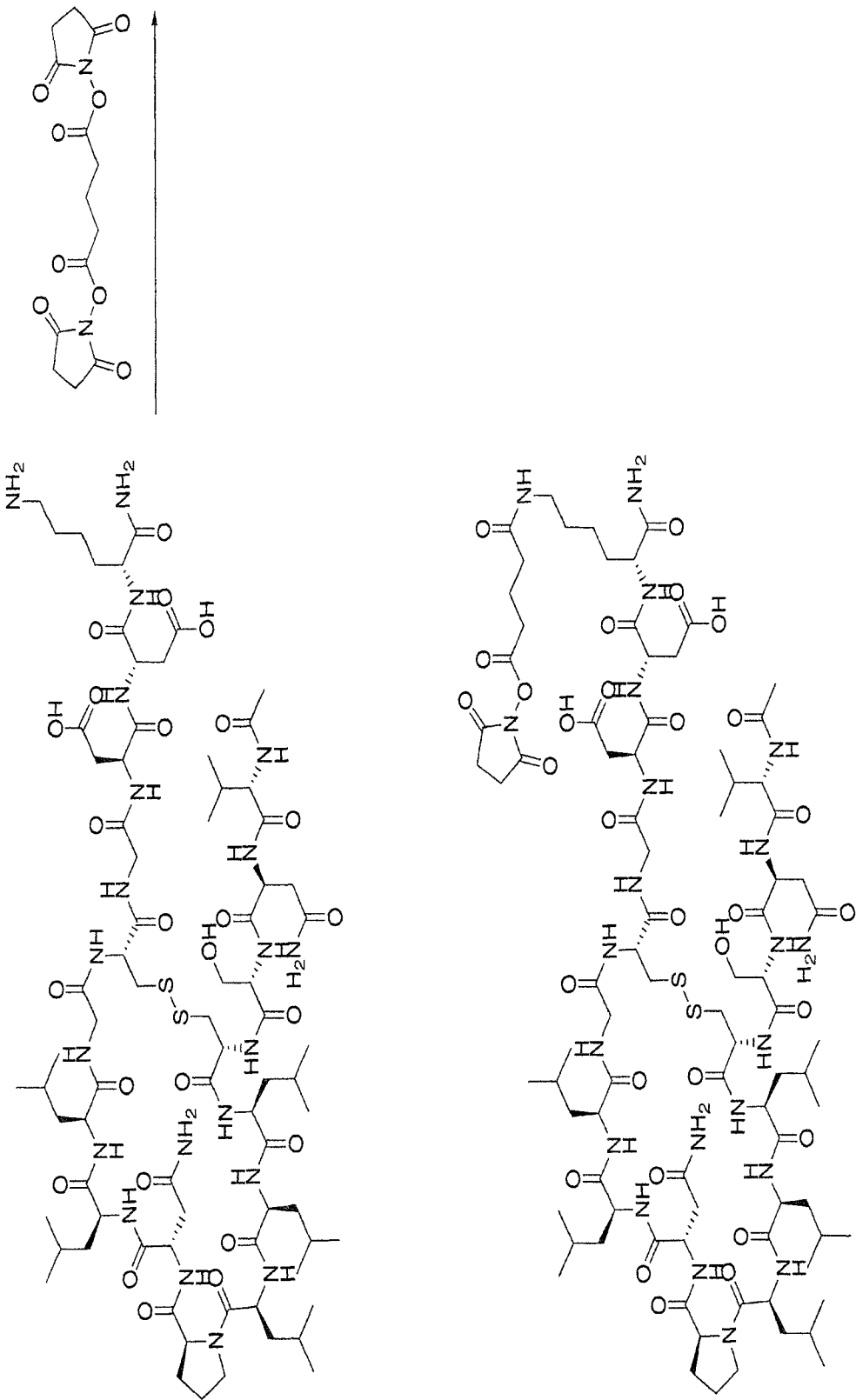
FIG. 21 shows the introduction of a diketo linker group onto the CP33-lysine intermediate (the carboxylic acid group of the lysine having been end-capped with an amine to form an amide group), the linker being end-capped with succinimide leaving groups. The final intermediate, pictures, contains a succinimide leaving group at the distill end of the diketo linker which can be reacted with the two free amine groups of the intermediate from FIG. 20 to provide the final product SyAM-P3 of FIG. 22.
Figure 22:
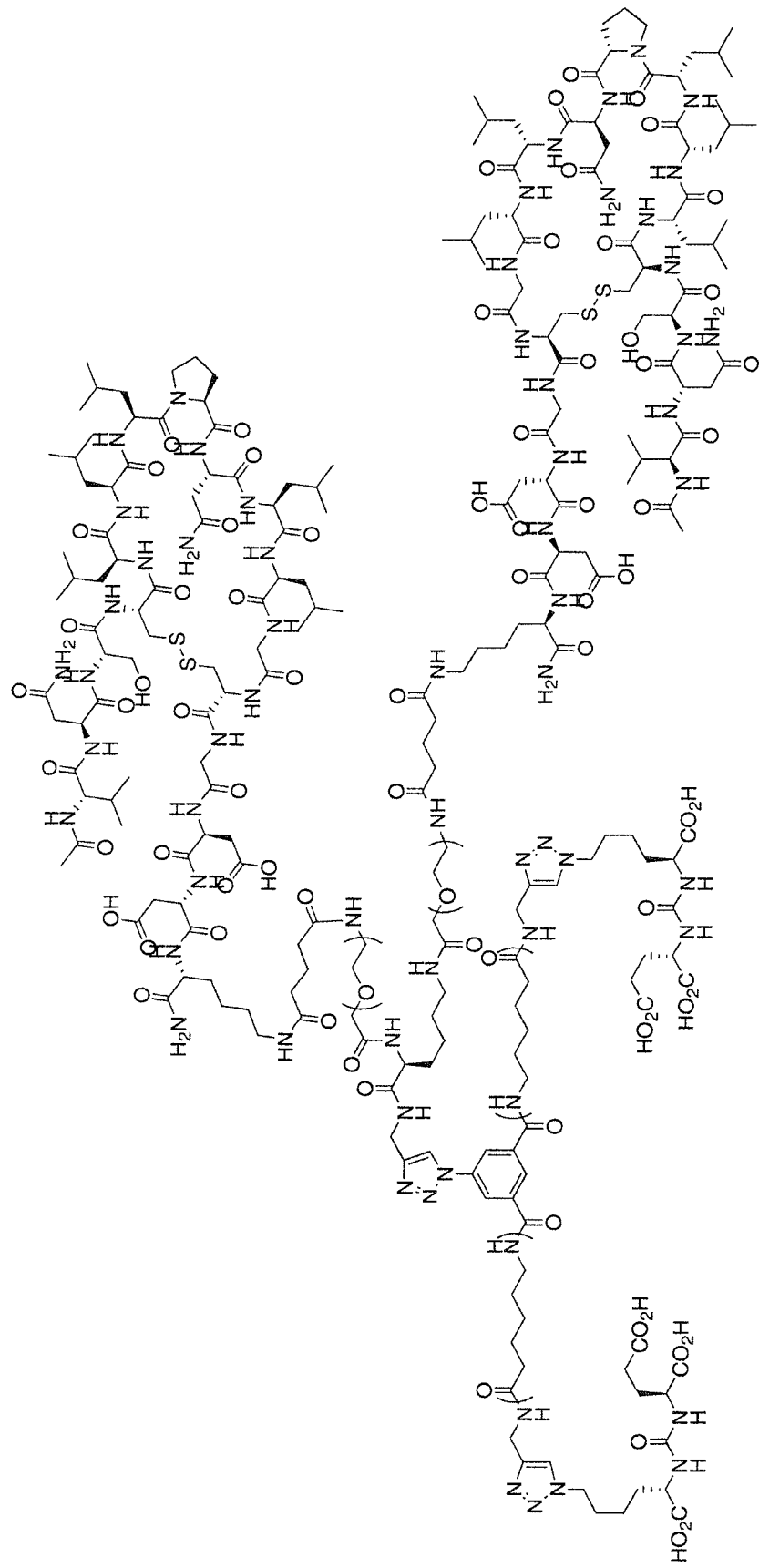
FIG. 22 shows the final product SyAM-P3.

The synthesis of SyAM-P2 proceeds pursuant to the reaction scheme which is presented in FIG. 17. Pursuant to that synthesis, the triester blocked glutamate-lysine dipeptide containing the azido group on the sidechain of lysine is reacted with amino end-capped polyethylene glycol containing an acetylenic group to form the intermediate CBT complex with a free amine (s-2 of FIG. 17). The free amine is reacted with the [MULTICON] moiety (s-3 of FIG. 17) to condense two CBT groups onto the [MULTICON] moiety S-3 as indicated in step b. The resulting intermediate comprises two CBT groups, a linker connecting the [CON] groups of X-2 to the [MULTICON] group (s-3) to provide intermediate S-4 (which can vary as to the substitution on the linker attached to triazole [CON] group) which can be condensed with intermediate 2-7 which contains a CP33 group linked to a dipeptide or oligopeptide. The dipeptide or oligopeptide may be end-capped to provide a non-reactive group or further reacted to provide a biotin moiety for diagnostic/experimental applications. S-7 in FIG. 17 links CP33 through an alanine-lysine-lysine tripeptide wherein the side chain of the distal lysine binds to the biotin moiety, but modifications of S-7 may be readily made. Alternatively, SyAM-P2 which avoids biotin can simply have the first lysine end-capped with a non-reactive group (e.g. amide) rather than extending the compound to another lysine to which is attached the biotin moiety. In the chemical synthesis of FIG. 17, the [IBT] group (CP33 containing intermediate S-7) is condensed onto the activated ester of intermediate s-4 to link the CP33 containing component to the [MULTICON] group to which are bonded the two CBT linker groups (s-2). This results in the final product SyAM-P2, which can contain a biotin group or other reporter component for diagnostics/analysis or can avoid the presence of a reporter component for use as a therapeutic agent in the treatment of prostate cancer as otherwise described herein.

SyAM-P3 (without Biotin)

This is the preferred compound pursuant to the present invention. This compound has two CBT groups and two IBT groups which are linked through a central {MULTICON] trifunctional 1,3,5-phenyl group. The synthesis of this compound begins with the preparation of the preferred CBT group (under the heading urea formation) pursuant to the chemical synthetic scheme which is presented in FIG. 17 hereof. The diester protected glutamate analog is first reacted with triphosgene followed by a di-protected lysine compound (the α-amino group remains unprotected) to form the tetra-protected intermediate which is hydrogenated (pd/C) to remove the Cbz protecting group at the sidechain amine position of lysine, which is converted to an azide moiety using TfN$_3$, copper sulfate and potassium carbonate to form the triprotected urea containing an azide moiety. This compound is the CBT synthon used in much of the synthesis of the present compounds because the azide can be condensed with an acetylenic group to readily form a triazole [CON] group which is directed bonded to the preferred [CBT] moiety in compounds according to the present invention.

In the same FIG. 17, the unnatural amino linker is prepared from the synthetic diprotected amino acid compound by removing the Boc group which protects the amine functionality in strong acid in dioxane, followed by condensing an amine protected amino acid onto the free amino of the amine-deprotected amino acid in 1-Ethyl-3-(3-dimethyllaminopropyl)carbodiimide hydrochloride (EDC), 1-hydroxybenzotriazole (HOBt) and N,N-diisopropylethyl amine (DIPEA) to provide the benzyl protected tripeptide. The terminal amine group of the resulting tripeptide is then protected (Fmoc) and the benzyl group is deprotected using hydrogenation conditions to afford the N-terminal protected linker tripeptide. This is the first linker.

The second linker is synthesized by condensing an acetylenic amine group onto the free carboxylic acid group of the di-N protected (Fmoc) lysine compound in the presence of EDC, HOBt and DIPEA. The resulting acetylenic protected lysine compound is then deprotected and reacted with the amine protected first linker obtained above to form the dilinker substituted acetylenic lysine intermediate which is deprotected (the two Fmoc groups are removed in diethylamine) and subsequently condensed with the azido dicarboxylic acid benzene analog. The benzene analog (which becomes the [MULTICON] group is then reacted with the benzyl-protected tripeptide linker in EDC, HOBt, DIPEA to form the phenyl azide containing two tripeptide linking groups. The azido-capped urea moiety [CBT] prepared above is condensed with the acetylenic amine compound to form the triazole [CON] group on the azide position having a methyleneamine group. This intermediate is reacted with the amine protected tripeptide linker to condense the tripeptide linker onto the free amine group of the triazole moiety. The protecting group (Fmoc) on the amine terminus of the tripeptide linker is removed with diethylamine. This intermediate is then condensed onto the dilinker azido phenyl [MULTICON] intermediate to provide two CBT linker groups which have been condensed onto the azido phenyl [MULTICON] intermediate. The azido group on the phenyl intermediate is condensed onto the acetylenic moiety of the second linker, prepared above to form a triazole group as the third group on the phenyl [MULTICON] moiety. This intermediate contains two CBT-linker groups on the phenyl [MULTICON] moiety and a triazole [CON] moiety on the [MULTICON] moiety. The triazole [CON] moiety also contains the two free amine-triethylene glycol linkers linked through lysine and end-capped with amine groups which can condense with CP33 to produce the final SyAM-P3 compound.

Figure 23:
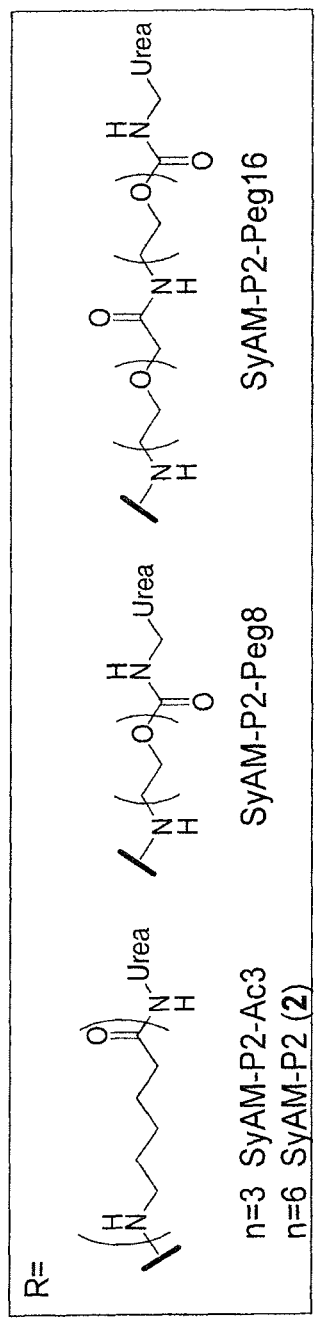
FIG. 23 shows an alternative linker strategy for the synthesis of SyAm-P2 compounds. The scheme shows the synthesis of SyAM-P2 using aminohexanoic acid polypeptide linkers, polyethylene glycol linkers and polyethylene glycol linkers which are further linked into extended linkers through an amide group.
Figure 23:
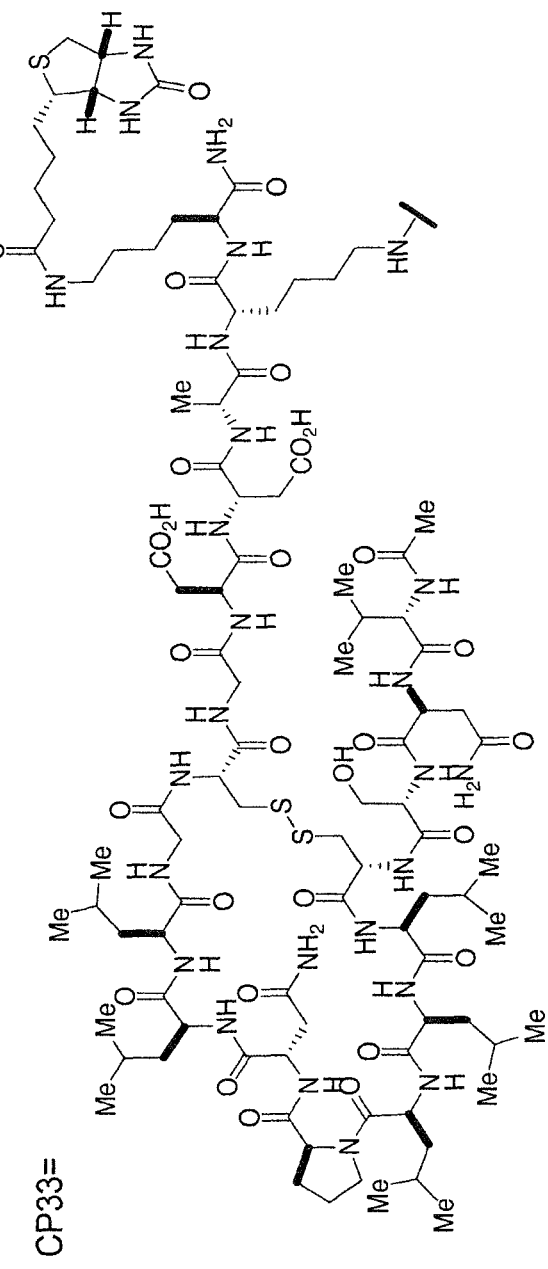
Figure 23:
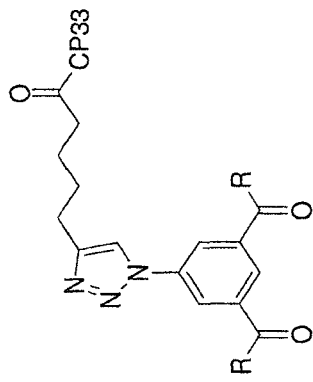

Accordingly, CP33 is prepared for condensation onto the two free amine groups by reacting a di-blocked lysine intermediate used in the preparation of the CBT urea group with the free carboxylic acid end of CP33 to form a lysine reacted CP33 intermediate which undergoes amination to form the free amide with the unreacted carboxylic acid group of lysine group. The free amine of lysine on the CP33-lysine intermediate is reacted with the disuccinimido diketo linker precursor to form the CP33-lysine linked intermediate containing a succinimide group (as a leaving group). Two of these CP33-lysine linked intermediates are condensed onto the previously prepared intermediate containing the two CBT groups which are linked through the [MULTICON]phenyl group and contain two free amine groups which readily condense onto the CP33-lysine linked intermediate containing the succinimido-activated ester group forming the final compound SyAM-P3 as set forth in FIG. 23.

Figure 24:
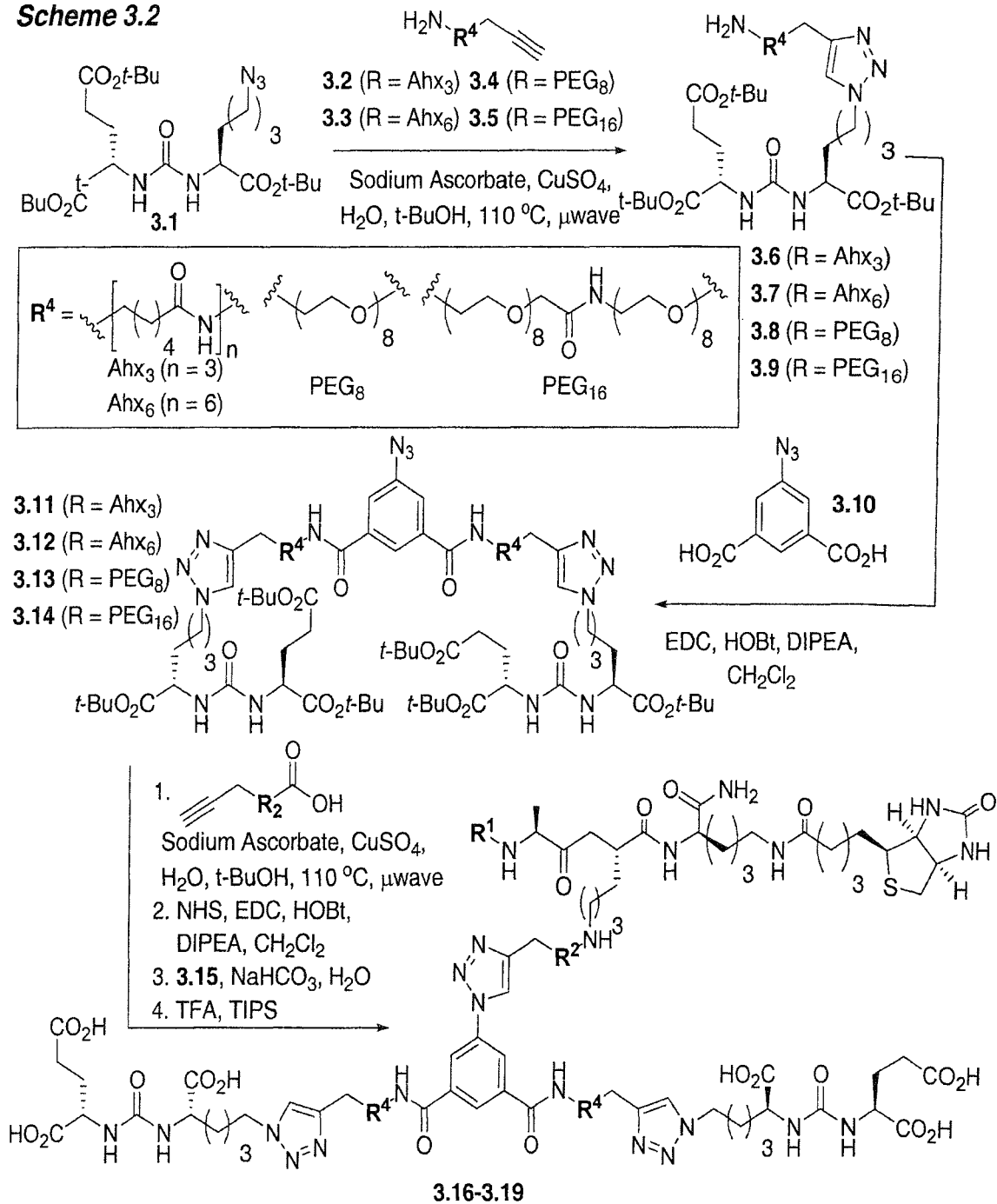
FIG. 24 shows chemical synthesis steps for SyAM-P2 using alternative linkers.

Alternative approaches to the synthesis of compounds according to the present invention are described in FIG. 24. FIG. 24 shows alternative syntheses of SyAM-P2 which can be applied to other compounds according to the present invention, utilizing alternative linkers as set forth in the figure. All of the reactions are straight forward and result in numerous compounds which can be seen to vary with respect to the linkers used.

Examples

General Information

Synthesis: All starting materials and reagents were purchased from commercially available sources and used without further purification. $^1$H NMR shifts are measured using the solvent residual peak as the internal standard (CDCl$_3$ d 7.26, MeOD d 3.31), and reported as follows: chemical shift, multiplicity (s=singlet, bs=broad singlet, d=doublet, t=triplet, dd=doublet of doublet, dt=doublet of triplet, q=quartet, m=multiplet), coupling constant (Hz), integration. $^{13}$C NMR shifts are measured using the solvent residual peak as the internal standard (CDCl$_3$ d 77.20, MeOD d 49.00, or DMSO d 39.52), and reported as chemical shifts. Infrared (IR) spectral bands are characterized as broad (br), strong (s), medium (m), and weak (w).

Abbreviations

AcOH=acetic acid
Acn=Acetonitrile
Ahx=Aminocaproic acid
AMC=7-amino-4-methylcoumarin
Boc=tert-butoxycarbonyl
BSA=bovine serum albumin
Cbz=benzyloxycarbonyl
DCM=dichloromethane
DIPEA=diisopropylethyl amine
DMF=N,N-dimethylformamide
DMSO=dimethylsulfoxide
DPBS=Dulbecco's phosphate-buffered saline
EDC=1-ethyl-3-(3-dimethylaminopropyl) carbodiimide
EDTA=ethylenediaminetetraacetic acid, disodium salt
EGTA=ethylene glycol-bis(2-aminoethyl)-N,N,N',N'-tetraacetic acid
EtOAc=ethyl acetate
Fmoc=9-fluorenylmethyloxycarbonyl
HI-FBS=heat inactivated fetal bovine serum
HOBt=hydroxybenzotriazole
iPrOH=isopropyl alcohol
MeCN=acetonitrile
MeOH=methanol
MTT=methyl-trityl
NHS=N-hydroxysuccinimide
NMP=N-methylpyrollidinone
Pbf=2,2,4,6,7-pentamethyldihydrobenzofuran-5-sulfony
Pd/C=10% palladium on carbon
Quant.=quantitative conversion
TBS=Tris-buffered saline
Tbu=tertbutyl
TEA=triethylamine.
TFA=trifluoroacetic acid
TFAA=trifuloroacetic anhydride
THF=tetrahydrofurane
TiPS=triisopropylsilane
Trt=trityl Solid Phase Peptide Synthesis General Procedure:

Solid-Phase Peptide Synthesis (SPPS) was performed in a CEM Discover Liberty Microwave Peptide Synthesizer. The amount of resin, amino acids, and reagents used in the synthesis were calculated using manufacture suggested protocols based on 0.1 mmol scale synthesis. Upon completion of SPPS, the resin was collected through vacuum filtration and rinsed several times with CH$_2$Cl$_2$. After drying in open air, the resin was then added to a flask containing either cleavage cocktail mixture (92:4.4 mixture of TFA:TIPS:H$_2$O) and gently stirred for the time specified below. Subsequently, the resin was filtered through a cotton-plugged pipet, and the filtrate was directly collected into a 50 mL conical tube containing 35 mL of cold (−78° C.) Et2O, at which point a white precipitate immediately formed. The suspension was re-cooled to −78° C. and then centrifuged at 4400 rpm for 5 minutes. After decanting the supernatant, the residual pellet was taken up in 50% MeCN/H$_2$O and purified using reverse-phase HPLC in 6-7 portions. The HPLC fractions were combined and lyophilized to give the corresponding peptides as white fluffy material.

Synthesis

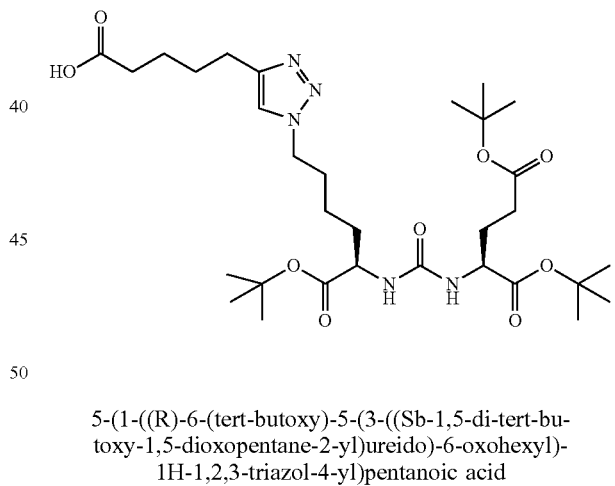

5-(1-((R)-6-(tert-butoxy)-5-(3-((Sb-1,5-di-tert-butoxy-1,5-dioxopentane-2-yl)ureido)-6-oxohexyl)-1H-1,2,3-triazol-4-yl)pentanoic acid A mixture of S.1 (98 mg, 0.191 mmol, 1.0 equiv.) and heptynoic acid (120 mg, 0.954 mmol, 5 eq.) was dissolved in a mixture of H$_2$O (1.25 mL) and t-BuOH (1.25 mL) in a 5 mL □wave reaction tube. To this mixture was added 0.1 M sodium ascorbate (0.059 mmol, 0.2 equiv.) and 0.1 M copper (11) sulfate (0.012 mmol, 0.04 equiv.). The tube was capped, and subjected to □wave irradiation for 10 minutes at 110° C. The reaction was then concentrated under reduced pressure, and chromatographed (1×15 cm silica gel, 20% MeOH in CHCl$_3$, then 20% MeOH in CHCl$_3$+1% TFA) to yield s-x as a colorless oil calc'd for C$_{31}$H$_{53}$N$_5$O$_9$(M+H) 640.7806 found.

SyAM-P1

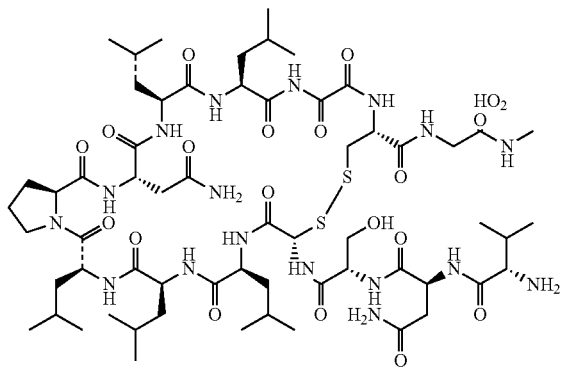

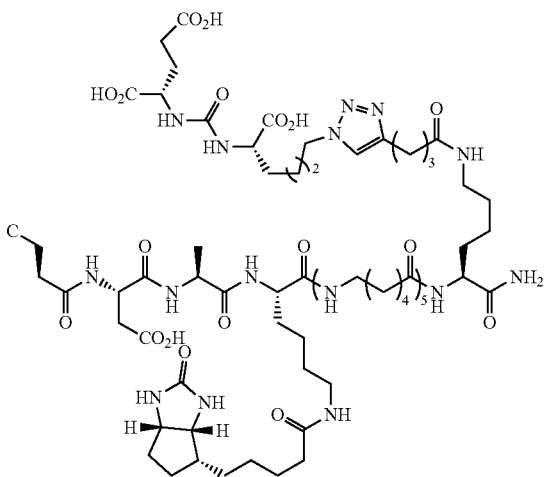

Standard solid phase peptide synthesis 0.1 mmol scale of Fmoc-VNS(Tbu)C(Trt)LLLPN(Trt)LLGC(Trt)GD(Tbu)D(Tbu)K(biotin)-Ahx$_5$-Lys(MTT)-G-Resin. While on resin Mtt group deprotected using 1% TFA in DCM 5 mL while on rotator for 5 minutes, repeat three times, a yellow supernatant washed away. Resin neutralized washing with DMF 0.1 mM DIPEA. Sx (160 mg, 0.25 mmol, 2.5 eq) dissolved in 3 mL of DMF and added to resin with HBTU (95 mg, 0.25 mmol, 2.5 eq) along with 86 uL of DIPEA (64 mg, 5 mmol, 5 eq). Mixture subjected to µwave irradiation for 10 minutes at 75c. Resin washed 3× with DMF and Fmoc group deprotected with 20% piperidine in DMF for 20 minutes RT. Global deprotection and cleavage from solid support performed with 92:4:4 mixture of TFA:H$_2$O:TIPS for 90 minutes stirring at room temperature. Subsequently, the resin was filtered through a cotton-plugged pipet, and the filtrate was directly collected into a 50 mL conical tube containing 35 mL of cold (−78° C.) Et2O, at which point a white precipitate immediately formed. The suspension was re-cooled to −78° C. and then centrifuged at 4400 rpm for 5 minutes. After decanting the supernatant, the residual pellet was taken up in 25 mL of 20% ACN/H$_2$O and 1 mL of DMSO and 40 mg of potassium carbonate added and stirred in air for 48 hours to oxidize to disulfide. After oxidation peptide was purified using reverse-phase HPLC.

HRMS (ES+) calc'd for $C_{142}H_{238}N_{36}O_{41}S_3$(M+3H) m/z 1601.91 found (M+3H) 1601.53

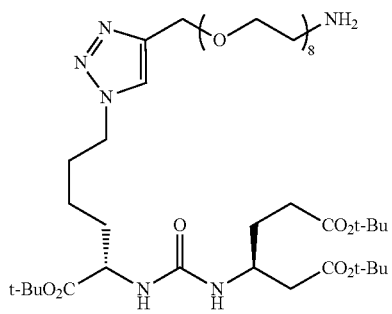

(S)-di-tert-butyl 2-(3-((S)-6-(4-(25-amino-2,5,8,11,14,17,20,23-octaoxapentacosyl)-1H-1,2,3-triazol-1-yl)-1-(tert-butoxy)-1-oxohexan-2-yl)ureido)pentanedioate (s-2)

A mixture of s-1 (152 mg, 0.295 mmol, 1.0 equiv.) and 3,6,9,12,15,18,21,24-octaoxaheptacos-26-yn-1-amine (120 mg, 0.295 mmol, 1.0 equiv.) was dissolved in a mixture of H$_2$O (1.1 mL) and t-butanol (1.1 mL) in a 5 mL µwave reaction tube. To this mixture was added 0.1 M sodium ascorbate (0.6 mL, 0.2 equiv.) and 0.1 M copper(II) sulfate (0.12 mL, 0.04 equiv.). The tube was capped, and subject to µwave radiation for 2.5 minutes at 110° C. The reaction was then concentrated under reduced pressure, and chromatographed (1×15 cm silica gel, 10% MeOH in CH$_2$Cl$_2$, then 10% MeOH in CH$_2$Cl$_2$+2.5% Et$_3$N) to yield s-2 (254 mg, 80%) as a brown oil. IR (thin film) 2869 (m), 1729 (s), 1680 (w), 1534 (m), 1456 (w), 1367 (m), 1252 (w), 1152 (s), 1113 (s) cm-1. 1HNMR (400 MHz, CDCl3) δ 7.71 (s, 1H), 5.32 (d, J=8 Hz, 1H), 5.25 (d, J=8 Hz, 1H), 4.72-4.64 (dd, J=8 Hz, XX Hz, 2H), 4.38-4.28 (m, 4H), 3.68-3.64 (m, 30H), 2.98-2.93 (m, 2H), 2.35-2.28 (m, 2H), 2.08-2.05 (m, 1H), 1.97-1.77 (m, 4H), 1.65-1.59 (m, 1H), 1.46 (s, 9H), 1.43 (s, 18H), 1.49-1.27 (m, 2H). 13CNMR (100 MHz, CDCl3) δ 172.5, 172.1, 156.9, 145.0, 123.0, 81.9, 81.9, 90.5, 70.6, 70.5, 70.5, 70.5, 70.4, 70.4, 70.4, 70.2, 69.6, 64.6, 53.1, 53.0, 49.9, 32.3, 31.7, 29.6, 28.3, 28.1, 28.1, 28.0, 21.9. HRMS (ES+) calc'd for $C_{43}H_{80}N_6O$ (M+H) m/z 921.5754 Found 921.5754.

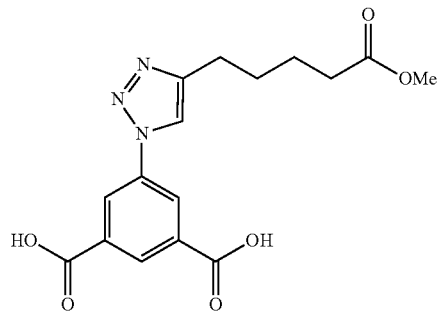 [SMILES: COC(=O)CCCCc1cn(-c2cc(C(=O)O)cc(C(=O)O)c2)nn1]

5-(4-(5-methoxy-5-oxopentyl)-1H-1,2,3-triazol-1-yl) isophthalic acid (s-3)

A mixture of azidoisophthalic acid (100 mg, 0.483 mmol, 1.0 equiv.) and methyl hept-6-ynoate (100 mg, 0.714 mmol, 1.45 equiv.) was dissolved in a mixture of H$_2$O (1.7 mL) and t-BuOH (1.7 mL) in a 5 mL μwave reaction tube. To this mixture was added 0.1 M sodium ascorbate (0.059 mmol, 0.2 equiv.) and 0.1 M copper (II) sulfate (0.012 mmol, 0.04 equiv.). The tube was capped, and subjected to μwave irradiation for 2.5 minutes at 110° C. The reaction was then concentrated under reduced pressure, and chromatographed (1×15 cm silica gel, 20% MeOH in CHCl$_3$, then 20% MeOH in CHCl$_3$+1% TFA) to yield s-3 as a beige colored solid. IR (thin film) 3151 (w), 2951 (w), 1721 (s), 1604 (w), 1463 (w), 1291 (m), 1248 (m), 1071 (m) cm-1. 1HNMR (400 MHz, MeOD) d 8.70 (s, 1H), 8.66 (s, 2H), 8.51 (s, 1H), 3.66 (s, 3H), 2.83 (t, J=7.4 Hz, 2H), 2.41 (t, J=6.8 Hz, 2H), 1.81-1.70 (m, 4H). 13CNMR (100 MHz, DMSO-d$_6$) δ 173.3, 165.9, 148.3, 137.2, 133.5, 129.1, 123.7, 120.6, 118.0, 51.2, 33.0, 27.9, 24.7, 24.0. HRMS (ES+) calc'd for C$_{16}$H$_{17}$N$_3$O$_6$ (M+H) m/z 348.1190 Found 348.1184.

0.133 mmol, 2.2 equiv.) in 1 mL of dry CH$_2$Cl$_2$ and pyridine (15 uL, 0.181 mmol, 3 equiv.). The reaction was allowed to stir at room temperature for 13 hours, after which it was concentrated under reduced pressure at 37° C. and chromatographed (silica gel, 2×15 cm, 5% MeOH in CHCl$_3$) to give s-4 as a pale brown oil (90 mg, 73%). IR (thin film) 2867 (w), 2405 (br), 1728 (s), 1661 (m), 1456 (s), 1367 (m), 1250 (w), 1149 (s), 1098 (s), 846 (w) cm-1. 1HNMR (500 MHz, MeOD) δ 8.50 (s, 1H), 8.50 (s, 1H), 8.42 (t, J=1.5 Hz, 1H). 7.96 (s, 2H). 6.36-6.33 (dd. J=4, 4.5 Hz, 3H), 4.60 (s. 4H), 4.40 (t, J=7.5 Hz, 4H), 4.22-4.11 (m, 4H), 3.70 (t, J=5.5 Hz, 4H), 3.67-3.54 (m, 66H), 2.83 (t, J=7 Hz, 2H), 2.40 (t, J=7 Hz, 2H), 2.37-2.27 (m, 4H), 2.07-2.00 (m, 2H), 1.96-1.89 (m, 4H), 1.84-1.70 (m, 8H), 1.69-1.61 (m, 2H), 1.47 (s, 19H), 1.44 (s, 21H), 1.41 (s, 17H), 1.40-1.34 (m, 4H). 13CNMR (100 MHz, MeOD) δ 175.6, 173.7, 173.6, 173.4, 167.9, 159.9, 150.1, 146.0, 138.7, 138.0, 127.4, 125.0,

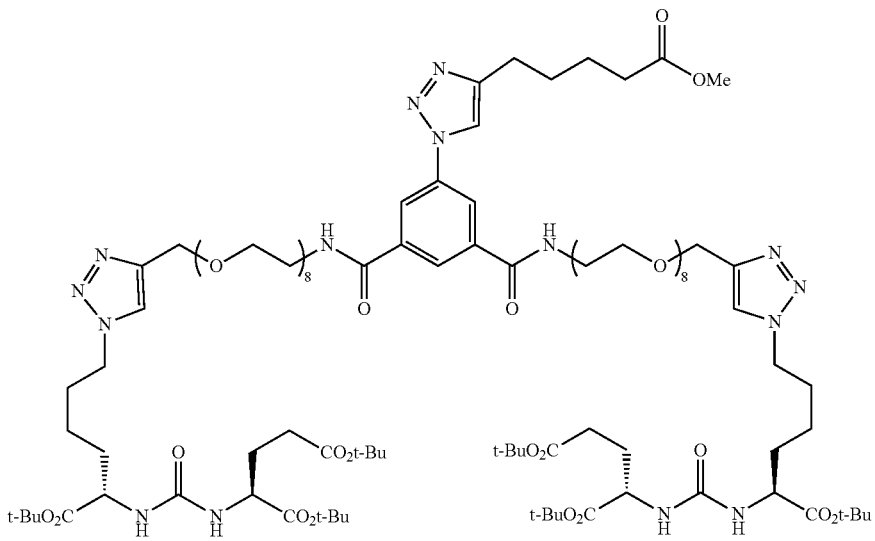

s-4

To a solution of s-3 (20 mg, 0.06 mmol, 1 equiv.) in 1 mL of dry CH$_2$Cl$_2$ in a flame dried round bottom flask was added EDC (29 mg, 0.15 mmol, 2.5 equiv.) and HOBt (23 mg, 0.15 mmol, 2.5 equiv.), followed by a solution of s-2 (122 mg, 122.8, 121.8, 82.8, 82.6, 81.7, 71.6, 71.6, 71.5, 71.3, 70.8, 70.4, 65.0, 54.7, 54.1, 52.1, 51.1, 41.3, 34.4, 32.9, 32.5, 30.8, 29.8, 29.0, 28.4, 28.3, 26.0, 23.5. HRMS (ES+) calc'd for C$_{102}$H$_{73}$N$_{15}$O$_{34}$ (M+H) 2153.2369 Found (M+2H) m/z 1077.1271.

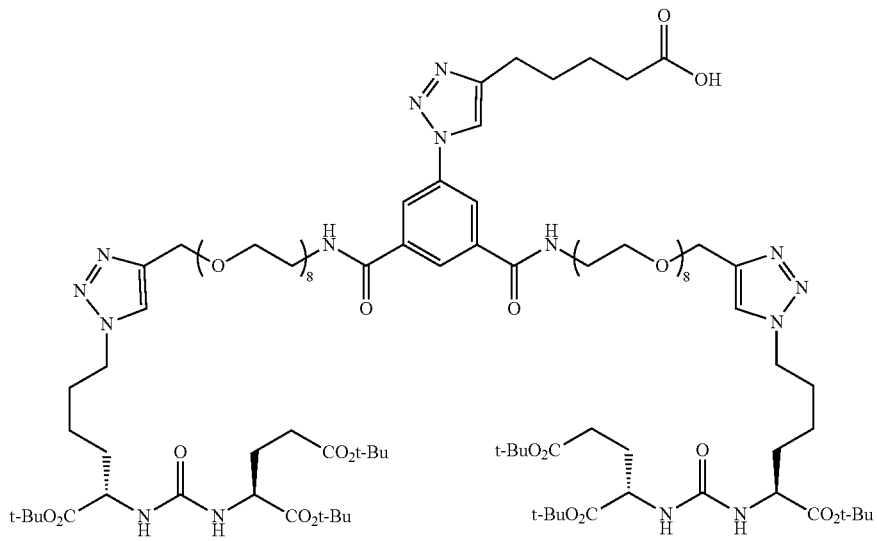

s-5 s-4 (90 mg, 0.042 mmol, 1 equiv.) was dissolved in MeOH (1 mL). To this solution was added 1 M LiOH in H₂O (4 equiv.). The reaction was allowed to stir at room temperature for 2 hours, after which another 4 equiv. of 1 M LiOH in H₂O was added. The reaction was allowed to stir at room temperature fore another 2 hours, after which it was neutralized with 6 equiv. of 1 M HCl in H₂O. The reaction was concentrated and chromatographed (1×15 cm silica gel, 20% MeOH in CHCl₃). The fractions containing product were concentrated and taken up with 80% MeCN in H₂O and purified using HPLC (C18 reverse phase, 5 mL/min, 50%-75% MeCN in H₂O over 40 minutes). The product was isolated and lyophilized to give a s-5 as a white powder (10 mg, 12%). IR (thin film) 3341 (br), 3108 (w), 2931 (m), 1729 (s), 1667 (s), 1556 (w), 1457 (w), 1151 (s) cm-1. 1HNMR (500 MHz, MeOD) δ 8.73 (t, J=5.5 Hz, 1H), 8.51 (s, 3H), 8.42 (s, 1H), 7.97 (s, 2H), 4.64 (s, 1H), 4.60 (s, 4H), 4.41 (t, J=7.2 Hz, 4H), 4.18 (dd, J=5.9 Hz, 2H), 4.13 (dd, J=5, 8 Hz, 2H), 4.06 (s, 1H), 4.01 (s, 1H), 3.99-3.96 (m, 1H), 3.74-3.55 (m, 80H), 3.48-3.44 (m, 1H), 3.17-3.13 (m, 6H), 2.84 (t, J=7.2 Hz, 2H), 2.66 (s, 1H), 2.39-2.29 (m, 6H), 2.07-2.00 (m, 2H), 1.96-1.89 (m, 4H), 1.84-1.76 (m, 6H), 1.75-1.70 (m, 2H), 1.69-1.61 (m, 2H), 1.60-1.52 (m, 2H), 1.48-1.41 (m, 4H), 1.47 (s, 18H), 1.44 (s, 18H), 1.43 (s, 18H), 1.40-1.30 (m, 6H). 13CNMR (125 MHz, MeOD) δ 177.2, 173.7, 173.7, 173.4, 168.0, 159.9, 138.8, 138.0, 127.4, 125.0, 122.7, 121.8, 82.8, 81.8, 71.5, 71.4, 71.4, 71.4, 71.3, 70.7, 70.5, 65.0, 54.7, 54.2, 41.3, 34.6, 32.9, 32.5, 30.8, 29.8, 29.0, 28.4, 28.3, 26.1, 25.5, 23.5. HRMS (ES+) calc'd for C₁₀₁H₁₇₁N₁₅O₃₄ (M+H) m/z 2139.2213 Found (M+2H) m/z 1070.1426.

cp33-Bis(Peg8-Urea)

s-5 (45 mg, 0.021 mmol, 1.0 equiv.) was dissolved in CH2Cl2. EDC, HOBt, and N-hydroxysuccinimide were added sequentially, followed by DIPEA, and the reaction was allowed to stir at room temperature for 6 hours, after which conversion was observed via LCMS. The reaction was concentrated, and a mixture of 95% TFA, 2.5% PBS, 2.5% TIPS was added. The reaction was allowed to stir for 30 minutes, after which it was concentrated. 1 mL of PBS and 1.5 mL of a saturated sodium bicarbonate solution was added immediately to the flask, followed by cp33 peptide (16 mg, 0.007 mmol, 0.3 equiv.). The reaction was allowed to stir at room temperature for 12 hours, and subsequently purified by HPLC (C18 reverse phase, 5 mL/min, 30%-42% MeCN in H₂O over 66 minutes). The fractions containing product were collected and lyophilized to give a white powder (1.2 mg, 11.2%).

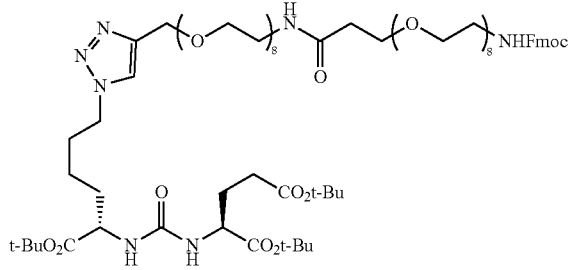

(S)-di-tert-butyl 2-(3-(((S)-6-(4-(1-(9H-fluoren-9-yl)-3,31-dioxo-2,7,10,13,16,19,22,25,28,35,38,41,44,47,50,53,56-heptadecaoxa-4,32-diazaheptapentacontan-57-yl)-1H-1,2,3-triazol-1-yl)-1-(tert-butoxy)-1-oxohexan-2-yl)ureido)pentanedioate (s-6)

s-2 (90 mg, 0.135 mmol, 1 equiv.) was dissolved in 1 mL of dry CH₂Cl₂ in a flame dried flask, and EDC·HCl (29 mg, 0.15 mmol, 1.1 equiv.) and HOBt H2O (23 mg, 0.15 mmol, 1.1 equiv) were sequentially added, followed by a solution of Fmoc-N-amido-dPEG8-acid (Quanta Biodesign Ltd. 138 mg, 0.15 mmol, 1.1 equiv.) in 1 mL of dry CH₂Cl₂ and DIPEA (28 uL, 0.162 mmol, 1.2 equiv.). The reaction was allowed to stir for 2.5 hours, after which 1 mL of MeOH was added. The reaction was then concentrated under reduced pressure and chromatographed (silica gel, 1×15 cm, 2.5% MeOH in CHCl₃, then 5% MeOH in CHCl₃, then 10% MeOH in CHCl₃) to yield s-6 as a clear oil (149 mg, 70%). IR (thin film) 3332 (br), 2868 (m), 1727 (m), 1672 (w), 1547 (m), 1451 (w), 1367 (w), 1251 (m), 1149 (s), 1110 (s) cm-1. 1HNMR (500 MHz, CDCl3) δ 7.75 (d, J=7.5 Hz, 2H) 7.62 (s, 1H), 7.61 (d, J=7.5 Hz, 2H), 7.39 (t, J=7.5 Hz, 2H), 7.31 (t, J=7.5 Hz, 2H), 6.63 (s, 1H), 5.42 (s, 1H), 5.24 (d, J=8 Hz, 1H), 5.15 (d, J=8 Hz, 1H), 4.67 (dd, J=10 Hz, 25 Hz, 2H), 4.40 (d, J=7 Hz, 2H), 4.37-4.27 (m, 4H), 4.22 (t, J=7 Hz, 1H), 3.72 (t, J=6 Hz, 2H), 3.68-3.55 (m, 66H), 3.54 (t, J=5 Hz, 2H), 3.43 (dd, J=5.5, 12 Hz, 2H), 3.39 (dd, J=5.5, 12 Hz, 2H), 2.46 (t, J=6 Hz, 2H), 2.37-2.24 (m, 2H) 2.10-2.03 (m, 2H), 1.95-1.76 (m, 5H), 1.64-1.57 (m, 1H), 1.46 (s, 9H), 1.43 (s, 18H), 1.39-1.29 (m, 2H). 13CNMR (100 MHz, CDCl3) δ 172.4, 172.1, 172.1, 171.4, 156.8, 145.1, 144.0, 141.3, 127.7, 127.0, 125.1, 122.9, 120.0, 81.9, 81.9, 80.6, 70.6, 70.6, 70.6, 70.5, 70.4, 70.4, 70.3, 70.3. 70.1, 69.9, 69.6, 67.3, 66.6, 64.6, 53.1, 53.0, 49.9, 47.3, 41.0, 39.2, 37.0, 32.4, 31.7, 29.6, 28.3, 28.1, 28.1, 28.0, 21.8. HRMS (ES+) calc'd for $C_{77}H_{127}N_7O_{26}$ (M+H) m/z 1566.8904 Found 1566.8892.

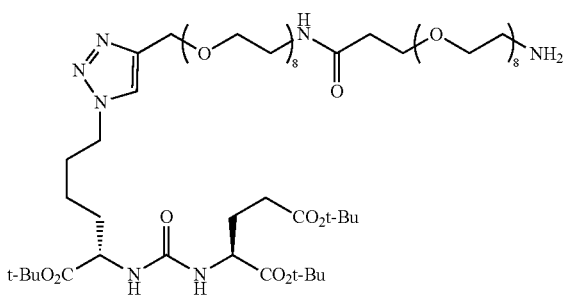

(S)-di-tert-butyl 2-(3-(S)-6-(4-(53-amino-27-oxo-2, 5,8,11,14,17,20,23,30,33,36,39,42,45,48,51-hexadecaoxa-26-azatripentacontyl)-1H-1,2,3-triazol-1-yl)-1-(tert-butoxy)-1-oxohexan-2-yl)ureido) pentanedioate (s-7)

s-6 (135 mg) was dissolved in 3 mL of $Et_2NH$ and 3 mL of $CH_2Cl_2$. The reaction was allowed to stir at room temperature for 3 hours, after which it was concentrated under reduced pressure and chromatographed (silica gel, 2×15 cm, 2.5% MeOH in $CHCl_3$, then 5% MeOH in $CHCl_3$, then 10% MeOH in $CHCl_3$, then 20% MeOH in $CHCl_3$, then 20% MeOH in $CHCl_3$, +2.5% $Et_3N$) to yield s-7 as a clear oil (86 mg, 75%). IR (thin film). 1HNMR (400 MHz, MeOD) δ 8.01 (s, 1H), 4.64 (s, 2H), 4.42 (t, J=7.2 Hz, 3H), 4.20-4.17 (m, 1H), 4.15-4.11 (m, 1H), 3.77-3.63 (m, 72H), 3.54 (t, J=5.6 Hz, 2H), 3.37 (t, J=5.6 Hz, 2H), 3.14 (t, J=5.2 Hz, 2H), 3.00 (dd, J=7.2, 15.2 Hz, 1H), 2.61 (t, J=6 Hz, 1H), 2.48 (t, J=6 Hz, 2H), 2.38-2.25 (m, 2H), 2.08-2.00 (m, 1H), 1.98-1.90 (m. 2H), 1.85-1.74 (m, 2H), 1.70-1.60 (m, 1H), 1.48 (s, 9H), 1.44 (s, 18H), 1.40-1.36 (m, 2H), 1.29 (t, J=7.2 Hz, 2H). 13CNMR (100 MHz, MeOD) δ 173.9, 173.8, 173.7, 173.5, 159.9, 146.0, 125.1, 82.8, 82.7, 81.8, 71.6, 71.5, 71.5, 71.4, 71.4, 71.4, 71.3, 71.3, 71.2, 71.2, 71.1, 71.1, 70.8, 70.7, 70.6, 68.5, 68.3, 67.6, 65.0, 54.7, 54.2, 52.2, 51.1, 43.7, 40.8, 40.5, 37.5, 35.7, 32.9, 32.5, 30.9, 29.0, 28.4, 28.4, 23.5. HRMS (ES+) calc'd for $C_{62}H_{117}N_7O_{24}$ (M+H) m/z 1344.8223 Found 1344.8251.

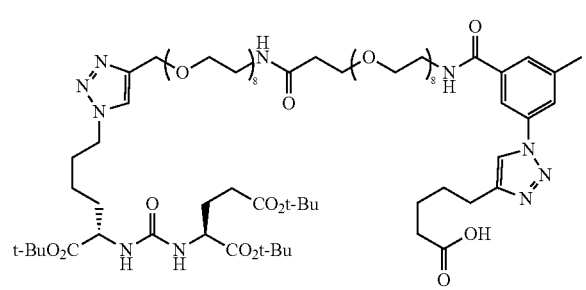

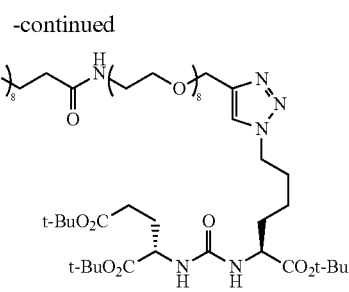

s-8 s-3 (8 mg, 0.023 mmol, 1.0 equiv.) was dissolved in $CH_2Cl_2$ (1 mL). To this solution were added EDC·HCl (15 mg, 0.076 mmol, 3.3 equiv.), HOBt·$H_2O$ (12 mg, 0.076 mmol, 3.3 equiv.), and a solution of s-7 (102 mg, 0.076 mmol, 3.3 equiv.) in $CH_2Cl_2$ (4 mL). Pyridine (5.5 mg, 5.7 μL, 0.7 mmol, 3.0 equiv.), was added, and the reaction was allowed to proceed at room temperature for 16 hours, after which it was concentrated and partially purified (1×15 cm, silica gel, 10% MeOH in $CHCl_3$). The fractions containing product was concentrated and immediately taken up with MeOH (1 mL). 1 M LiOH in $H_2O$ (92 ILL, 0.092 mmol, 4 equiv.) was added to the solution, and the reaction was allowed to stir at room temperature for 3 hours, after which 1 M LiOH in $H_2O$ (92 μL, 0.092 mmol, 4 equiv.) was added. The reaction was allowed to stir at room temperature for an additional 2 hours, after which it was neutralized with 1 M HCl in $H_2O$ (138 mL, 0.138 mmol, 6.0 equiv.). The reaction was concentrated, taken up with 80% MeCN in $H_2O$, and purified by HPLC (reverse phase, C18, 5 mL/min, 50%-75% MeCN in $H_2O$ over 40 minutes). The product was isolated and lyophilized to yield s-8 as a white powder (8 mg). IR (thin film) 2873 (m), 1729 (m), 1666 (s), 1555 (w), 1456 (w), 1368 (w), 1140 (s) 950 (w), 846 (w) cm-1. 1HNMR (500 MHz, MeOD) δ 8.72 (t, J=5.2 Hz, 1H), 8.51 (s, 3H), 8.42 (s, 1H), 7.99 (s, 2H), 7.90 (s), 3H), 4.62 (s, 4H), 4.41 (t, J=7 Hz, 4H), 4.18 (dd, J=5, 7.2 Hz, 2H), 4.13 (dd, J=5, 6 Hz, 2H), 3.71-3.69 (m, 10H), 3.66-3.57 (m, 118H), 3.52 (t, J=5.5 Hz, 4H), 3.36-3.34 (m, 8H), 2.84 (t, J=6 Hz, 2H), 2.44 (t, J=6.2 Hz, 4H), 2.37 (t, J=7.2 Hz, 2H), 2.33-2.28 (m, 4H), 2.06-2.00 (m, 2H), 1.96-1.90 (m, 4H), 1.83-1.77 (m, 6H), 1.75-1.68 (m, 2H). 1.67-1.63 (m, 2H), 1.46 (s, 18H), 1.44 (s, 18H), 1.43 (s, 18H), 1.39-1.34 (m, 4H). 13CNMR (125 MHz, MeOD) δ 177.2, 174.0, 173.7, 173.7, 173.5, 167.9, 159.9, 150.2, 146.0, 138.8, 138.0, 127.4, 125.1, 122.8, 121.8, 82.8, 82.7, 81.8, 79.5, 71.5, 71.5, 71.5, 71.4, 71.4, 71.4, 71.3, 71.3, 71.3, 70.7, 70.6, 70.5, 68.3, 65.0, 54.7, 54.2, 51.1, 41.3, 40.4, 37.5, 34.6, 32.9, 32.5, 30.8, 29.8, 29.0, 28.4, 28.3, 28.3, 26.1, 25.5, 25.3, 23.5. HRMS (ES+) calc'd for $C_{139}H_{45}N_{17}O_{52}$ (M+H) m/z 2985.7150 Found (M+2H) m/z 1493.3458.

s-9 s-8 (22 mg, 0.0074 mmol, 1.0 equiv.) was dissolved in 1 mL of DMF. To this solution was added EDC (14.2 mg, 0.074 mmol, 10.0 equiv.), HOBt (11.3 mg, 0.074 mmol, 10.0 equiv.), and NHS (8.5 mg, 0.074 mmol, 10.0 equiv.) sequentially, followed by DIPEA (13.0 μL, 0.074 mmol, 10.0 equiv.). The reaction was allowed to stir at room temperature for 13 hours, after which the DMF was removed by passing a steady stream of N2 over the reaction. A mixture of 97.5% TFA/2.5% TIPS was added to the flask, and the reaction was allowed to stir for 1 hour, after which the TFA was removed under reduced pressure. The crude reaction mixture was purified by HPLC (Sunfire™ Prep C18 column (10×150 mm) using a 50% MeCN to 80% MeCN in H2O gradient over 66 min at 5 mL/min) to give s-9 as a white powder (2.5 mg), which was immediately used for the next step.

cp33-Bis(Peg16-Urea)

s-9 (2.5 mg, 0.9 μmol, 1.0 equiv.) was dissolved in 2 mL of PBS and 1 mL of saturated sodium bicarbonate in water. cp33 peptide (2.5 mg, 0.11 mmol, 1.2 equiv.) was added, and the reaction was allowed to stir at room temperature for 4 hours, after which it was injected directly onto the HPLC and purified (Sunfire™ Prep C18 column (10×150 mm) using a 30% MeCN to 42% MeCN in H2O gradient over 39 min at 5 mL/min). The fractions containing the product were isolated and lyophilized to give a white powder (1.4 mg, 32.5%).

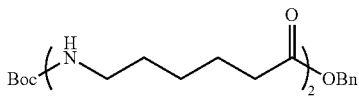

benzyl 6-(6-((tert-butoxycarbonyl)amino)hexanamido)hexanoate (s-9)

6-((tert-butoxycarbonyl)amino)hexanoic acid (2.58 g, 11.15 mmol, 1.1 equiv.) was dissolved in 50 mL of DCM. To the solution were added EDC·HCl (2.14 g, 11.15 mmol, 1.1 equiv.), HOBt·H2O (1.71 g, 11.15 mmol, 1.1 equiv.), and a solution of benzyl 6-aminohexanoate (2.24 g, 10.14 mmol, 1.0 equiv.) in CH2Cl2 (50 mL). DIPEA (2.0 mL, 11.15 mmol, 1.1 equiv.) was added, and the solution was allowed to stir at room temperature for 90 min, after which the reaction was washed with 10% Citric Acid (100 mL), saturated NaHCO3 (100 mL), and brine (100 mL). The organic layer was collected, dried with MgSO4, and concentrated to give s-9 (3.17 g, 73% crude) as a white powder, which was carried on without any further purification.

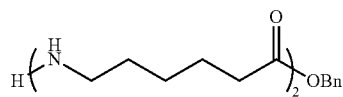

benzyl 6-(6-aminohexanamido)hexanoate (s-10)

s-9 (3.1 g) was dissolved in 15 mL of TFA and stirred at room temperature for 1 hour, after which the TFA was partially removed under reduced pressure. The resulting oil was washed with 150 mL of diethyl ether, and the ether was carefully decanted into 50 mL centrifuge tubes. The centrifuge tubes were spun down at 3.0 rcf for 10 minutes, resulting in the product settling to the bottom, and the ethereal layer was carefully removed. The products were combined with methanol, concentrated down under reduced pressure, and azeotroped with deuterated chloroform to yield s-10 as a green oil (2.27 g, 92% crude), which was carried on without purification.

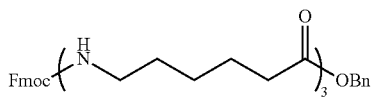

benzyl 1-(9H-fluoren-9-yl)-3,10,17-trioxo-2-oxa-4,11,18-triazatetracosan-24-oate (s-11)

6-((((9H-fluoren-9-yl)methoxy)carbonyl)amino)hexanoic acid (2.39 g, 6.78 mmol, 1 equiv.) was dissolved in CH2Cl2 (35 mL). To this solution was added EDC·HCl (1.56 g, 8.14 mmol, 1.2 equiv.), and HOBt·H2O (1.25 g, 8.14 mmol, 1.2 equiv.). In a separate flask, s-10_(2.27 g, 6.78 mmol, 1 equiv.) was dissolved in CH2Cl2 (40 mL), and DIPEA (3 mL, 17 mmol, 2.5 equiv.) was added to neutralize leftover TFA. This solution was added to the original reaction, and the flask was washed with an additional 10 mL of CH2Cl2, which was also added to the original reaction. The reaction mixture was stirred for 75 minutes at room temperature, after which it was washed with 10% Citric acid (100 mL), saturated sodium bicarbonate (100 mL), and saturated brine (100 mL). The organic layer was collected, dried with MgSO4, concentrated under reduced pressure, and partially purified (silica gel, 3×25 cm, 5% MeOH in CHCl3, then 10% MeOH in CHCl3) to remove coupling reagents. The fractions containing the product were collected and chromatographed a second time (50% MeCN in CHCl3+2.5% DIPEA) to yield a white solid, which was chromatographed a third time (5% MeOH in CHCl3, then 10% MeOH in CHCl3) to yield s-11 as a pure, white solid (1.5 g, 33%, 3 steps). IR (thin film) 3306 (br), 2936 (m), 2861 (w), 1719 (s), 1647 (s), 1544 (s), 1450 (m), 1254 (s), 1160 (m), 741 (m) cm-1. 1HNMR (400 MHz, MeOD) δ 7.80 (d, J=8 Hz, 2H), 7.64 (d, J=8 Hz, 2H), 7.39 (t, J=8 Hz, 2H), 7.35-7.32 (m, 5H), 7.30 (t, J=8 Hz, 2H), 5.10 (s, 2H), 4.33 (d, J=6.4 Hz, 2H), 4.21 (t, J=7.2 Hz, 1H), 3.16-3.08 (m, 6H), 2.36 (t, J=7.2 Hz, 2H), 2.19-2.13 (m, 4H), 1.65-1.58 (m, 6H), 1.53-1.46 (m, 6H), 1.36-1.30 (m, 6H). 13CNMR (100 MHz, MeOD) δ 176.0, 175.0, 158.9, 145.3, 142.6, 137.7, 129.5, 129.2, 128.8, 128.1, 126.2, 120.9, 67.6, 67.1, 41.6, 40.2, 40.1, 37.0, 37.0, 34.9, 30.6, 30.0, 27.5, 27.4, 27.4, 26.7, 25.7. HRMS (ES+) calc'd for $C_{40}H_{51}N_3O_6$ (M+H) m/z 670.3850 Found 670.3847.

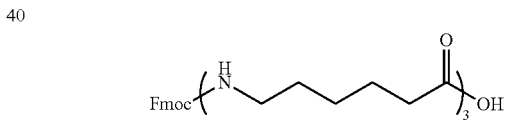

1-(9H-fluoren-9-yl)-3,10,17-trioxo-2-oxa-4,11,18-triazatetracosan-24-oic acid (s-12)

s-11 was taken up with 90% iPrOH/10% MeOH (30 mL) and added to a slurry of 10% Pd/C in 10 mL of 90% iPrOH/10% MeOH. 40 mL of 90°/c iPrOH/10% MeOH was used to add the remaining starting material, and the flask was purged with N2 for 15 minutes. H2 gas was then bubbled through the slurry for 5 minutes, and the reaction was allowed to stir for 2 hours under H2 atmosphere at room temperature, after which it was filtered with celite and chromatographed (3×25 cm silica gel, 10% MeOH in CHCl3) to yield s-12 as a white solid (580 mg, 45%). IR (thin film) 3312 (br), 2935 (m), 2861 (w), 1705 (s), 1647 (s), 1546 (s), 1450 (w), 1255 (m) cm-1. 1HNMR (400 MHz, MeOD), 7.97 (s, 2H), 7.83 (d, J=8 Hz, 2H), 7.67 (d, J=8 Hz, 2H), 7.62 (t, J=8 Hz, 2H), 7.35-7.32 (t, J=8 Hz, 2H), 7.13 (s, 1H), 4.37 (d, J=6.4 Hz, 2H), 4.22 (t, J=7.2 Hz, 1H), 3.20-3.12 (m, 6H), 2.31 (t, J=7.2 Hz, 2H), 2.22-2.16 (m, 4H), 1.66-1.59 (m, 6H), 1.56-1.49 (m, 6H), 1.42-1.33 (m, 6H). 13CNMR (100 MHz, MeOD) δ 177.6, 176.1, 158.9, 145.4, 142.6, 128.8, 128.2, 126.2, 121.0, 67.6, 41.6, 40.2, 37.0, 37.0, 30.6, 30.1, 27.6, 27.5, 27.4, 26.8, 26.7, 25.8. HRMS (ES+) calc'd for $C_{33}H_{45}N_3O_6$ (M+H) m/z 580.3381 Found 580.3377.

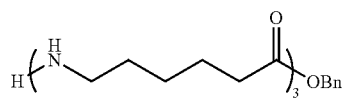

benzyl 6-(6-(6-aminohexanamido)hexanamido)hexanoate (s-13)

s-12 (1.17 g) was dissolved in a mixture of 1:1 $Et_2NH$/$CH_2Cl_2$ (37 mL), and the reaction was stirred at room temperature for 8 hours, after which it was concentrated under reduced pressure and chromatographed (3×25 cm silica gel, 20% MeOH in $CHCl_3$, then 20% MeOH in $CHCl_3$+2.5% $Et_3N$) to yield s-13 as a white solid (630 mg, 81%). IR (thin film) 3221 (w), 3277 (w), 2941 (m), 2862 (w), 1727 (m), 1633 (s), 1542 (m), 1477 (w), 1262 (w), 1184 (w) cm-1. 1HNMR (400 MHz, CDCl3) δ 7.38-7.30 (m, 5H), 5.89 (s, 1H), 5.67 (s, 1H), 5.11 (s, 2H), 3.26-3.20 (m, 6H), 2.27 (t, J=7.2, 2H), 2.19-2.14 (m, 4H), 1.69-1.62 (m, 6H), 1.55-1.48 (m, 6H), 1.40-1.32 (m, 6H). 13CNMR (100 MHz, CDCl3) δ 173.5, 173.0, 172.9, 136.0, 128.4, 128.3, 128.2, 66.2, 41.7, 39.2, 39.1, 36.6, 36.5, 34.1, 32.5, 29.3, 29.2, 26.4, 25.4, 25.1, 24.5. HRMS (ES+) calc'd for $C_{25}H_{41}N_3O_4$(M+H) m/z 448.3170 Found 448.3150.

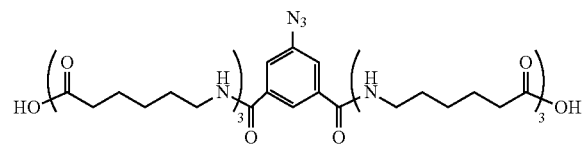

6,6'-((6,6'-((6,6'-((5-azidoisophthaloyl)bis (azanediyl))bis(hexanoyl))bis(azanediyl))bis (hexanoyl))bis(azanediyl) dihexanoic acid (s-14)

A mixture of azidoisophthalic acid (100 mg, 0.483 mmol, 1 equiv.) in 5 mL of dry $CH_2Cl_2$ was prepared in a flame dried flask. To this mixture was sequentially added EDC·HCl (233 mg, 1.21 mmol, 2.5 equiv.), HOBt·H2O (183 mg, 1.21 mmol, 2.5 equiv.), s-13 (476 mg, 1.06 mmol, 2.2 equiv.), and pyridine (0.117 mL, 1.45 mmol, 3 equiv.). The reaction was allowed to stir at room temperature for 18 hours, after which it was directly loaded onto a silica gel column and partially purified to remove the coupling agents (silica gel, 2×15 cm, 10% MeOH in $CHCl_3$). The crude material was dissolved in 5 mL of MeOH and 5 mL of THF. A 1 M solution of LiOH in $H_2O$ was added (1.9 mL, 4 equiv.), and the reaction was allowed to stir at room temperature for 24 hours. A solution of 1 M HCl was added (0.95 mL, 2 equiv.), and the reaction was concentrated under reduced pressure. The crude mixture was then chromatographed (silica gel, 2×15 cm, 20% MeOH in $CHCl_3$, then 20% MeOH in $CHCl_3$+1% TFA) and fractions containing the product were collected and concentrated under reduced pressure to obtain an light brown oil. 50 mL of 95% diethyl ether/5% MeOH was then added to the oil. The ether/MeOH mixture was then decanted, and the oil dried under reduced pressure to obtain s-14 as a white solid (383 mg, 89%, 2 steps). IR (thin film) 3310 (br), 2937 (m), 2865 (w), 2112 (m), 1650 (s), 1553 (m), 1439 (w), 1202 (m), 1139 (m) cm-1. 1HNMR (400 MHz, MeOD) δ 8.05 (s, 1H), 7.65 (s, 2H), 3.39 (t, J=5.6 Hz, 4H), 3.15 (dd, J=3.2, 6.6 Hz, 8H), 2.29 (t, 7.2 Hz, 4H), 2.22-2.15 (m, 8H), 1.68-1.58 (m, 16H), 1.51-1.47 (m, 8H), 1.42-1.32 (m, 12H). 13CNMR (100 MHz, MeOD) δ 177.4, 176.0, 168.3, 138.1, 123.6, 121.5, 41.0, 40.2, 37.0, 34.8, 30.1, 30.1, 27.6, 27.5, 26.7, 25.7. HRMS (ES+) calc'd for $C_{44}H_{71}N_9O_{10}$ (M+H) m/z 886.5397 Found 886.5408.

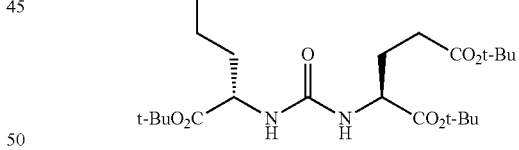

(S)-di-tert-butyl 2-(3-((S)-6-(4-(aminomethyl)-1H-1, 2,3-triazol-1-yl)-1-(tert-butoxy)-1-oxohexan-2-yl) ureido)pentanedioate (s-15)

A mixture of s-1 (180 mg, 0.35 mmol, 1 equiv.) and propargylamine (117 uL, 1.75 mmol, 5 equiv.) was dissolved in a mixture of $H_2O$ (1.25 mL) and t-butanol (1.25 mL) in a 5 mL microwave reaction tube. To the mixture was added 0.1 M sodium ascorbate (0.7 mL, 0.2 equiv.) and 0.1 M copper(II) sulfate (0.14 mL, 0.04 equiv.). The tube was capped, and subject to microwave irradiation for 2.5 minutes at 110° C. The reaction was then concentrated under reduced pressure at 60° C., and chromatographed (silica gel, 1×15 cm, 10% MeOH in CHCl₃, then 10% MeOH in CHCl₃+ 2.5% Et₃N) to obtain s-15 as a pale, green oil (152 mg, 77%). IR (thin film) 2978 (m), 2933 (w), 1730 (s), 1647 (m), 1559 (m), 1456 (w), 1368 (m), 1255 (w), 1154 (s) cm-1. 1HNMR (400 MHz, MeOD) δ 7.90 (s, 1H), 4.90 (t, J=7.2 Hz, 2H), 4.20-4.16 (m, 1H), 4.14-4.12 (m, 1H), 3.96 (s, 2H), 2.36-2.26 (m, 2H), 2.08-2.00 (m, 1H), 1.95-1.89 (m, 2H), 1.84-1.73 (m, 2H), 1.69-1.59 (m, 1H), 1.46 (s, 9H), 1.44 (s, 18H), 1.39-1.31 (m, 2H). 13CNMR (100 MHz, MeOD) δ 173.7, 173.7, 173.5, 159.9, 147.7, 123.8, 82.8, 82.7, 81.8, 54.2, 51.1, 37.1, 32.9, 32.5, 30.8, 29.0, 28.4, 28.3, 23.5. HRMS (ES+) calc'd for $C_{27}H_{48}N_6O_7$ (M+H) m/z 568.3657 Found 568.3637.

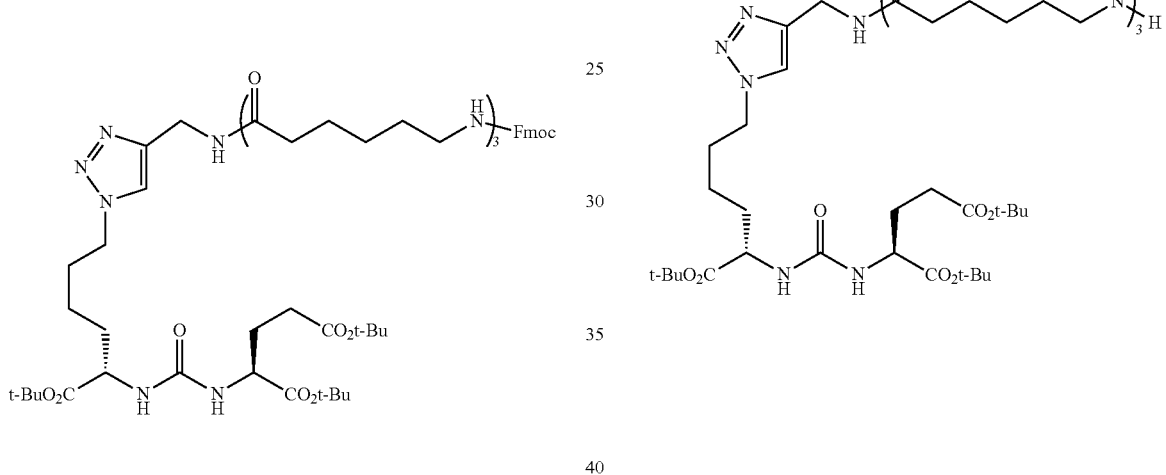

(S)-di-tert-butyl 2-(3-((S)-6-(4-(1-(9H-fluoren-9-yl)-3,10,17,24-tetraoxo-2-oxa-4,11,18,25-tetraazahexacosan-26-yl)-1H-1,2,3-triazol-1-yl)-1-(tert-butoxy)-1-oxohexan-2-yl)ureido)pentanedioate (s-16)

A mixture of 6-((((9H-fluoren-9-yl)methoxy)carbonyl)amino)hexanoic acid (156 mg, 0.267 mml, 1 equiv.) was prepared in 1.5 mL of dry CH₂Cl₂. To this slurry was added EDC·HCl (56 mg, 0.294 mmol, 1.1 equiv.) and HOBt·H₂O (45 mg, 0.294 mmol, 1.1 equiv.). A solution of s-16 (152 mg, 0.267 mmol, 1 equiv.) in 3 mL of dry CH₂Cl₂, followed by DIPEA (32 uL, 0.294 mmol, 1.1 equiv.), was added to this slurry. The reaction was allowed to stir at room temperature for 2 hours, after which EDC·HCl (28 mg, 0.247 mmol, 0.5 equiv.), HOBt·H₂O (23 mg, 0.247 mmol, 0.5 equiv.), and DIPEA (32 uL, 0.294 mmol, 1.1 equiv.) were added. The reaction was allowed to stir at room temperature for an additional 2 hours, after which the reaction was concentrated down under reduced pressure and chromatographed (silica gel, 2×15 cm, 10% MeOH in CHCl₃) to give s-16 as a viscous, pale green oil (235 mg, 78%). IR (thin film) 2933 (m), 2862 (w), 2413 (br), 1729 (s), 1630 (s), 1453 (s), 1367 (m), 1251 (w), 1153 (s), 742 (w) cm-1. 1HNMR (400 MHz, MeOD) δ 7.84 (s, 1H), 7.80 (d, J=7.2 Hz, 2H), 7.64 (d, J=7.2 Hz, 2H), 7.39 (t, J=8 Hz, 2H), 4.40 (d, J=2 Hz, 2H), 4.37 (t, J=6.8 Hz, 2H), 4.33 (d, J=6.8 Hz, 2H), 4.21-4.17 (m, 2H), 4.13 (dd, J=5.2, 8 Hz, 1H), 3.17-3.08 (m, 6H), 2.34-2.29 (m, 2H), 2.23-2.13 (m, 6H), 2.08-2.00 (m, 1H), 1.94-1.86 (m, 2H), 1.84-1.73 (m, 2H), 1.64-1.57 (m, 7H), 1.52-1.43 (m, 5H), 1.46 (s, 9H), 1.43 (s, 18H), 1.39-1.29 (m, 9H). 13CNMR (100 MHz, MeOD) δ 176.0, 175.9, 173.7, 173.6, 173.4, 159.9, 158.8, 146.2, 145.3, 142.6, 128.8, 128.1, 126.2, 124.1, 120.9, 82.8, 82.6, 81.7, 67.6, 54.6, 54.1, 51.3, 41.6, 40.2, 37.0, 37.0, 36.7, 35.6, 32.9, 30.8, 30.6, 30.1, 29.0, 28.4, 28.3, 27.5, 27.4, 26.7, 26.7, 26.5, 23.4. HRMS (ES+) calc'd for $C_{60}H_{91}N_9O_{12}$ (M+H) m/z 1130.6860 Found 1130.6848.

(S)-di-tert-butyl 2-(3-((S-6-(4-((6-(6-(6-aminohexanamido)hexanamido)hexanamido)methyl)-1H-1,2,3-triazol-1-yl)-1-(tert-butoxy)-1-oxohexan-2-yl)ureido)pentanedioate (s-17)

s-16 (195 mg) was dissolved in 2.5 mL of Et₂NH and 2.5 mL of CH₂CO₂. The reaction was allowed to stir at room temperature for 26 hours, after which it was concentrated under reduced pressure and chromatographed (silica gel, 2×15 cm, 20% MeOH in CHCl₃, then 20% MeOH in CHCl₃+2.5% Et₃N) to obtain s-17 as a sticky, pale yellow solid (137 mg, 90%). IR (thin film) 3271 (br), 2934 (m), 2864 (w), 1731 (s), 1643 (s), 1556 (s), 1457 (w), 1367 (m), 1256 (w), 1154 (s) cm-1. 1HNMR (400 MHz, MeOD) δ 7.99 (s, 1H), 7.88 (s, 1H), 6.40 (dd, J=12, 14 Hz, 1H), 4.42 (s, 2H), 4.41 (t, J=9 Hz, 2H), 4.21-4.11 (m, 2H), 3.22-3.14 (m, 4H), 2.93 (t, J=8 Hz, 2H), 2.35-2.30 (m, 2H), 2.25-2.16 (m, 6H), 2.08-2.01 (m, 1H), 1.95-1.90 (m, 1H), 1.83-1.74 (m, 2H), 1.71-1.58 (m, 9H), 1.55-148 (m, 4H), 1.48 (s, 9H), 1.45 (s, 18H), 1.42-1.29 (m, 10H). 13CNMR (100 MHz, MeOD) δ 176.0, 175.7, 173.8, 173.7, 173.5, 159.9, 146.3, 124.2, 82.8, 82.7, 81.8, 81.7, 40.6, 40.2, 40.2, 37.0, 36.8, 36.6, 35.6, 32.9, 32.5, 30.8, 30.6, 30.2, 29.0, 28.4, 28.3, 27.6, 27.0, 26.8, 26.5, 26.4, 23.5. HRMS (ES+) calc'd for $C_{34}H_{81}N_9O_{10}$ (M+H) m/z 908.6179 Found 908.6165.

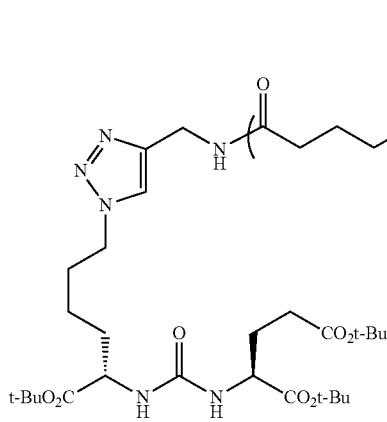

s-18

To a solution of s-14 (150 mg, 0.169 mmol, 1.0 equiv.) in CH₂Cl₂ (1.5 mL) was added EDC HCl (81 mg, 0.423 mmol, 2.5 equiv.), HOBt·H₂O (65 mg, 0.423 mmol, 2.5 equiv.), followed by a solution of s-15 (212 mg, 0.373 mmol, 2.2 equiv.) in CH₂Cl₂ (3.5 mL). Pyridine (82 □L, 0.507 mmol, 3 equiv.) was added to the resulting solution, and the reaction was allowed to stir at room temperature for 20 hours, after which it was concentrated under reduced pressure and partially purified by silica gel chromatography (1×15 cm, silica gel, 5% MeOH in CHCl₃, then 10% MeOH in CHCl₃) to yield a dark red oil (190 mg, 57% crude) that was carried onto the next step.

over 66 min at 5 mL/min). The product was isolated and lyophilized to yield a white powder (11 mg, 11%). IR (thin film) 2938 (w), 1634 (s), 1553 (m), 1461 (m), 1369 (w), 1141 (s), 975 (w), 841 (w), 800 (w), 722 (w) cm-1. 1HNMR (400 MHz, MeOD) δ 8.78 (t, J=5.4 Hz, 1H), 8.48 (s, 1H), 8.45 (d, J=1.6 Hz, 2H), 8.36 (s, 1H), 7.88 (s, 2H), 4.41-4.37 (m, 8H), 4.18 (dd, J=5, 8.8 Hz, 2H), 4.12 (dd, J=5.2, 8 Hz, 2H), 3.67-3.64 (m, 1H), 3.43 (t, J=6.8 Hz, 4H), 3.14 (t, J=6.4 Hz, 8H), 2.84 (t, J=7 Hz, 2H), 2.37 (t, J=7.2 Hz, 2H), 2.34-2.29 (m, 4H), 2.26-2.13 (m, 12H), 2.08-1.99 (m, 2H), 1.95-1.87 (m, 4H), 1.84-1.71 (m, 6H), 1.69-1.54 (m, 20H), 1.50-1.42 (m, 10H), 1.46 (s, 18H), 1.44 (s, 18H), 1.43 (s, 18H), 1.38-1.26 (m, 12H). 13CNMR (100 MHz, MeOD) δ

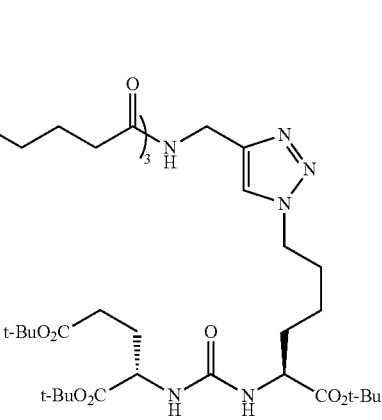

s-19

Partially pure s-18 (100 mg, 0.05 mmol, 1.0 equiv.) was dissolved in H₂O (1.25 mL) and t-BuOH (1.25 mL) in a 5 mL microwave vial. To this solution was added 6-heptynoic acid (6.4 µL, 0.05 mmol, 1.0 equiv.), 0.1 M Sodium Ascorbate (0.5 mL, 0.05 mmol, 1.0 equiv.), and 0.1 M copper(II) sulfate (0.25 mL, 0.025 mmol, 0.5 equiv.). The vial was sealed and subjected to microwave irradiation for 1 hour at 110° C., after which the reaction was concentrated and purified by HPLC (Sunfire™ Prep C18 column (10×150 mm) using a 50% MeCN to 80% MeCN in H2O gradient 176.0, 173.7, 173.7, 173.5, 167.9, 159.9, 138.2, 122.6, 82.8, 82.7, 81.7, 54.6, 54.2, 40.2, 37.0, 32.9, 32.5, 30.1, 29.0, 28.4, 28.3, 27.6, 26.7, 23.4. HRMS (ES+) calc'd for $C_{105}H_{173}N_{21}O_{24}$ (M+H) m/z 2113.3062 Found (M+2H) 1057.1462.

s-20

Partially pure s-19 (35 mg, 0.018 mmol, 1.0 equiv.) was dissolved in THF. To this solution was added the N-hydroxysuccinimidyl ester of trifluoroacetic acid (19 mg, 0.09 mmol, 5.0 equiv.) and pyridine (10 mg, 0.125 mmol, 7.0 equiv.). The reaction was allowed to stir at room temperature for 1.5 hours, after which it was quenched with 0.5 mL of PBS and concentrated under reduced pressure. To the resulting mixture was added 2 mL of 95% TFA/5% TIPS, and the reaction was allowed to stir at room temperature for 1 hour, after which the TFA was removed under reduced pressure. The reaction mixture was purified by HPLC (Sunfire™ Prep C18 column (10×150 mm) using a 0% MeCN to 80% MeCN in H2O gradient over 51 min at 5 mL/min) and fractions containing the product was isolated and lyophilized to give s-20 (1.9 mg), which was used immediately in the next reaction.

cp33-Bis(Ac3-Urea)

s-20 was dissolved in 975 μL of PBS and 325 μL of saturated sodium bicarbonate in water. cp33 peptide (2.4 mg, 0.0011 mmol, 1.1 equiv.) was added, and the reaction was allowed to stir at room temperature for 7 hours, after which the reaction mixture was loaded directly onto the HPLC and purified (Sunfire™ Prep C18 column (10×150 mm) using a 0% MeCN to 80% MeCN in H2O gradient over 51 min at 5 mL/min). The fractions containing the product was collected and lyophilized to give a white powder (1.1 mg, 25.6%).

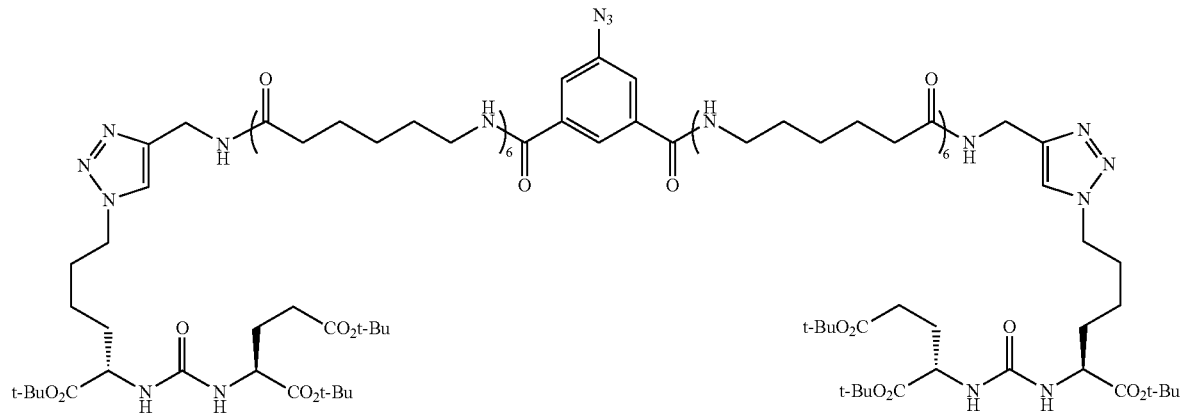

s-21

A solution of s-14 (190 mg, 0.214 mmol, 1.0 equiv.) was prepared in CH$_2$Cl$_2$ (5 mL). EDC·HCl (103 mg, 0.535 mmol, 2.5 equiv.) and HOBt·H$_2$O (82 mg, 0.535 mmol, 2.5 equiv.) were added, followed by a solution of s-17 (428 mg, 0.472 mmol, 2.2 equiv.) in CH$_2$Cl$_2$ (5 mL). Pyridine (52 μL, 0.642 mmol, 3.0 equiv.) was added, and the reaction was allowed to stir at room temperature for 24 hr, after which it was concentrated under reduced pressure and chromatographed (Silica gel, 1×15 cm, 10% MeOH in CHCl$_3$, then 15% MeOH in CHCl$_3$, then 20% MeOH in CHCl$_3$) to give a partially pure, pale yellow solid (250 mg, 44% crude).

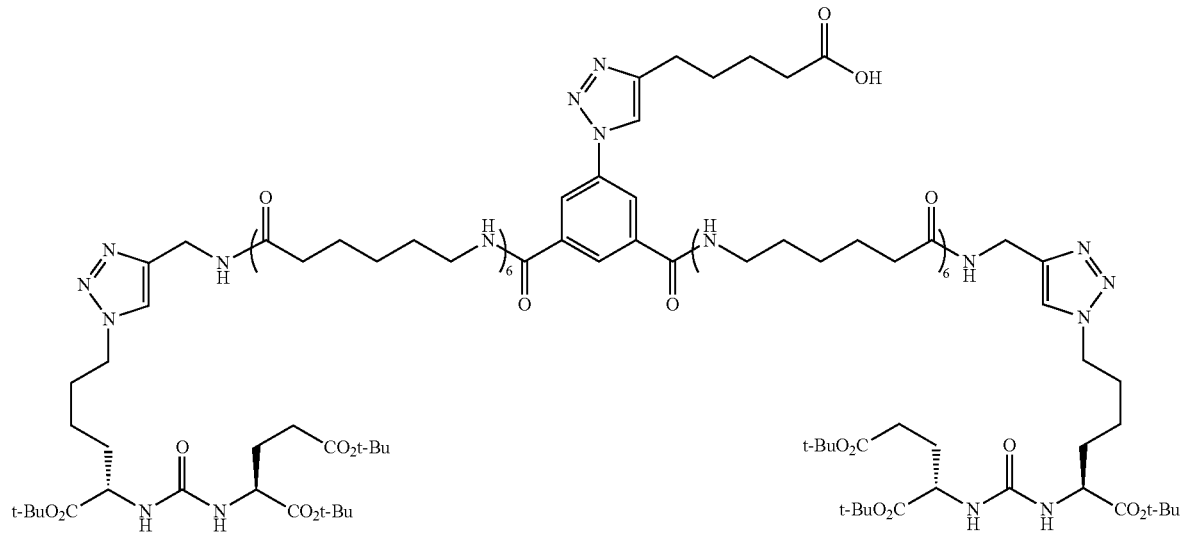

s-22 s-21 (50 mg, 0.019 mmol, 1.0 equiv.) was dissolved in H₂O (0.5 mL) and 1-BuOH (0.5 mL) in a 2 mL microwave vial. To this solution was added 6-heptynoic acid (2.5 □L, 0.019 mmol, 1.0 equiv.), 0.1 M Sodium Ascorbate (0.2 mL, 1.0 equiv.), and 0.1 M copper(II) sulfate (0.1 mL, 0.5 equiv.). The vial was sealed and subjected to microwave irradiation for 1 hour at 110° C., after which the reaction was concentrated and chromatographed (1×15 cm, silica gel, 20% MeOH in CHCl₃, then 20% MeOH in CHCl₃+1% TFA). The fractions containing the product were concentrated, washed with diethyl ether (50 mL), and azeotroped with CDCl₃ to give a partially pure green solid (27 mg) that was carried forward to the next step.

s-23

Partially pure s-22 (37 mg, 0.013 mmol, 1.0 equiv.) was dissolved in DMF (0.5 mL). EDC (7.7 mg, 0.04 mmol, 3.0 equiv.), HOBt (6.2 mg, 0.04 mmol, 3.0 equiv.), and N-hydroxysuccinimide (4.6 mg, 0.04 mmol, 3.0 equiv.) were added sequentially, followed by DIPEA (7.1 μL, 0.04 mmol, 3.0 equiv.). The reaction was allowed to stir for 1 hour, after which EDC (7.7 mg, 0.04 mmol, 3.0 equiv.) and DIPEA (7.1 uL, 0.04 mmol. 3.0 equiv.) were added. The reaction was allowed to stir for another 2 hours, after which the DMF was removed by passing a steady stream of N2 over the reaction. 1 mL of a mixture of 98% TFA/2% TIPS was added to the flask, and the reaction was allowed to stir at room temperature for 30 minutes, after which the TFA was removed under reduced pressure. The reaction was purified by HPLC (Sunfire™ Prep C18 column (10×150 mm) using a 0% MeCN to 80% MeCN in H2O gradient over 51 min at 5 mL/min). Fractions containing the product were collected and lyophilized to give s-23 as a white powder (2.5 mg), which was used immediately in the next step.

cp33-Bis(Ac6-Urea)

s-23 (2.5 mg, 0.86 μmol, 1.0 equiv.) was dissolved in 0.9 mL of PBS and 0.4 mL of a 7.5% solution of sodium bicarbonate in water. cp33 (2 mg, 0.65 μmol, 0.75 equiv.) was added, and the reaction was allowed to stir at room temperature for 1 hour, after which 1 mL of DMF was added. The reaction was allowed to stir for an additional 6 hours at room temperature, after which the reaction mixture was injected directly onto the HPLC and purified (Sunfire™ Prep C18 column (10×150 mm) using a 10% MeCN to 65% MeCN in H2O gradient over 66 min at 5 mL/min). Fractions containing the product were collected and lyophilized to give cp33-Bis(Ac6-Urea) as a white powder (0.2 mg, 4.5%).

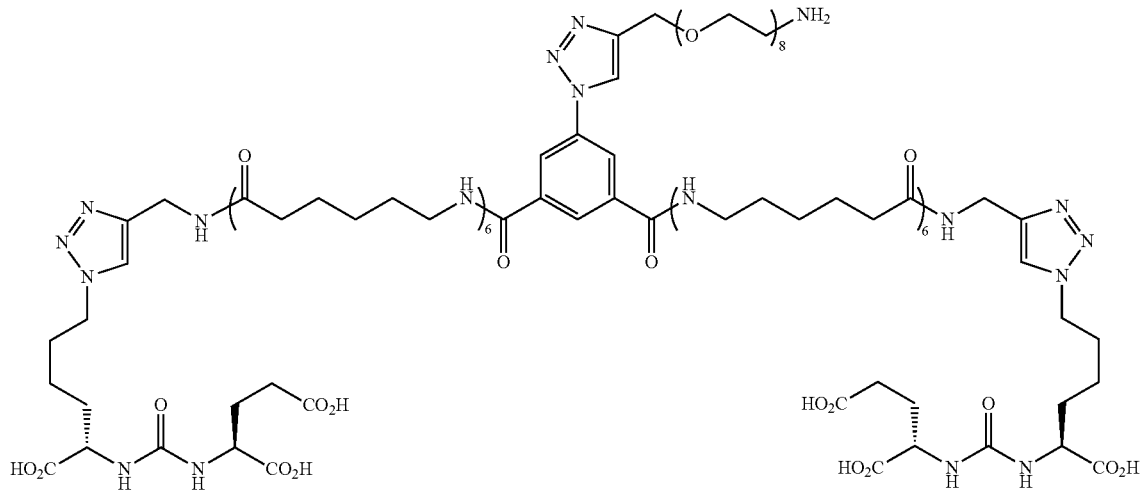

s-22

3,6,9,12,15,18,21,24-octaoxaheptacos-26-yn-1-amine (3 mg, 0.007 mmol, 1.0 equiv.) was added to a 2 mL microwave vial, followed by a solution of s-20 (20 mg, 0.007 mmol, 1.0 equiv.) in H₂O (0.25 mL) and 1-BuOH (0.25 mL). To this solution was added 0.1 M Sodium Ascorbate (70 μL, 0.007 mmol, 1.0 equiv.), and 0.1 M copper(II) sulfate (35 μL, 0.0035 mmol, 0.5 equiv.). The vial was sealed and subjected to microwave irradiation for 1 hour at 110° C., after which the reaction was concentrated to yield a crude, dark red oil. The oil was taken up with 67% TFA in CH₂Cl₂ (3 mL) into a 5 mL vial, and the vial was subjected to microwave irradiation for 2 minutes at 70° C. The reaction was concentrated down, taken up with 50% MeCN in H₂O, and purified by HPLC (Sunfire™ Prep C18 column (10×150 mm) using a 50% MeCN to 80% MeCN in H2O gradient over 66 min at 5 mL/min). The product was isolated and lyophilized to yield s-22 as a white powder (3 mg, 15%). IR (thin film) 3296 (br), 2934 (m), 2864 (w), 1643 (s), 1556 (m), 1463 (w), 1202 (m), 1134 (m) cm-1. 1HNMR (500 MHz, MeOD) δ 8.70 (s, 1H), 8.48 (d, J=1.5 Hz, 2H), 8.38 (t, J=1.5 Hz, 1H), 7.86 (s, 2H), 4.78 (s, 2H), 4.42 (d, J=3.2 Hz, 4H), 4.39 (t, J=7.2 Hz, 4H), 4.30 (dd, J=5, 9 Hz, 2H), 4.27 (dd, J=5, 8.5 Hz, 2H), 3.77-3.75 (m, 4H), 3.72-3.60 (m, 32H), 3.47 (t, J=7.2 Hz, 4H), 3.15 (t, J=7.2 Hz, 22H), 2.43-2.39 (m, 4H), 2.24-2.14 (m, 26H), 1.94-1.84 (m, 10H), 1.70-1.64 (m, 12H), 1.63-1.55 (m, 20H), 1.53-1.37 (m, 30H), 1.35-1.29, (m, 20H). HRMS (ES+) calc'd for $C_{129}H_{218}N_{28}O_{36}$ (M+H) m/z 2737.6191 Found 2737.6153.

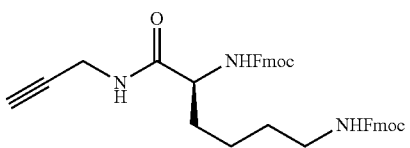

(S)-bis((9H-fluoren-9-yl)methyl) (6-oxo-6-(prop-2-yn-1-ylamino)hexane-1,5-diyl)dicarbamate (s-23)

To a solution of Fmoc-Lys(Fmoc)-OH (1 g, 1.69 mmol, 1.0 equiv.) in CH$_2$Cl$_2$ (30 mL) was added EDC·HCl (391 mg, 2.03 mmol, 1.2 equiv.), HOBt·H$_2$O (311 mg, 2.03 mmol, 1.2 equiv.), followed by propargylamine (93 mg, 0.11 mL, 1.69 mmol, 1.0 equiv.) and DIPEA (264 mg, 0.36 mL, 2.03 mmol, 1.2 equiv.). The reaction was allowed to stir at room temperature for 90 minutes, upon which the reaction turned into a gel. The gel was broken up with a spatula and taken up with CH$_2$Cl$_2$ (50 mL). The mixture was sonicated and filtered. The filtrate was collected, washed with 10% citric acid (50 mL), saturated sodium bicarbonate (50 mL), and brine (50 mL). The organic layer was collected, dried with MgSO$_4$, and concentrated under reduced pressure to give s-23 as a white powder (330 mg, 31% yield). IR (thin film) 3297 (s), 3068 (br), 2937 (br), 1687 (s), 1650 (s), 1539 (m), 1450 (w), 1264 (w) cm-1. 1HNMR (500 MHz, CDCl3) δ 7.75 (t, J=7.8 Hz, 4H), 7.56 (d, J=7.4 Hz, 4H), 7.39 (q, J=7.5 Hz, 4H), 7.30 (q, J=7.5 Hz, 4H), 6.28 (bs, 1H), 5.44 (bs, 1H), 4.85 (bs, 1H), 4.43-4.35 (m, 4H), 4.21-4.30 (m, 3H), 4.02 (s, 2H), 3.25-3.15 (m, 2H), 2.18 (t, J=2.4 Hz, 1H), 1.95-1.85 (m, 1H), 1.75-1.65 (m, 1H), 1.60-1.50 (m, 2H), 1.42-1.32 (m, 2H). 13CNMR (125 MHz, CDCl3) δ 171.4, 156.9, 144.1, 144.0, 143.9, 143.8, 141.5, 141.4, 127.9, 127.8, 127.2, 127.2, 125.1, 125.1, 120.2, 120.1, 79.3, 72.0, 67.2, 66.8, 47.4, 40.3, 31.7, 29.6, 29.4, 22.3. HRMS (ES+) calc'd for C$_{39}$H$_{37}$N$_3$O$_5$ (M+H) m/z 628.2806 Found 628.2802.

(S)-bis((9H-fluoren-9-yl)methyl) (11,19-dioxo-13-(prop-2-yn-1-ylcarbamoyl)-3,6,9,21,24,27-hexaoxa-12,18-diazanonacosane-1,29-diyl)dicarbamate (s-25)

Fmoc-miniPEG3-COOH (164 mg, 0.38 mmol, 2.2 equiv.) was dissolved in CH$_2$Cl2 (5 mL). To this solution was added EDC·HCl (84 mg, 0.44 mmol, 2.5 equiv.) and HOBt·H2O (67 mg, 0.44 mmol, 2.5 equiv.). The resulting solution was transferred to a flask containing s-24 (32 mg, 0.174 mmol, 1.0 equiv.). DIPEA (68 mg, 92 μL, 0.52 mmol, 3.0 equiv.) was added, followed by 1 mL of DMF. The reaction was allowed to stir at room temperature for 6 hours, after which it was concentrated and chromatographed (5% MeOH in CHCl$_3$) to yield a clear oil (122 mg, 70%). IR (thin film) 3307 (br), 3063 (w), 2918 (s), 1712 (m), 1659 (m), 1535 (s), 1450 (w), 1253 (m), 1105 (m) cm-1. 1HNMR (500 MHz, CDCl3) δ 7.76 (d, J=7.5 Hz, 4H), 7.60 (d, J=7.5 Hz, 4H), 7.39 (t, J=7.5 Hz, 4H), 7.30 (t, J=7.5 Hz, 4H), 6.97 (bs, 1H), 6.84 (bs, 1H), 5.74 (bs, 1H), 5.63 (bs, 1H), 4.44-4.38 (m, 5H), 4.21 (t, J=7 Hz, 2H), 4.05-3.96 (m, 6H), 3.65-3.61 (m, 16H), 3.57-3.55 (m, 4H), 3.42-3.35 (m, 4H), 3.28-3.21 (m, 3H), 2.15 (t, J=2 Hz, 1H), 1.93-1.87 (m, 1H), 1.72-1.66 (m, 1H), 1.56-1.50 (m, 2H), 1.39-1.34 (m, 2H). 13CNMR (125 MHz, CDCl3) δ 171.2, 170.6, 170.1, 156.8, 144.2, 144.1, 141.5, 127.8, 127.8, 127.2, 125.3, 125.2, 120.1, 71.7, 71.1, 71.0, 70.6, 70.5, 70.5, 70.4, 70.4, 70.2, 70.2, 66.7, 66.7, 52.5, 47.4, 47.4, 41.1, 38.6, 31.5, 29.2, 23.1. HRMS (ES+) calc'd for C$_{55}$H$_{67}$N$_5$O$_{13}$ (M+H) m/z 1007.4840 Found 1007.4839.

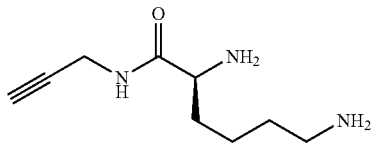

(S)-2,6-diamino-N-(prop-2-yn-1-yl)hexanamide (s-24)

s-23 (300 mg) was dissolved in 10 mL of Et$_2$NH and 10 mL of CH$_2$Cl$_2$. The reaction was allowed to stir for 24 hours, after which it was concentrated and purified with column chromatography (25% MeOH in CH$_2$Cl$_2$, then 25% MeOH in CH$_2$Cl$_2$+2% NH$_4$OH) to yield s-24 as a white solid (48 mg, 55%). IR (thin film) 3278 (br), 2931 (m), 2861 (w), 1649 (s), 1554 (s), 1345 (w), 1262 (w), 920 (w) cm-1. 1HNMR (400 MHz, MeOD) δ 3.96 (dd, J=2.4, 7.2 Hz, 2H), 3.26 (t, J=7 Hz, 1H), 2.71 (t, J=7.6 Hz, 2H), 2.59 (m, 1H), 1.69-1.61 (m, 1H), 1.58-1.47 (m, 3H), 1.46-1.34 (m, 2H). 13CNMR (100 MHz, MeOD) δ 177.3, 80.1, 72.3, 55.9, 41.7, 36.0, 31.8, 29.3, 23.8. HRMS (ES+) calc'd for C$_9$H$_{17}$N$_3$O (M+H) m/z 184.1444 Found 184.1441.

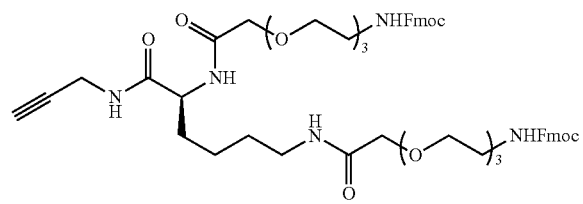

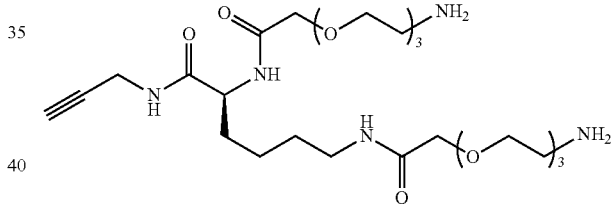

(S)—N,N'-(6-oxo-6-(prop-2-yn-1-ylamino)hexane-1,5-diyl)bis(2-(2-(2-(2-aminoethoxy)ethoxy)ethoxy)acetamide) (s-26)

s-25 (120 mg) was dissolved in 5 mL of CH$_2$Cl$_2$ and 5 mL of Et$_2$NH. The reaction was allowed to stir at room temperature for 24 hours, after which it was concentrated and chromatographed (1×15 cm silica gel, 25% MeOH in CH$_2$Cl$_2$, then 25% MeOH in CH$_2$Cl$_2$+2% NH$_4$OH) to yield a colorless oil (42 mg, 63%). IR (thin film) 3289 (br), 2865 (m), 1655 (s), 1532 (m), 1457 (w), 1103 (m) cm-1. 1HNMR (400 MHz, MeOD) δ 4.40 (dd, J=5.4, 8.8 Hz, 1H), 4.04 (s, 2H), 3.98-3.95 (m, 4H), 3.73-3.61 (m, 16H), 3.53 (dt, J=2, 5.2 Hz, 4H), 3.24 (t, J=7 Hz, 2H), 2.62 (t, J=1.5 Hz, 1H), 1.89-1.80 (m, 1H), 1.76-1.68 (m, 1H), 1.59-1.52 (m, 2H), 1.43-1.33 (m, 2H). 13CNMR (100 MHz, MeOD), d 173.5, 172.6, 172.6, 80.5, 73.3, 73.2, 72.4, 72.0, 71.9, 71.6, 71.5, 71.4, 71.4, 71.2, 71.2, 71.2, 53.9, 42.1, 42.1, 39.7, 33.1, 30.1, 29.5, 24.1. HRMS (ES+) calc'd for C$_{25}$H$_{47}$N$_5$O$_9$ (M+H) m/z 562.3447 Found 562.3448.

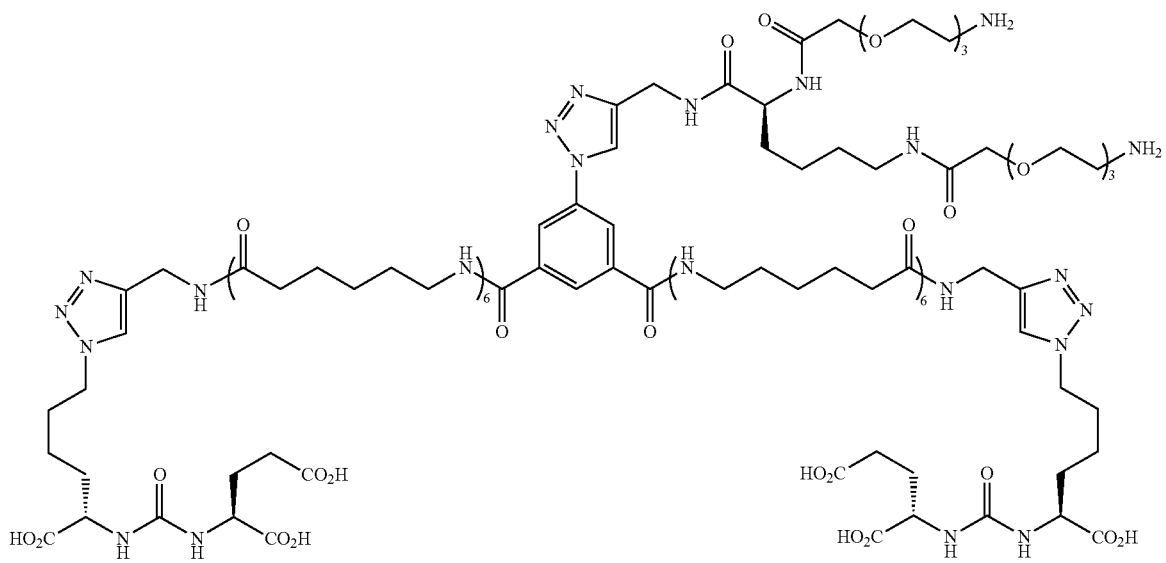

s-27 s-21 (162 mg, 0.091 mmol, 1 equiv.) and s-26 (34 mg, 0.091 mmol, 1 equiv.) was dissolved in $H_2O$ (1.5 mL) and t-BuOH (1.5 mL) in a 5 mL microwave vial. To this solution was added 0.1 M sodium ascorbate (0.6 mL, 1 equiv.) and 0.1 M copper(II) sulfate (0.3 mL, 0.5 equiv.). The vial was sealed and subjected to microwave irradiation for 1 hour at 110° C., after which the reaction was concentrated under reduced pressure to yield a crude, brown oil. The crude oil was taken up with 67% TFA in $CH_2Cl_2$ (3 mL) in a 5 mL microwave vial. The vial was sealed and subjected to microwave irradiation for 2 minutes at 70° C., after which the reaction was concentrated under reduced pressure and purified using HPLC (Sunfire™ Prep C18 column (10×150 mm) using a 50% MeCN to 80% MeCN in H2O gradient over 66 min at 5 mL/min). The product was isolated and lyophilized to yield a white powder (25 mg, 14%, 2 steps). IR (thin film) 3300 (br), 3093 (w), 2935 (m), 2866 (w), 1640 (s), 1552 (m), 1459 (w), 1201 (w), 1135 (w) cm-1. 1HNMR (500 MHz, MeOD) δ 8.56 (s, 1H), 8.45 (d, J=1.6 Hz, 2H), 8.37 (t, J=1.5 Hz, 2H), 7.86 (s, 2H), 5.49 (s, 2H), 4.58 (s, 2H), 4.45-4.40 (m, 6H), 4.39 (t, J=7 Hz, 4H), 4.30 (dd, J=5, 9 Hz, 2H), 4.26 (dd, J=5, 9 Hz, 2H), 4.07 (s, 2H), 4.00 (s, 2H), 3.73-3.66 (m, 24H), 3.43 (t, J=7 Hz, 4H), 3.23 (dt, J=3.1, 7.5 Hz, 2H), 3.17-3.13 (m, 26H), 2.43-2.39 (m, 4H), 2.24-2.13 (m, 28H), 1.96-1.82 (m, 10H), 1.78-1.71 (m, 2H), 1.71-1.63 (m, 12H), 1.63-1.54 (m, 24H), 1.53-1.46 (m, 24H), 1.44-1.37 (m, 12H), 1.35-1.29 (m, 22H), 1.04 (d, J=5.6 Hz, 2H). 13CNMR (125 MHz, MeOD) δ 176.3, 176.1, 175.9, 175.8, 174.1, 172.6, 172.5, 171.1, 167.8, 161.5, 161.2, 160.1, 147.4, 138.6, 138.3, 127.9, 124.3, 122.7, 122.6, 118.4, 116.1, 71.8, 71.7, 71.4, 71.2, 71.2, 71.1, 67.9, 67.9, 54.8, 54.2, 53.7, 53.5, 51.1, 41.1, 40.7, 40.6, 40.2, 39.6, 37.0, 36.8, 35.6, 32.9, 32.8, 31.1, 30.7, 30.1, 30.1, 28.8, 27.6, 27.5, 26.7, 26.5, 25.7, 24.1, 23.4, 17.6, 12.9. HRMS (ES+) calc'd for $C_{135}H_{228}N_{32}O_{37}$ (M+3H) m/z 964.2387 Found (M+3H) m/z 964.2380.

Bis(cp33)-Bis(Ac6-Urea)

s-27 (1.0 mg, 0.31 μmol, 1.0 equiv.) was dissolved in 0.15 mL of DMF. To this solution was added a solution of cp33-Ac-NHS (1.48 mg, 0.62 □mol, 2.0 equiv.) in 0.15 mL of DMF. DIPEA was subsequently added, and the reaction was allowed to stir at room temperature for 12 hours. The reaction was quenched with 1 mL of water and injected directly onto the HPLC and purified (Sunfire™ Prep C18 column (10×150 mm) using a 20% MeCN to 60% MeCN in H2O gradient over 30 min at 5 mL/min) to give a white powder (0.4 mg, 19%).

Biological Evaluation

The following buffers, solutions, proteins, antibodies, reagents, equipment, materials, software, etc. as indicated, were used in carrying out the biological evaluation.

| Buffers and Solutions: |
| --- |
| Ultra-low IgG FBS |
| Invitrogen #16250-086 |
| RPMI-1640 medium |
| Invitrogen #11875-093 |
| stored at 4° C. |
| RPMI-1640 phenol free media |
| Invitrogen #11835-030 |
| RPMI Growth media |
| RPMI Medium 1640 |
| FROM xxx |
| DMEM- hi glucose |
| XXXX |
| Color-Free ADCP Media |
| RPMI Medium 1640, liquid |
| ATCC #11835-030 without phenol red |
| supplemented with 10% HI-FBS ultra-low |
| IgG |
| and 1% penicillin-streptomycin |
| DPBS Solution |
| Invitrogen #14190-144 |
| EDTA Detachment Solution |
| 210 mL DPBS |
| 392 mg EDTA disodium salt (5.0 mM) |
| 84 mg EGTA (1.0 mM) |
| to pH 7.4 |
| 0.22 μM sterile filter |
| TBS-A Tris-buffered saline with 1.5% BSA |
| Anti-PSMA antibody phycoerthryin |
| conjugated |
| From Abcam #AB-77228 |
| Phycoerythrin calibration beads |
| Bangs Laboratories Quantum ™ R-PE |
| MESF (#827) |

| Proteins, Antibodies and Reagents |
|---|
| Avi-tagged recombinant human PSMA protein kindly provided by Dr. Jan Konvalinka and Dr. Ceril Barinka with reference |
| Anti-Dinitrophenyl-KLH Rabbit IgG Fraction Invitrogen #A6430 The purchased solution was stored at 4° C. |
| Streptavidin-Alexa467 (Invitrogen) |
| Penicillin-Streptomycin, Liquid (10,000 units penicillin, 10,000 μg Streptomycin/mL) Invitrogen #15140-163 |
| Recombinant Human IFN-γ Cell signaling technologies #8901SC |
| Vybrant DiD Cell Labeling Solution Invitrogen #V-22887 1 mM in ethanol FL-4 fluorophore |
| Vybrant DiO Cell Labeling Solution Invitrogen #V-22886 1 mM in DMF FL-1 fluorophore |
| Trypan Blue Stain 0.4% Invitrogen #15250 |
| AT10 antibody ab23336 lot #902047 |
| Lucigenin Tokyo Chemicals |
| Prism graphpad software |

Equipment, Materials and Software
96 Well Flat Bottom Immuno Plate
MaxiSorp, Non Sterile, PS
Nunc #442404
C6 Flow Cytometer Accuri
with CFlow Plus software
Amnis Imagestream X flow cytometer with
IDEAS analysis software
FlowJo software
Petri Dishes
BD Falcon #351029
100×15 mm
Tissue culture dish
BD Falcon #353003
100×20 mm
Synergy 2 Multimode Microplate Reader
BioTek with Gen 5 software
T-Flasks
BD Falcon #353136
75 cm² tissue culture treated
Streptavidin labeled 6 uM beads
Polysciences 6 uM YG fluoresebrite beads
0.7 ug/mL biotin loading lot #601514
1.4 ug/mL biotin loading lot #573565
6 uM non-fluorescent beads
2.0 ug/mL biotin loading lot #621277
Cell Culture
General Procedures
 Cell Counting: A cell suspension (10 μL) was diluted in Trypan blue (0.4%, 90 μL). 10 μL of this mixture was loaded onto a hemocytometer. Live cells were counted visually under 10× magnification.
 EDTA Detachment: Adherent cells were aspirated and washed with DPBS (5 mL). To the flask was added the EDTA detachment solution (5 mL). The flask was incubated (15 min). Cells were fully detached by gently rinsing the solution over the bottom of the flask. The cell suspension was pelleted, aspirated, suspended in media, and split as desired into new flasks.
 Incubations were done at 37° C. in a humidified atmosphere supplemented with 5% CO2.
 Pelleting was done by centrifuge for 5 minutes at 1100 rpm.
Cell Lines:
 All cell lines were grown in an incubator (37° C.) supplemented with 5% CO2. Media was changed approximately every 4 days. Cells were split approximately 4:1. Cells were not grown beyond approximately 30 passages.
 U937 Cells were purchased from ATCC (#CRL-1593.2), grown in Petri dishes as a suspension with RPMI-1640 medium supplemented with 10% HI-FBS and 1% penicillin-streptomycin.
 IIA1.6 cells kindly provided by Dr. Van de Winkel J. G. J. and Dr. Leusen J. H. W, grown in tissue culture treated dishes as weakly adherent cells with RPMI-1640 medium supplemented with 10% HI-FBS and 1% penicillin-streptomycin.
 RM1.PGLS kindly provided by Dr. Michael Sadelain of Memorial Sloan Ketering Cancer Center grown in tissue culture treated dishes as adherent cells with DMEM-high glucose supplemented with 10% HI-FBS and 1% Penicillin-streptomycin

| Target | Bead Labeling (pmol/bead) | Measured PSMA/um² | Calculated PSMA/um² | Observed % Phagocytosis (50 nM SyAM-P2) |
|---|---|---|---|---|
| Beads | 8.2 | 5577 | | 46.2 |
| | 5.7 | | 3876 | 24.0 |
| | 2.9 | | 1972 | 10.1 |
| RM1.PGLS | | 918 | | 0 |

Bead Binding Assay for PSMA Binding Constant
 The binding of each SyAm derivative to PSMA was evaluated on PSMA-coated beads. 6 μm streptavidin labeled beads (Polysciences) were incubated with 400 μg/m recombinant avi-tagged-PSMA protein for 30 minutes. Beads were washed twice with PBS, blocked with 1 mg/ml biotin for 30 minutes and then washed twice with TBS-A. 10⁵ beads were incubated with a dilution series of SyAm ranging from 1 μM-100 μM. Streptavidin-Alexa467 (Invitrogen) was added to a final concentration of 3.3 μM. Samples were incubated on ice for 30 minutes, washed twice with DPBS, and evaluated by an Accuri C6 flow cytometer. For binding to RM1.PGLS cells identical conditions were followed substituting RM1.PGLS cells for beads.

| Molecule | $EC_{50}$ of PSMA Binding (nM) | $EC_{50}$ FcγRI Binding (nM) |
|---|---|---|
| SyAM-P1 | 40.7 | 248.7 |
| SyAM-P2 | 26 | |
| SyAM-P3 | 23.2 | 57.7 |

IIA1.6 FcγRI Expressing Cell Binding Assay
 Peptide dilutions have been prepared in DMSO usually starting form 1 mM stock solution with further 10 fold dilution. Cells IIa1.6 stably transfected with FcγRIA/γ-chain and non-transfected IIa1.6 cells used as isogenic negative control, were grown to approximately 1.5-2×10⁶ cells/mL density, spun down and reconstituted in RPMI 1640 medium without phenol red, supplemented with 10% FBS and Pen/Strep mixture to cell density 1×10$^6$ cells/mL. A 100 uL aliquot of cells was further transferred into an eppendorf tube and left to cool on ice for 5-10 minutes. Following this 1 uL of peptide dissolved in DMSO was added to the cells, bringing final concentration of DMSO to 1%. After 1 hour incubation on ice with a peptide 5 uL of Streptavidin-Alexafluor 488 (2 mg/mL) was added to the cells and left incubating on ice for 30-60 minutes. After the incubation cells were washed two times with 1 mL of cold RPMI1640 medium without phenol red, supplemented with 10% FBS and Pen/Strep and finally washed once in 1 mL TBS Buffer (150 mM NaCl and 25 mM Tris, pH 7.4). Cells were resuspended in residual TBS buffer (usually ~100 uL) and analyzed via flow cytometry with detection in the FL1 channel.

PSMA Measurement

RM1.PGLS cells detached with enzyme free detachment solution with gentle pipetting up and down. Cells resuspended to a concentration of 1×10$^6$ in PBS with 5% BSA. This cell solution was transferred in 100 uL aliquots to eppendorf tubes and to the appropriate tubes 2 uL of phycoerythrin labeled anti-CD32a antibody was added. Eppendorfs were incubated on ice for 30 minutes. Samples were centrifuged at 1.1 RPM for 5 minutes at 4c and washed 2× with PBS 5% BSA solution. Cells were run on Accuri C6 flow cytometer until 20 k live cell counts were achieved. Quantitation R-Phycoerythrin beads from Bangs Laboratories were run immediately after samples per manufacturers instructions. Geometric mean fluorescence of FL-2 channel was entered into calibration worksheet provided by the manufacturer and PSMA levels calculated.

Effector Cell Priming

Three days before the experiments, a plate of U937 cells (approximately 60% confluent) was passed into a new Petri dish (10 mL colored RPMI growth media total volume). IFN-γ (20 μL, 100 μg/mL in DPBS) was added, and the cells were maintained in an incubator (37° C., 24 h). The cells were pelleted after 24 hours and resuspended in 10 mL of IFN-γ (20 uL, 100 ug/mL in DPBS) and maintained in an incubator (37° C., 24 h) For ROS production cells were resuspended in RPMI growth media (10 mL), and split equally into two Petri dishes. To each dish were added additional colored RPMI growth media (5 mL) and IFN-γ (20 μL, 100 μg/mL in DPBS), and maintained in an incubator (37° C., 24 h)

For phagocytosis: cells were transferred into a Falcon tube, and DiD (19 uL, final concentration=1.9 μM) was added. The cells were maintained in an incubator (37° C., 30 min), pelleted, aspirated, resuspended in RPMI growth media (10 mL), and split equally into two Petri dishes. To each dish were added additional colored RPMI growth media (5 mL) and IFN-γ (20 μL, 100 μg/mL in DPBS), and maintained in an incubator (37° C., 24 h).

ROS Production Assay

Primed U937 were suspended in color-free ADCP media at a concentration of 3×10$^5$ U937 cells and mixed with 105 PSMA coated beads and various concentrations of molecules in a 96 well plate in a volume of 90 uL. To each well was added 10 μl of 2.5 mM lucigenin (Tokyo Chemicals) solution to bring the total volume to 100p. The plate was centrifuged at 200 rcf for 2 minutes (PLATE SPINNER). The chemiluminescence was then measured at two minute intervals by plate reader (Biotek Synergy 2) for 60 to 90 minutes.

Assay for Molecule Induced Phagocytosis of Beads 6 uM streptavidin fluoresbrite YG microspheres from Polysciences were incubated with 4× concentration of avi-tagged PSMA for 30 minutes at room temperature in DPBS (concentration of avi-tagged PSMA is dependent on biotin loading capacity of microspheres). Beads were washed with DPBS 2× and resuspended in color-free ADCP media at 1.6 million beads/mL Phagocytosis: 25 uL of bead solution was added to 25 uL of ADCP media either with or without molecules at various concentrations in an eppendorf tube. To this 50 uL of 4 million/mL primed U937 cells were added, gently mixed and then centrifuged at 1.1 RPM for 2 minutes. The caps were opened and placed in an incubator (37° C., 1 hr) at which point the eppendorfs were closed and placed on ice. Samples were vortexed and run on an Accuri C6 flow cytometer for a total of 50 k counts.

Data analysis: For each experiment 50,000 events were counted. Forward and side scatter plots were optimally gated to remove debris particles and cellular aggregates. On a plot of FL-2 vs FL-4 the following populations were counted:

Population

| Population | Approximate FL-2 signal | Approximate FL-4 signal |
|---|---|---|
| Effector Cells | $10^3$-$10^4$ | $10^5$-$10^{6.5}$ |
| Target Beads | $10^6$-$10^7$ | $10^{2.5}$-$10^4$ |
| Double Positive Cells | $10^6$-$10^7$ | $10^5$-$10^{6.5}$ |

$$\% \text{ phagocytosis} = \frac{\text{(double positive cells)}}{\text{(remaining target cells)} + \text{(double positive cells)}} \times 100$$

Phagocytosis Assay of Cells

Target cell passing: Three days before the experiments, a plate of target cells, RM1.PGLS cells were passed into a new flask.

Effector cell priming: Three days before the experiments, a plate of U937 cells (approximately 60% confluent) was passed into a new Petri dish (10 mL colored ADCP media total volume). IFN-γ (20 μL, 100 μg/mL in DPBS) was added, and the cells were maintained in an incubator (37° C., 24 h). The cells were transferred into a Falcon tube, and DiD (19 uL, final concentration=1.9 μM) was added. The cells were maintained in an incubator (37° C., 30 min), pelleted, aspirated, resuspended in colored ADCP media (10 mL), and split equally into two Petri dishes. To each dish were added additional colored ADCP media (5 mL) and IFN-γ (20 μL, 100 μg/mL in DPBS), and the cells were maintained in an incubator (37° C., 24 h).

Target cell preparation: To a plate of target cells (60-80% confluent RM1.PGLS cells 10 mL total media volume) was added DiO (20 μL, final concentration=2 μM). The cells were maintained in an incubator (37° C., 30 min), aspirated, and washed with colored ADCP media (3×10 mL). Colored ADCP media (10 mL) was added. The cells were maintained in an incubator (37° C., 2 h), detached and resuspended in color-free ADCP media at a concentration of 0.5 million cells per mL Effector cell preparation: Both dishes of primed U937 cells were transferred into a Falcon tube, pelleted, aspirated, resuspended in color-free ADCP media (10 mL), counted, and diluted with color-free ADCP media to give a final concentration of 2 million cells per mL. Phagocytosis: All conditions were run in triplicate. For each experiment, into a sterile 2 mL Eppendorf tube were added color-free ADCP media (25 μL) containing either various concentrations of SyAM-Px or ARM-P8/Anti-DNP antibody, target cells (25 μL=12,500 cells), and effector cells (50 μL=100,000 cells), to give an effector-to-target ratio of 8:1. Tubes were gently agitated by hand. The cells were pelleted (2 min, 1100 rpm). The tubes were opened, maintained in an incubator (37° C. 1 h), resuspended by briefly agitating with a vortex, and analyzed by flow cytometry.

| Population | Approximate FL-1 signal | Approximate FL-4 signal |
|---|---|---|
| Effector Cells | $10^3$-$10^4$ | $10^5$-$10^{6.5}$ |
| Target Cells | $10^6$-$10^7$ | $10^{2.5}$-$10^4$ |
| Double Positive Cells | $10^6$-$10^7$ | $10^5$-$10^{6.5}$ |

$$\% \text{ phagocytosis} = \frac{\text{(double positive cells)}}{\text{(remaining target cells)} + \text{(double positive cells)}} \times 100$$

Amnis Imagestream Imaging

The phagocytosis assay was performed as described above. After one hour, cells were fixed in 3% formaldehyde for 30 minutes on ice. Cells were washed once in DPBS then stained with anti-CD14-APC and anti-CD11b-APC antibodies (Biolegend) for 30 minutes on ice. Cells were washed once in DPBS then passed through a 70 μm cell strainer. 30,000 events per sample were collected on the Amnis Imagestream X flow cytometer. Double positive events were then manually scored for phagocytic cup formation or complete engulfment of the target. Data was analyzed on Amnis IDEAS software.

REFERENCES

1. Hansel, T. T.; Kropshofer, H.; Singer, T.; Mitchell, J. A.; George, A. J. T., The safety and side effects of monoclonal antibodies. *Nat Rev Drug Discov* 2010, 9 (4), 325-338.
2. Weiner, L. M., Building better magic bullets-improving unconjugated monoclonal antibody therapy for cancer. *Nat Rev Cancer* 2007, 7 (9), 701-706.
3. Siberil, S.; Dutertre, C. A.; Fridman, W. H.; Teillaud, J. L., Fc gamma R: The key to optimize therapeutic antibodies? *Crit. Rev. Oncol./Hematol.* 2007, 62(1), 26-33.
4. McEnaney, P. J.; Parker, C. G.; Zhang, A. X.; Spiegel, D. A., Antibody-Recruiting Molecules. An Emerging Paradigm for Engaging Immune Function in Treating Human Disease. *ACS Chemical Biology* 2012, 7(7), 1139-1151.
5. Cuesta, n. M.; Sainz-Pastor, N.; Bonet, J.; Oliva, B.; ¡l varez-Vallina, L., Multivalent antibodies: when design surpasses evolution. *Trends in biotechnology* 2010, 28 (7), 355-362.
6. James, N. D.; Atherton, P. J.; Jones, J.; Howie, A. J.; Tchekmedyian, S.; Curnow, R. T., A phase II study of the bispecific antibody MDX-H210 (anti-HER2×CD64) with GM-CSF in HER2+ advanced prostate cancer. *Br J Cancer* 2001, 85 (2), 152-156.
7. Li, Y.; O'Dell, S.; Walker, L. M.; Wu, X.; Guenaga, J.; Feng, Y.; Schmidt, S. D.; McKee, K.; Louder, M. K.; Ledgerwood, J. E.; Graham, B. S.; Haynes, B. F.; Burton, D. R.; Wyatt, R. T.; Mascola, J. R., Mechanism of Neutralization by the Broadly Neutralizing HIV-1 Monoclonal Antibody VRC01. *Journal of Virology* 2011, 85 (17), 8954-8967.
8. (a) Jakobsche, C. E.; McEnaney, P. J.; Zhang, A. X.; Spiegel, D. A., Reprogramming Urokinase into an Antibody-Recruiting Anticancer Agent. *ACS Chemical Biology* 2011, 7 (2), 316-321; (b) Murelli, R. P.; Zhang, A. X.; Michel, J.; Jorgensen. W. L.; Spiegel, D. A., Chemical Control over Immune Recognition: A Class of Antibody-Recruiting Small Molecules That Target Prostate Cancer. *Journal of the American Chemical Society* 2009, 131 (47), 17090-17092; (c) Parker, C. G.; Domaoal, R. A., Anderson, K. S.; Spiegel, D. A., An Antibody-Recruiting Small Molecule That Targets HIV gp120. *Journal of the American Chemical Society* 2009, 131 (45), 16392-16394.
9. Spiegel, D. A., Grand Challenge Commentary. Synthetic immunology to engineer human immunity. *Nat Chem Biol* 2010, 6 (12), 871-872.
10. Society, A. C., Cancer Facts & FIGS. 2011. Society, A. C., Ed. Atlanta, 2011.
11. Nimmerjahn, F.; Ravetch, J. V., Fc[gamma] receptors as regulators of immune responses. *Nat Rev Immunol* 2008, 8 (1), 34-47.
12. Bonetto, S.; Spadola, L.; Buchanan, A. G.; Jermutus, L.; Lund, J., Identification of cyclic peptides able to mimic the functional epitope of IgG1-Fc for human Fc gamma RI. *Faseb J.* 2009, 23 (2), 575-585.
13. Berntzen, G.; Andersen, J. T.; Ustgard, K.; Michaelsen, T. E.; Mousavi, S. A.; Qian, J. D.; Kristiansen, P. E.; Lauvrak, V.; Sandlie, I., Identification of a High Affinity Fc gamma RIIA-binding Peptide That Distinguishes Fc gamma RIIA from Fc gamma RIIB and Exploits Fc gamma RIIA-mediated Phagocytosis and Degradation. *J. Biol. Chem.* 2009, 284 (2), 1126-1135.
14. Cendron, A. C.; Wines, B. D.; Brownlee, R. T. C.; Ramsland, P. A.; Pietersz, G. A.; Hogarth, P. M., An FcγRIIa-binding peptide that mimics the interaction between FcγRIIa and IgG. Molecular Immunology 2008, 45 (2), 307-319.
15. Wang, S.-Y.; Veeramani, S.; Racila, E.; Cagley, J.; Fritzinger, D. C.; Vogel, C.-W.; St John, W.; Weiner, G. J., Depletion of the C3 component of complement enhances the ability of rituximab-coated target cells to activate human NK cells and improves the efficacy of monoclonal antibody therapy in an in vivo model. *Blood* 2009, 114 (26). 5322-5330.

The invention claimed is:

1. A method of inhibiting metastasis of prostate cancer in a patient in need thereof comprising administering to the patient a composition comprising an effective amount of a compound according to the chemical structure:

wherein [IBT] is an FcγRI receptor binding moiety according to the chemical structure:
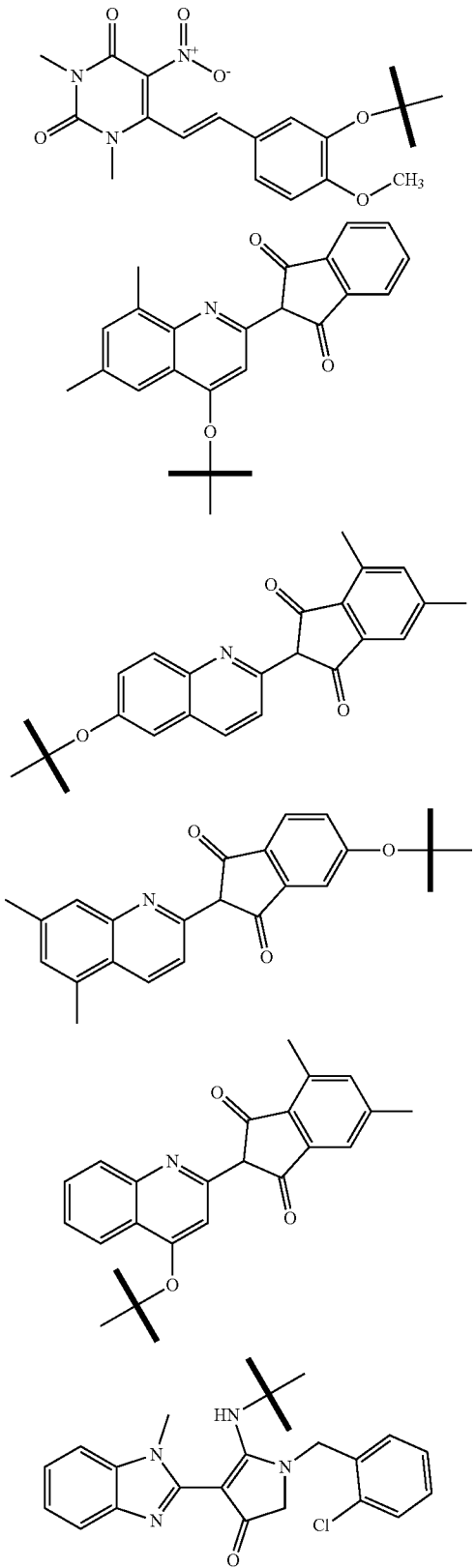
-continued
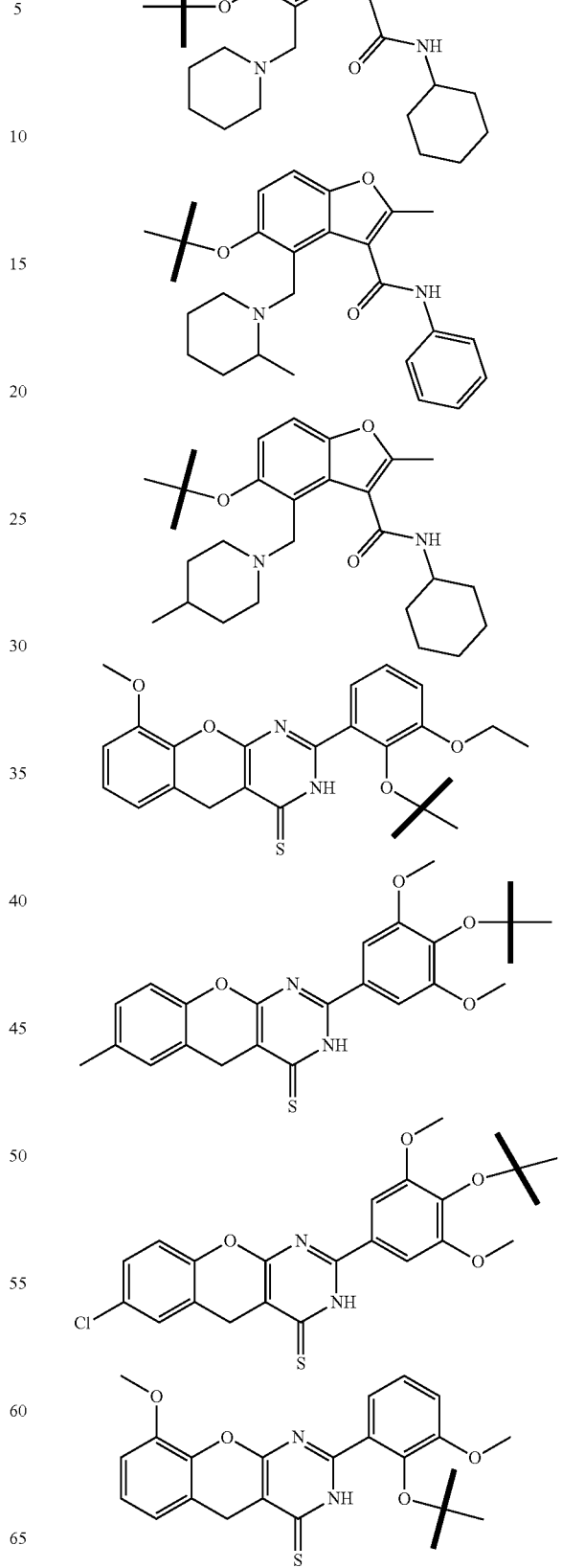

89
-continued
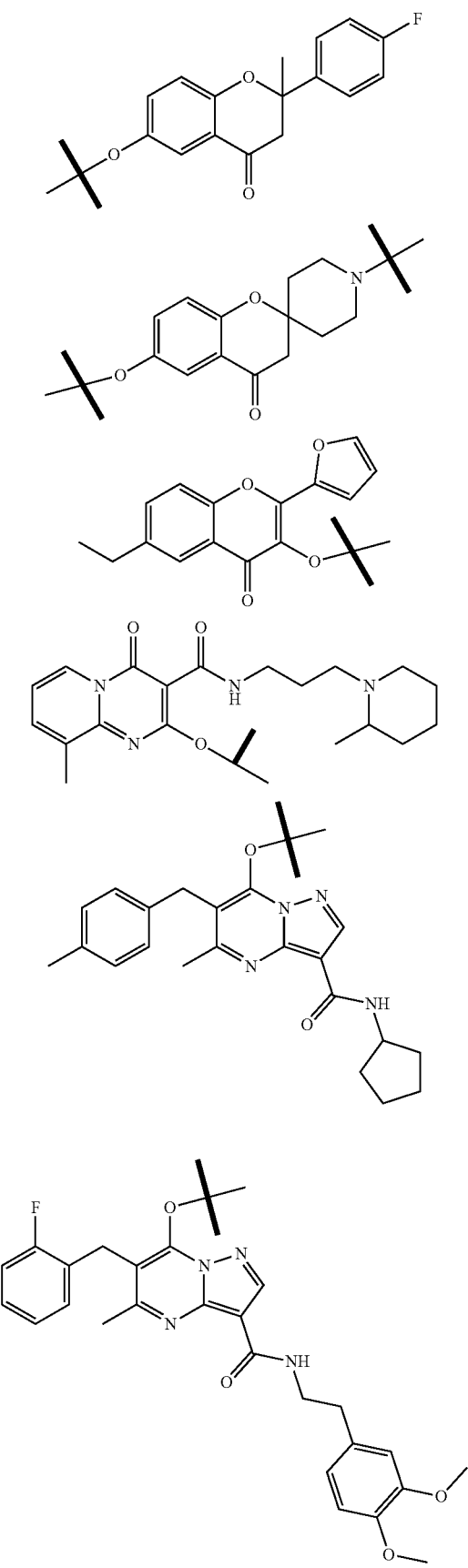
90
-continued
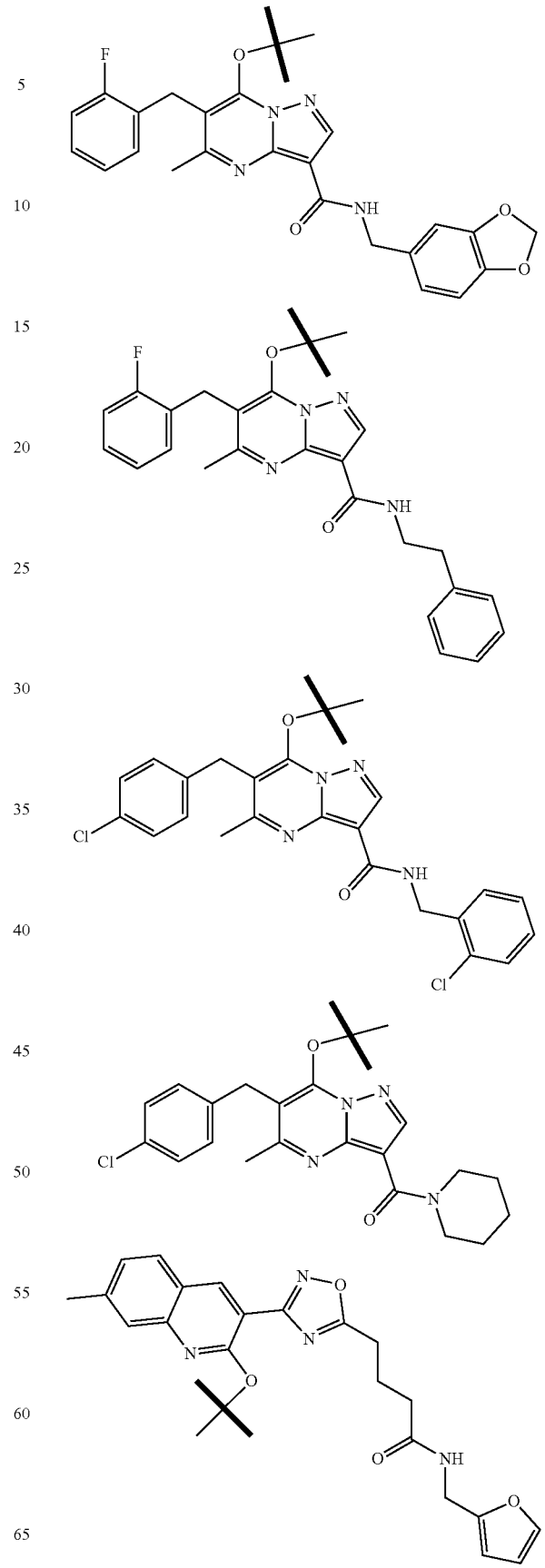

91
-continued
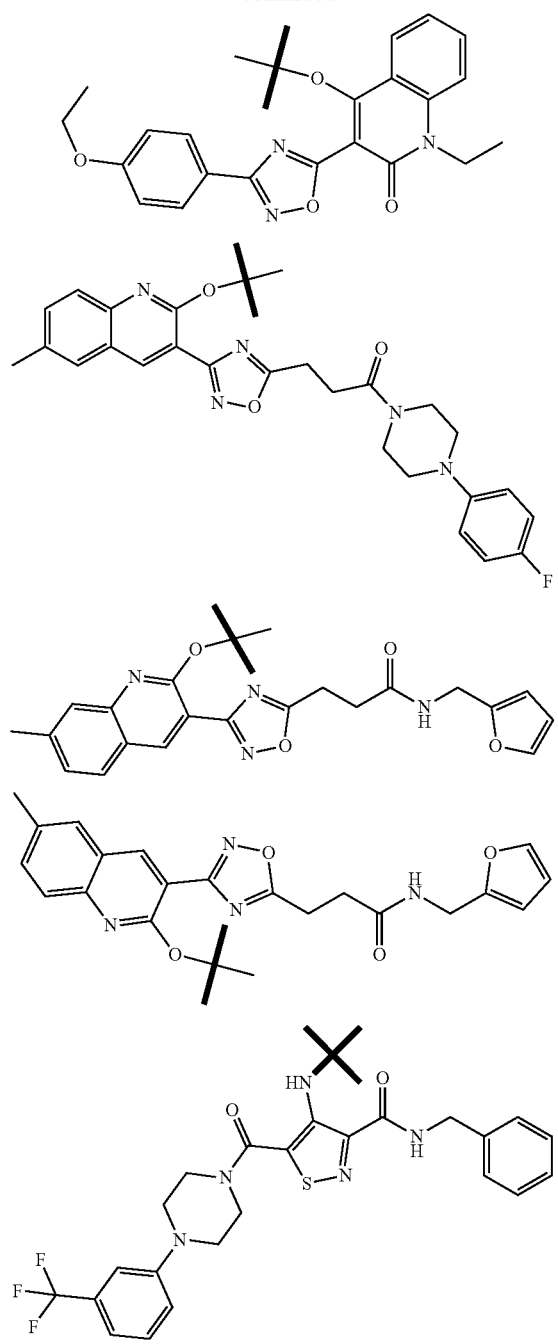
92
-continued
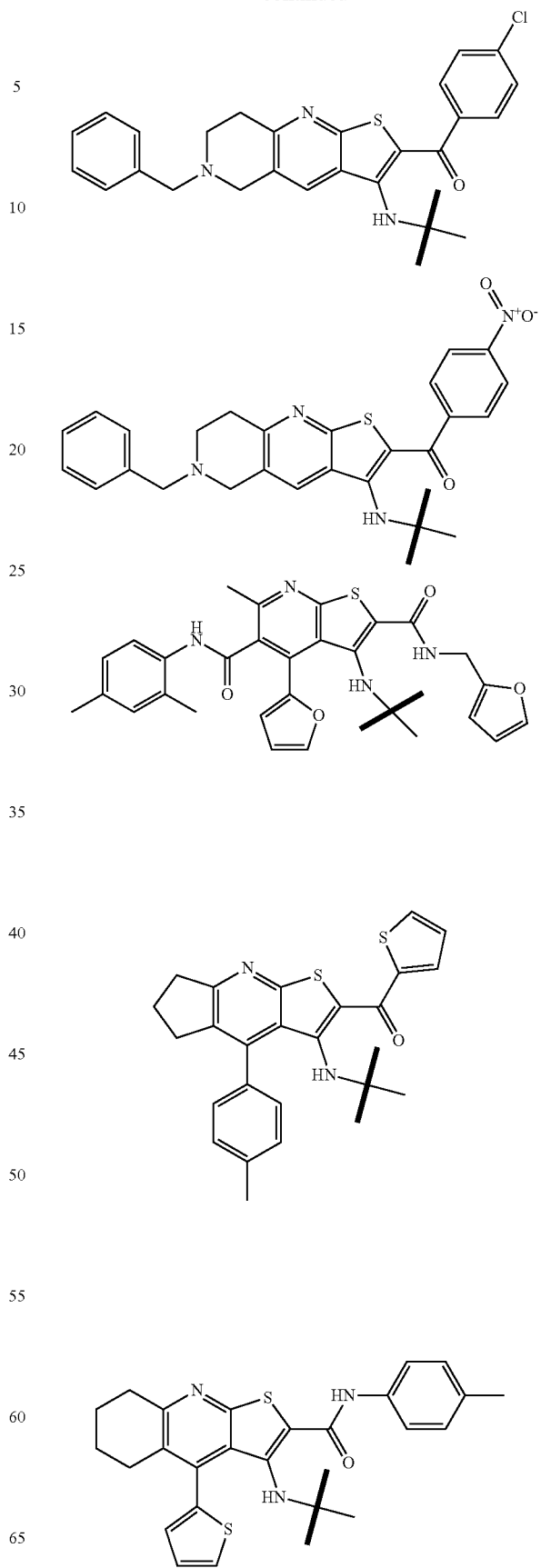

93
-continued
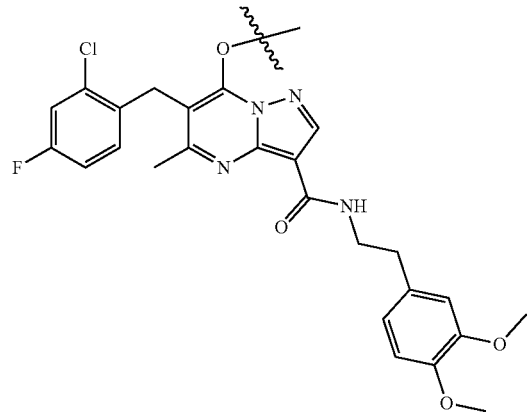
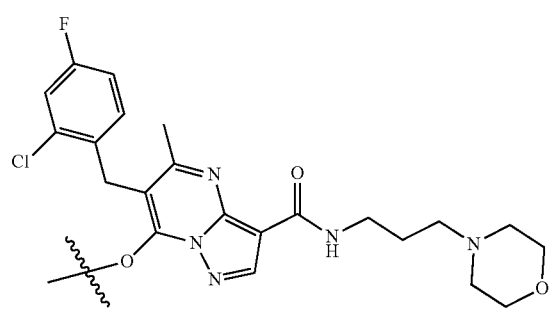
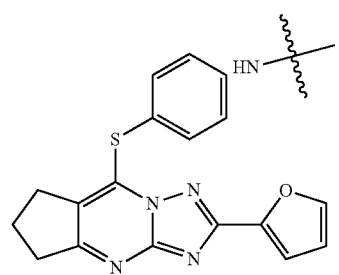
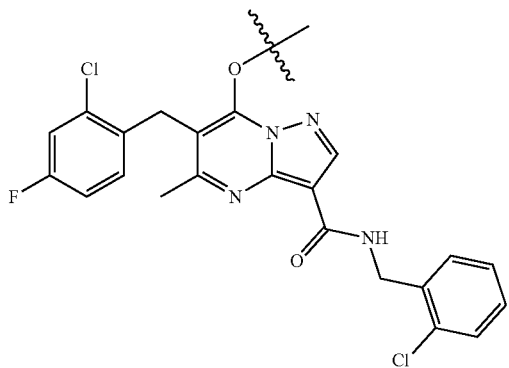
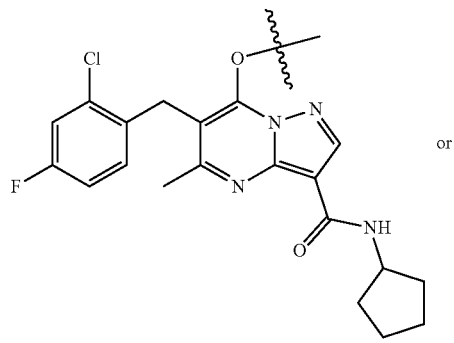
or
94
-continued
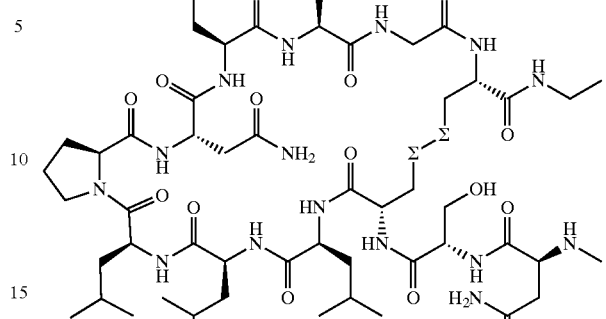
CP33
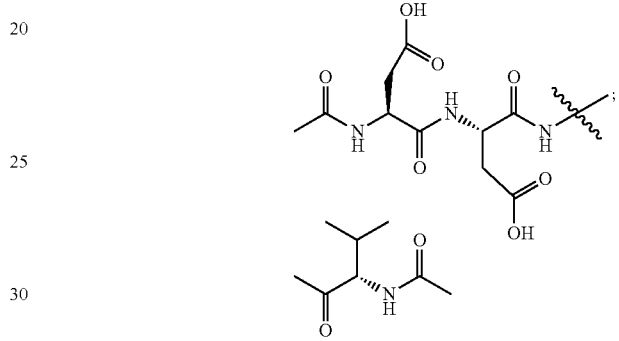
[CBT] is a cell binding moiety which binds to prostate specific membrane antigen (PSMA) expressed by a cancer cell according to the chemical structure:
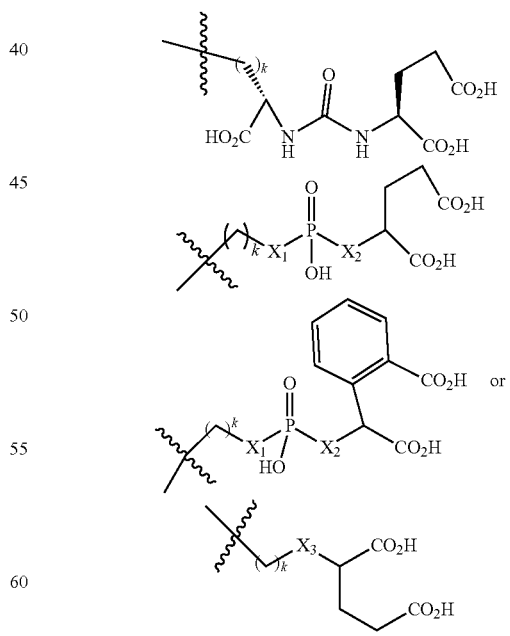
Where $X_1$ and $X_2$ are each independently $CH_2$, O, NH or S;
$X_3$ is O, $CH_2$, $NR^1$, S(O), $S(O)_2$, —$S(O)_2O$, —$OS(O)_2$, or $OS(O)_2O$;

$R^1$ is H, a $C_1$-$C_3$ alkyl group, or a —C(O)($C_1$-$C_3$) group;
k is an integer from 0 to 20;
$L_1$ and $L_2$ are linker groups, which groups optionally include one or more bifunctional connector groups [CON];
[MULTICON} is a bifunctional or multifunctional connector group which, when present, connects at least one [IBT] group to at least one [CBT] group through a linker;
MCON is 0, 1, 2 or 3;
n" and n''' are each independently 1, 2, 3, 4 or 5; and
NL1 and NL2 are each an integer from 0 to 5, with the proviso that n"≥NL1 and n'''≥NL2 and at least one of NL1 and NL2 is at least 1, or
a pharmaceutically acceptable salt or stereoisomer thereof.

2. The method of claim 1, wherein MCON is 0, 1 or 2.

3. The method of claim 1, wherein n is 1, 2, or 3 and n' is 1 or 2.

4. The method of claim 1, wherein NL1 is 1 and NL2 is 1.

5. The method of claim 1, wherein the [IBT] group is CP33.

6. The method of claim 1, wherein the [IBT] group is CP33.

7. The method of claim 1, wherein the [CBT] group is a group according to the chemical structure:

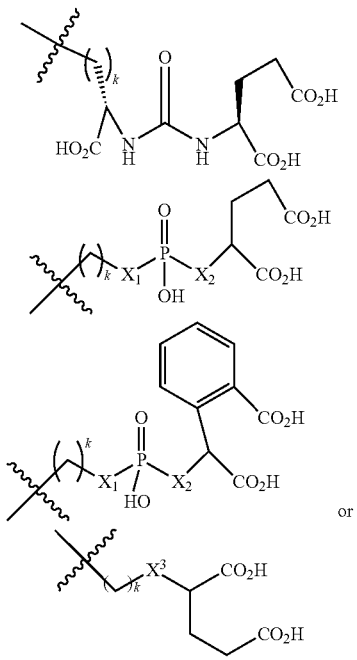

wherein $X_1$ and $X_2$ are each independently $CH_2$, O, NH, or S;
$X_3$ is O, $CH_2$, $NR^1$, S(O), S(O)$_2$, —S(O)$_2$O, —OS(O)$_2$, or OS(O)$_2$O;
$R^1$ is H, a $C_1$-$C_3$ alkyl group, or a —C(O)($C_1$-$C_3$) group; and
k is an integer from 0 to 12, or a salt or enantiomer thereof.

8. The method of claim 1, wherein at least one linker optionally contains a [CON] group according to the chemical structure:

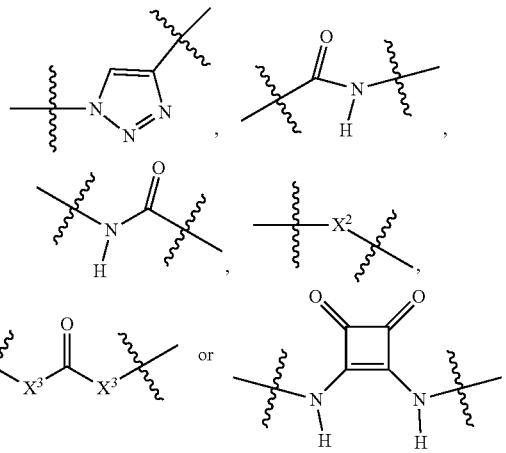

wherein $X^2$ is O, S, $NR^4$, S(O), S(O)$_2$, —S(O)$_2$O, —OS(O)$_2$, or OS(O)$_2$O;
$X^3$ is O, S, $NR^4$; and
$R^4$ is H, a $C_1$-$C_3$ alkyl or alkanol group, or a —C(O)($C_1$-$C_3$) group.

9. The method of claim 1, wherein at least one linker optionally contains a [CON] group, wherein the [CON] group is according to the chemical structure:

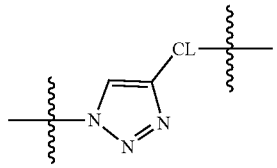

wherein CL is

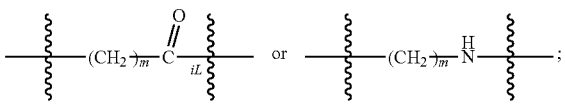

m is an integer from 0 to 12, and
iL is 0 or 1.

10. The compound according to claim 1, wherein the linker group $L_1$ or $L_2$ comprises:
polyethyleneglycol (PEG) linkages, polypropylene glycol linkages, or polyethyleneglycol-co-polypropylene polymers from 1 to 100 units in length;
a linker according to the structure:

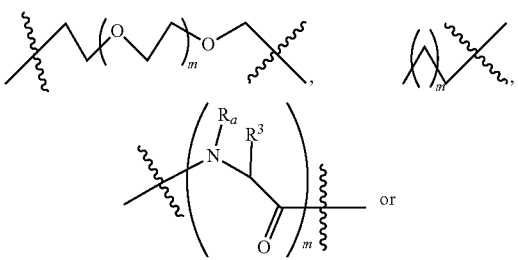

-continued

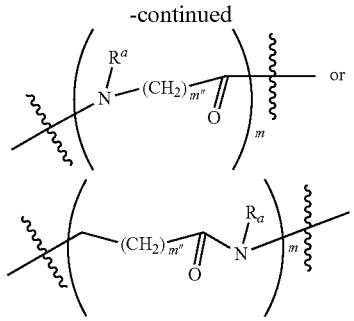

wherein $R_a$ is H, $C_1$-$C_3$ alkyl, alkanol or forms a cyclic ring with $R^3$ in the case of proline and $R^3$ is a side chain derived from an amino acid;

m" is an integer from 0 to 25; and m is an integer from 1 to 100; wherein each of the linker groups is optionally further linked through amide groups, keto groups, amine groups or amino acids.

11. The method according to claim 1 wherein the linker group $L_1$ or $L_2$ comprises a linker according to the structure:

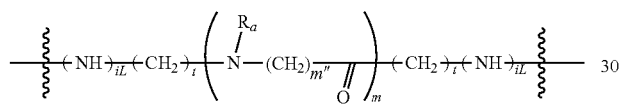

wherein $R_a$ is H or a $C_1$-$C_3$ alkyl;

m is an integer from 1 to 12;

m" is an integer 1, 2, 3, 4, 5, or 6;

t is 0, 1, 2, 3, 4, 5, or 6; and iL is 0 or 1, wherein the linker optionally contains a [CON] group and is linked to a [CBT] group at one end optionally through said [CON] group; or a linker according to the structure:

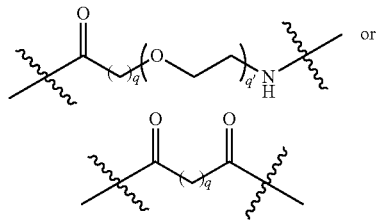

wherein q is an integer from 0-12; and q' is 1 to 12; or a linker according to the chemical structure:

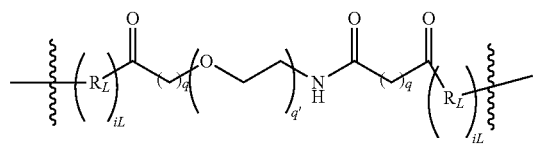

wherein q is an integer from 0-12; and q' is 1 to 12;

iL is 0 or 1; and $R_L$ is an amino acid or an oligopeptide or a linker succinimide according to the chemical structure:

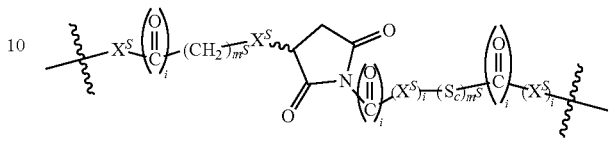

wherein each $X^S$ is independently S, O or N—$R^5$;

$R^S$ is H or $C_{1-3}$ alkyl;

$S_c$ is $CH_2$; $CH_2O$; or $CH_2CH_2O$;

i is 0 or 1; and $m^S$ is 0, 1, 2, 3, 4, 5, or 6, or a linker according to the chemical formula:

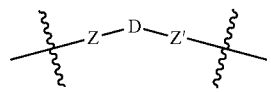

wherein Z and Z' are each independently a bond, —$(CH_2)_i$—O, —$(CH_2)_i$—S, —$(CH_2)_i$—N—R,

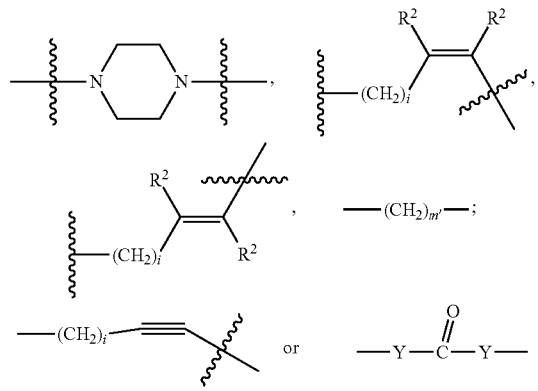

wherein the Z or Z' group, is optionally bonded to another linker group, a connector group [CON], a [MULTI-CON] group, [IBT] or [CBT];

each R is H, or a $C_1$-$C_3$ alkyl or alkanol group;

each $R^2$ is independently H or a $C_1$-$C_3$ alkyl group;

each Y is independently a bond, O, S or N—R;

each i is independently 0 to 100;

D is

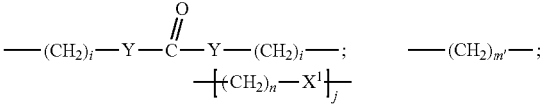

or
a bond, or D is

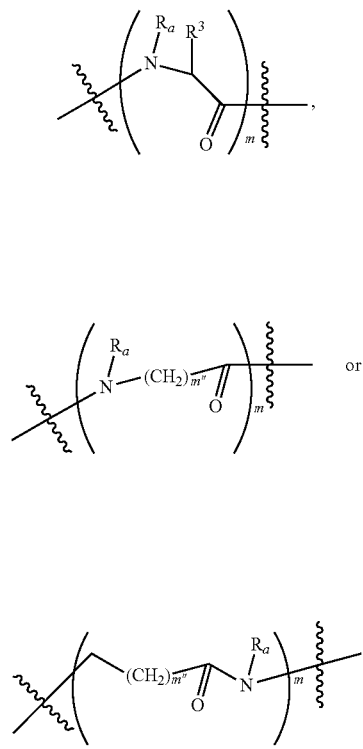

or a polypropylene glycol or polypropylene-co-polyethylene glycol linker having between 1 and 100 glycol units;
with the proviso that Z, Z' and D are not each simultaneously bonds;
each i is independently 0 to 100;
j is 1 to 100;
m is an integer from 1 to about 100; and
n is an integer from 1 to about 100;
m' is 1 to 100;
m" is an integer between 0 to 25;
n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
X' is O, S or N—R;
R in N—R above is H, a $C_1$-$C_3$ alkyl or alkanol group; and
$R_a$ is H, $C_1$-$C_3$ alkyl or alkanol or forms a cyclic ring with $R^3$ in the case of proline and $R^3$ is a side chain derived from an amino acid.

12. The method of claim 1, wherein the composition further comprises an effective amount of an additional anticancer agent.

13. The method of claim 12, wherein the additional anticancer agent is an antimetabolite, an inhibitor of topoisomerase I and II, an alkylating agent, a microtubule inhibitor or mixtures thereof.

14. The method of claim 12, wherein the additional anticancer agent is aldesleukin; aemtuzumab; alitretinoin; allopurinol; altretamine; amifostine; anastrozole; arsenic trioxide; aparaginase; BCG Live; bexarotene capsules; bexarotene gel; bleomycin; busulfan intravenous; busulfan oral; calusterone; capecitabine; carboplatin; carmustine; carmustine with poifeprosan 20 iplant; celecoxib; chlorambucil; cisplatin; cladribine; cyclophosphamide; cytarabine; cytarabine liposomal; dacarbazine; dactinomycin; actinomycin D; dabepoetin alfa; daunorubicin liposomal; daunorubicin, daunomycin; dnileukin diftitox, dexrazoxane; docetaxel; doxorubicin; doxorubicin liposomal; domostanolone propionate; eliott's B soution; epirubicin; eoetin alfa estramustine; etoposide phosphate; etoposide (VP-16); exemestane; flgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; nfetumomab; LOddC; orelvekin; oxaliplatin; paclitaxel; pamidronate; pegademase; pegaspargase; pegfilgrastim; pentostatin; pipobroman; plicamycin; mithramycin; porfimer sodium; procarbazine; quinacrine; rasburicase; rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustarg; valrubicin; valtorcitabine (monoval LDC); vinblastine; vinorelbine; zoledronate; and mixtures thereof.

15. The method of claim 1, wherein the composition further comprises at least one agent selected from the group consisting of flutamide, bicalutamide, nilutamide, cyproterone acetate, ketoconazole, aminoglutethimide, abarelix, leuprolide, goserelin, triptorelin, buserelin, abiraterone acetate, sorafenib and mixtures thereof.

16. The method of claim 1, wherein the composition further comprises at least one agent selected from the group consisting of eulexin, flutamide, goserelin, leuprolide, lupron, nilandron, nilutamide, zoladex and mixtures thereof.

17. The method of claim 1, wherein the patient having prostate cancer also has a form of cancer other than prostate cancer.

18. The method of claim 17, wherein the other form of cancer is stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer or lymphoma.

19. The method of claim 17, wherein the other form of cancer is a carcinoma, a malignant melanoma, a myeloproliferative disease, a sarcoma, a tumor of the central nervous system, a germ-line tumor, a mixed type of neoplasia or a tumor of mixed origin.

20. A method of inhibiting metastasis of prostate cancer in a patient in need thereof comprising administering to the patient a composition comprising an effective amount of a compound according to the chemical structure:

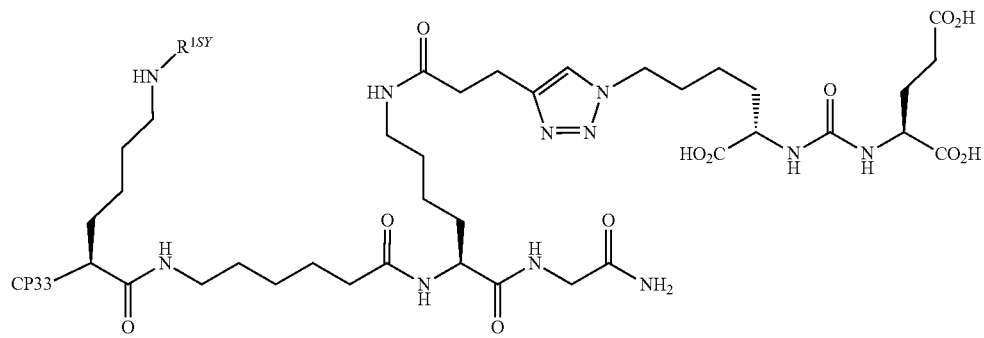

Wherein $R^{1SY}$ is independently H, a $C_1$-$C_{12}$ alkyl group, an acyl group or biotin; and
CP33 is a group according to the chemical structure:

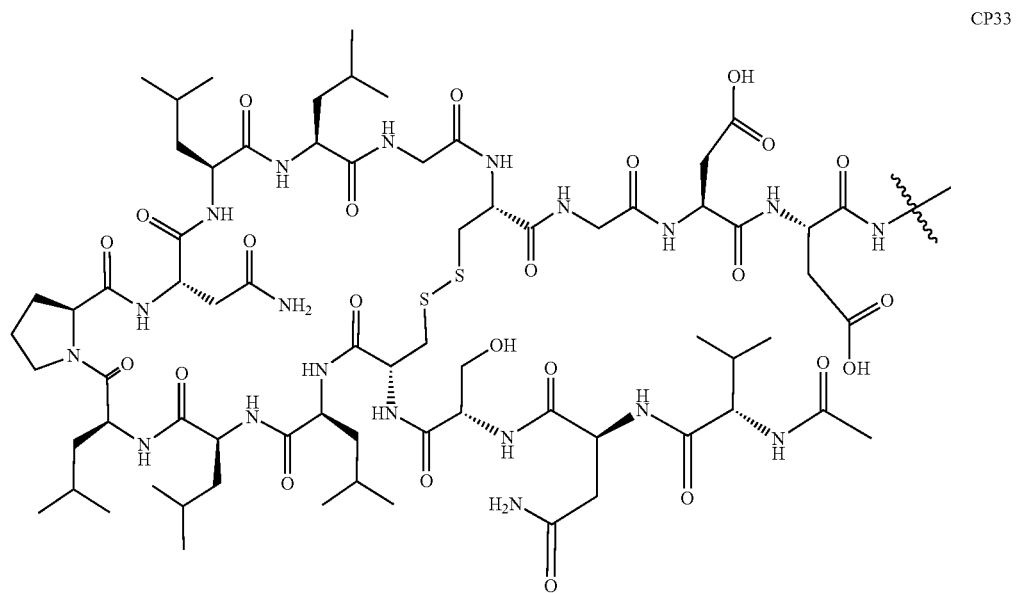 [SMILES: *NC(=O)[C@H](CC(=O)O)NC(=O)[C@H](CC(=O)O)NC(=O)CNC(=O)[C@@H]1CSSC[C@H](NC(=O)[C@H](CO)NC(=O)[C@H](CC(N)=O)NC(=O)[C@@H](NC(C)=O)C(C)C)C(=O)N[C@@H](CC(C)C)C(=O)N[C@@H](CC(C)C)C(=O)N[C@@H](CC(C)C)C(=O)N2CCC[C@H]2C(=O)N[C@@H](CC(N)=O)C(=O)N[C@@H](CC(C)C)C(=O)N[C@@H](CC(C)C)C(=O)NCC(=O)N1]

or a pharmaceutically acceptable salt or stereoisomer thereof.

* * * * *